US012714339B1

(12) United States Patent
Janigro et al.

(10) Patent No.: US 12,714,339 B1
(45) **Date of Patent: *Aug. 25, 2026**

(54) ASSAY AND POINT OF CARE DEVICE UTILIZING SALIVA FOR DIAGNOSIS AND TREATMENT OF NEUROLOGICAL CONDITIONS AFFECTING BRAIN HEALTH

(71) Applicant: FloTBI Inc., Cleveland, OH (US)

(72) Inventors: Damir Janigro, Cleveland Heights, OH (US); Aaron Dadas, Northfield, OH (US); Edward J. Rapp, Cleveland Heights, OH (US)

(73) Assignee: FloTBI Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,371

(22) Filed: Jun. 19, 2023

Related U.S. Application Data

(63) Continuation of application No. 15/833,160, filed on Dec. 6, 2017, now Pat. No. 11,717,195, which is a (Continued)

(51) Int. Cl.
*A61B 5/145* (2006.01)
*A61B 5/15* (2006.01)
(Continued)

(52) U.S. Cl.
CPC .... *A61B 5/14546* (2013.01); *A61B 5/150022* (2013.01); *A61B 5/150358* (2013.01);
(Continued)

(58) Field of Classification Search
CPC .......... A61B 5/14546; A61B 5/150022; A61B 5/150358; A61B 5/14517;
(Continued)

(56) References Cited

U.S. PATENT DOCUMENTS 11,717,195 B2 * 8/2023 Janigro ............. A61B 5/14546 422/82.01

OTHER PUBLICATIONS

Liu, Yun, et al. "A Sensitive Microchip-Based Immunosensor for Electrochemical Detection of Low-Level Biomarker S100B." Electroanalysis 25.4 (2013): 1050-1055. (Year: 2013).*

(Continued)

*Primary Examiner* — Robert J Eom
(74) *Attorney, Agent, or Firm* — Robert N. Schmidt

(57) ABSTRACT

The present invention relates to systems and methods for assessing brain health and detecting neurological conditions. The invention more particularly relates to systems and methods for diagnosing neurological conditions and analyzing rain health from analysis of a biological fluid sample, such as a saliva sample, that looks for and determines the significance of peripheral markers of blood-brain barrier disruption. The present invention further provides a diagnostic system and method with a higher negative predictive value of brain injury than currently known tests are able to provide, so as to reduce the need for computerized tomography or magnetic resonance imaging scans to affirmatively determine that brain or cerebrovascular injury has not occurred, and thus to improve suspected brain injury patient health care while reducing the expense of such care.

20 Claims, 28 Drawing Sheets

Related U.S. Application Data continuation-in-part of application No. 15/264,682, filed on Sep. 14, 2016, now abandoned.

(60) Provisional application No. 62/514,289, filed on Jun. 2, 2017, provisional application No. 62/316,648, filed on Apr. 1, 2016, provisional application No. 62/240,152, filed on Oct. 12, 2015.

(51) Int. Cl.
*C12Q 1/6883* (2018.01)
*G01N 33/53* (2006.01)
*G01N 33/68* (2006.01)

(52) U.S. Cl.
CPC ....... *C12Q 1/6883* (2013.01); *G01N 33/6896* (2013.01); *A61B 5/14517* (2013.01); *A61B 5/150755* (2013.01); *G01N 33/53* (2013.01); *G01N 2800/60* (2013.01)

(58) Field of Classification Search
CPC ............ A61B 5/150755; C12Q 1/6883; G01N 33/6896; G01N 2800/60
See application file for complete search history.

(56) References Cited

OTHER PUBLICATIONS

Venkatasubbarao, Srivatsa, et al. "Field-based multiplex and quantitative assay platforms for diagnostics." Sensing Technologies for Global Health, Military Medicine, Disaster Response, and Environmental Monitoring; and Biometric Technology for Human Identification VIII. vol. 8029. SPIE, 2011. (Year: 2011).*

* cited by examiner 510
515
S100B
S100 B
S100B
S100 B
505
Strept-avidin
Strept-avidin
Streptavidin coated electrode
Gold
500
R1
C1
R2
Increased R2 (or S100B)
measured at same frequency
Increased R1 (or access R)
-ImZ (OhM)
ReZ (Ohm)

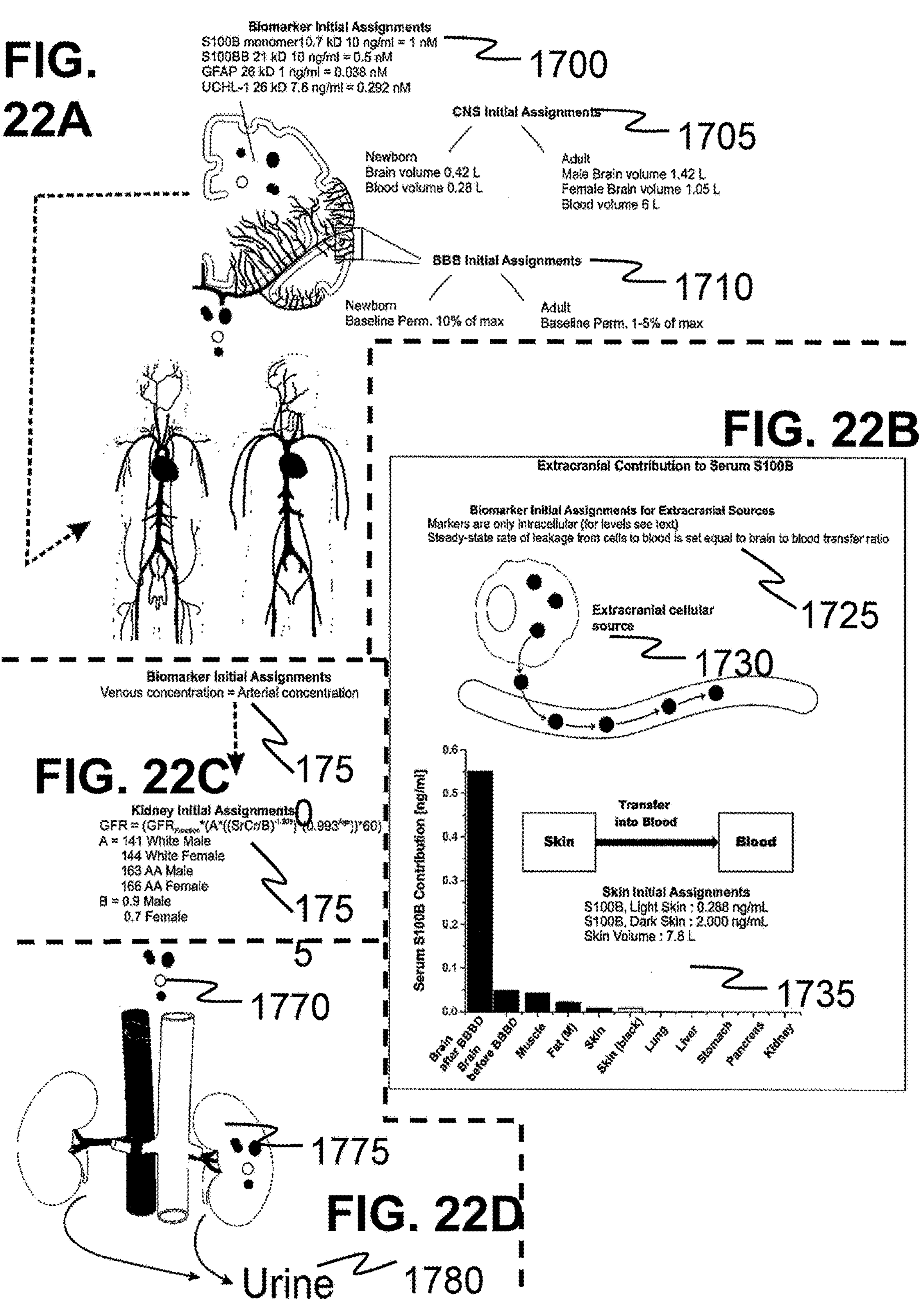
FIG. 22A
Biomarker Initial Assignments
S100B monomer10.7 kD 10 ng/ml = 1 nM
S100BB 21 kD 10 ng/ml = 0.5 nM
GFAP 26 kD 1 ng/ml = 0.038 nM
UCHL-1 26 kD 7.6 ng/ml = 0.292 nM
1700
CNS Initial Assignments
1705
Newborn
Brain volume 0.42 L
Blood volume 0.28 L
Adult
Male Brain volume 1.42 L
Female Brain volume 1.05 L
Blood volume 6 L
BBB Initial Assignments
1710
Newborn
Baseline Perm. 10% of max
Adult
Baseline Perm. 1-5% of max
FIG. 22B
Extracranial Contribution to Serum S100B
Biomarker Initial Assignments for Extracranial Sources
Markers are only intracellular (for levels see text)
Steady-state rate of leakage from cells to blood is set equal to brain to blood transfer ratio
1725
Extracranial cellular source
1730
Serum S100B Contribution [ng/ml]
Transfer into Blood
Skin
Blood
Skin Initial Assignments
S100B, Light Skin : 0.288 ng/mL
S100B, Dark Skin : 2.000 ng/mL
Skin Volume : 7.8 L
1735
Brain after BBBD
Brain before BBBD
Muscle
Fat (M)
Skin
Skin (black)
Lung
Liver
Stomach
Pancreas
Kidney
Biomarker Initial Assignments
Venous concentration = Arterial concentration
1750
FIG. 22C
Kidney Initial Assignments
A = 141 White Male
144 White Female
163 AA Male
166 AA Female
B = 0.9 Male
0.7 Female
1755
1770
1775
FIG. 22D
Urine
1780

S100B increase after BBBD (ng/mL)
0.30
0.25
0.20
0.15
0.10
0.05
0
2
4
6
8
10
minutes Change in serum S100B (ng/ml)
1.0
0.8
0.6
0.4
0.2
0.0
-0.2
-0.4
-0.6
-0.8
S100B = 0.0022*(% Radiologic index)
0
25
50
75
100
Radiologically measured BBBD by CT (% Radiologic Index)

Relative concentration in filtrate (dimensonless ratio of [])
1.0
0.8
0.6
0.4
0.2
0.0
0
10000
20000
30000
40000
50000
60000
70000
mw (D)

Half-Life (hours)
10.0
9.0
8.0
7.0
6.0
5.0
4.0
3.0
40 kD
21 kD
26 kD
10.7 kD
50
60
70
80
90
100
Kidney Function (% of homeostatic GFR)

2022
2020
2021
B.
2031
2030
A.

ASSAY AND POINT OF CARE DEVICE UTILIZING SALIVA FOR DIAGNOSIS AND TREATMENT OF NEUROLOGICAL CONDITIONS AFFECTING BRAIN HEALTH

CROSS-REFERENCE TO RELATED PATENT APPLICATIONS

This application is a continuation of U.S. patent application Ser. No. 15/833,160, which is both: 1) a non-provisional application that claims priority to provisional U.S. Patent Application Ser. No. 62/514,289, which was filed on Jun. 2, 2017; and 2) a continuation-in-part of U.S. patent application Ser. No. 15/264,682, which was filed on Sep. 14, 2016, where application Ser. No. 15/264,682 claims priority from two different provisional applications for patent in the United States: a) provisional U.S. Patent Application Ser. No. 62/240,152 which was filed on Oct. 12, 2015, and b) provisional U.S. Patent Application Ser. No. 62/316,648 which was filed on Apr. 1, 2016. The specifications and drawings of each of the above applications are hereby incorporated by reference in their entirety.

FIELD OF THE INVENTION

The present invention relates to a device, system, composition, apparatus and/or method for monitoring the status of brain health biomarkers in saliva. Saliva is a very attractive bodily fluid for the diagnosis of diseases because collection of saliva is economical, safe, easy and can be performed without the help of health care workers, allowing for easy and readily available home-based or field sampling. Collection of saliva is an acceptable and fast process that does not provoke pain while providing for rapid screening and testing of the subject. The present invention further provides a diagnostic system and method with a higher negative predictive value of brain injury than currently known tests are able to provide, so as to reduce the need for computerized tomography or magnetic resonance imaging scans to affirmatively determine that brain or cerebrovascular injury has not occurred, and thus to improve health care delivery to suspected brain injury patients while reducing the overall expense of such care.

TECHNICAL FIELD

The present invention provides a simplified device and method related to the detection and quantification of brain-derived biomarkers in saliva. In certain embodiments, the present invention comprises a point-of-care or point-of-injury apparatus or device for measuring physiological biomarkers in saliva. In a particular embodiment, the present invention provides a method and apparatus for longitudinal monitoring salivary brain-derived protein.

TECHNOLOGY REVIEW

The determination of salivary drug concentrations or stress hormones is one of the major applications related to saliva in laboratory medicine. The use of saliva instead of blood has several advantages, especially the stress-free sampling that can be performed by the patient at any time without the assistance of a physician. Markers of brain damage or brain health have been used for many years in experimental settings but have not reached clinical acceptance for a variety of reasons, including the task of performing a blood draw on-site where a phlebotomist or physician is not available.

The blood-brain barrier is primarily composed of microvascular endothelial cells linked by tight junctions that largely prevent molecular communication between blood and the brain. Some of the unique properties of the blood-brain barrier are induced by perivascular glia. Thus, the blood-brain barrier is constituted of both endothelial cells and glial end feet. Perivascular pericytes and microglia may also be considered active components of the blood-brain barrier. Astrocytes and their processes invest more than 90% of endothelial capillaries, and their end feet are projected tightly around the endothelial cells. Astrocytic proteins are synthesized and released next to capillaries, but owing to the negligible trans-endothelial permeability to proteins, they extravasate into the serum only when the blood-brain barrier is breached. Glial fibrillary acidic protein (GFAP) and S100B are two examples of proteins more or less specifically expressed by central nervous system (CNS) astrocytes that are activated with increased blood-brain barrier permeability. These and other peripheral markers, such as UCHL-1, can be used to peripherally detect changes that occur in the brain parenchyma. S100B and GFAP can be measured by direct enzyme-linked immunoabsorbent assay (ELISA). Thus, peripheral detection of brain-specific proteins can be used to monitor changes in blood-brain barrier integrity. Peripheral markers of blood-brain barrier disruption are molecular entities that appear in blood or other fluids of the body after leakage or spillage across a damaged or pathologic blood-brain barrier or other parts of the cerebral circulation. Detection and/or measuring of the protein markers (S100B, GFAP) can be performed using various modalities, both invasive and semi- or non-invasive. Serum S100B, UCHL-1 and GFAP are indicators of blood-brain barrier (BBB) leakage which all can be detected at various points using modalities such as either computed tomography (CT) or magnetic resonance imaging (MRI), particularly contrast-enhanced CT or MRI, or diffusion weighted magnetic resonance imaging (DWI), or in addition to lumbar puncture. For discussion further defining such peripheral markers and providing examples, see the following references, each of which is herein incorporated by reference: U.S. Pat. No. 6,884,591 to Janigro et al., "Peripheral marker of blood brain barrier permeability"; Marchi N., Cavaglia M., Bhudia S., Hallene K., and Janigro D., "Peripheral markers of blood-brain barrier damage", *Clinica Chimica Acta* 2004; 342((1-2)):1-12; Fazio V., Bhudia S. K., Marchi N., Aumayr B., Janigro D., "Peripheral detection of S100beta during cardiothoracic surgery: what are we really measuring?" *Ann. Thorac. Surg.* 2004 July; 78(1):46-52; Marchi N., Rasmussen P. A., Kapural M., Fazio V., Cavaglia M., Janigro D., "Peripheral markers of brain damage and blood-brain barrier dysfunction", *Restorative Neurology and Neuroscience* 2003; 21(3-4):109-21; and Ben A. O., Vally J., Adem C., Foglietti M. J., and Beaudeux J. L., "Reference values for serum S-100B protein depend on the race of individuals", *Clin. Chem.* 2003 May; 49(5):836-7.

Levels of peripheral markers in a biological fluid sample can be determined and compared with a control sample (e.g., levels found in a normal population); changes above these baseline values may then indicative of blood-brain barrier dysfunction or permeability. These values have been, in the field of neurological diseases, almost always measured in blood or cerebrospinal fluid. In comparison, human saliva has not been used for the same purposes nearly as much. Recent large scale proteomic analyses have revealed that human saliva is also rich in proteins, some of which come from the blood circulation and hence can potentially serve as a general information pool for disease biomarker identification. The present invention describes the use of a specific, cell-free body fluid as a source of analytes, namely saliva. Proteins can move from blood circulation into salivary glands through active transportation, passive diffusion or ultrafiltration, some of which are then released into saliva and hence can potentially serve as biomarkers for diseases if accurately identified. Most excitingly, based on point-of-care technology salivary brain biomarkers could be a new use of salivary diagnostics and contribute to diagnosis of neurological diseases.

Traumatic brain injury (TBI) is an etiologic player for delayed neurological events, spanning from epilepsy to dementia. Minor head injury (MHI) represents up to 95% of head injuries. Typically, diagnosis and early management of MHI requires some form of medical imaging, such as computed tomography (CT) or clinical (in-hospital) observation of the patient. In-clinic observation is expensive and time consuming, and medical imaging, such as CT, is not always available or practical, involves potentially harmful ionizing radiation, and is also in addition relatively expensive. Further, given that only a small portion of patients with MHI actually have intracranial injuries and even fewer require neurosurgical intervention, the traditional tools for MHI and TBI analysis are even less efficacious or practical.

S100B, and specifically serum levels of S100B protein in biological fluids, are correlated with the presence and severity of neurological disorders, including TBI. S100B is generally considered to be a brain protein as it is found in vast majority to be located in the central nervous system, though it has since been shown to be present in extracerebral tissues, for example in the testes and skin, albeit usually in low concentrations. However, even though serum S100B may be found in low, but measureable, levels in healthy individuals, it rises rapidly in blood after head injury, and has relatively short half-life of approximately 30 to 90 minutes. Thus, S100B is generally segregated to the CNS, though when the BBB "opens", S100B and other proteins normally present in high concentrations in the CNS but not the rest of the body (such as GFAP and UCHL-1) are free to diffuse into the blood following their concentration gradients. Available imaging techniques for human research or clinical care lack the combination of very high resolution and massive data processing capacity necessary to visualize the structure of the BBB, and consequently, functional assessment of BBB status is performed by calculation of the cerebral spinal fluid (CSF) serum-albumin quotient (QA). In other words, by measuring the concentration ratio of albumin in the CNS to that in the patient's blood, it can be determined whether the BBB has been damaged or otherwise caused to open and become more permeable than under normal or injury-free conditions. In order to measure the concentration of albumin in the CNS, however, a lumbar puncture (spinal tap) typically must be performed to aspirate a measurable quantity of cerebrospinal fluid. Thus, much like imaging and in-clinic observation, calculation of the QA, though effective and accurate in measuring BBB permeability and thus predicting and measuring serum blood protein levels, is potentially expensive, carries a significant risk of developing headaches, hydrocephalus or infections, is highly invasive to the patient, and is highly impractical for point-of-care use. Recently, saliva has become an important biofluid for evaluation of physiological and pathological conditions in human subjects. The use of saliva for diagnostics has many advantages, including simple and non-invasive collection method, little or no need for pre-processing, minimal risk of contracting infections and easy, low-cost storage.

It is therefore an object of the present invention to provide systems and methods that allow for screening of patients with suspected neurological diseases using a non-invasive and non-toxic techniques by using saliva or other biological fluids. It is a further object of the present invention to provide such systems and methods that can be available at point of care or point of injury for readily available use virtually anywhere without requiring the patient to be moved or transported. It is further an object or the present invention to provide such screening systems and methods that are inexpensive and/or cost effective, particularly compared to existing imaging methods or blood-based diagnostics. It is yet further an object of the present invention to provide systems and methods for measuring specific markers, such as proteins or small molecules, that can help provide either a positive or negative indication for acute and delayed consequences of neurological diseases. It is still a further object of the present invention to improve the clinical significance and predictive value of peripheral markers of blood-brain barrier disruption by providing a system that employs a multistep algorithm that takes into account individual-specific characteristics and physiological and pathological variables that influence markers' stability and molecular integrity in biological fluids in order to provide the most accurate screening possible.

SUMMARY OF THE INVENTION

The present invention in part relates to methods and assays useful in determining with increased accuracy the true levels of a given marker of blood-brain barrier disruption and brain damage in saliva and thus to provide an improved, faster and less invasive diagnosis of diseased states such as traumatic brain injury. Patent application Ser. No. 15/264,682 filed on Sep. 14, 2016 is herein incorporated by reference.

Peripheral blood biomarkers of brain function have been used clinically to diagnose the presence, extent or absence of neurological diseases. Interpretation of results with these markers was confounded by limited understanding of their dependence on variables other than the disease condition itself. Examples of unexplored potential contributors to markers' appearance or persistence include half-life in blood, molecular weight, biophysical properties, and the effects of glomerular filtration, age, gender, and ethnicity (Dadas, A., Washington, J., Marchi, N., and Janigro, D. *Improving the clinical management of traumatic brain injury through the pharmacokinetic modeling of peripheral blood biomarkers* (2016) Fluids Barriers CNS 13; 21), which is herein incorporated by reference. Brain imaging data were used to model passage of markers across the blood-brain barrier (BBB) while literature data and our own data were used to model passage from the blood into saliva (FIG. 1A). Biomarker extravasation from brain to blood depends on the permeability of the BBB to a given marker. Under normal conditions and when the BBB is intact, endothelial tight junctions dramatically restrict the passage of polar or large (>~300 D) molecules. However, when the BBB is breached, appearance in blood of brain-derived protein biomarkers is comparable to what observed in systemic vessels. For example, after stroke, TBI or seizures increased BBB permeability allows passage of molecules that are used as peripheral, blood biomarkers of BBB disruption. While other means of extravasation have been shown (CSF-blood barrier and lymphatic drainage), all these share in common the presence in peripheral blood of otherwise excluded protein. In contrast to the BBB, passage of protein from blood to saliva is largely independent on neurological function. Salivary gland trauma usually occurs following a penetrating trauma of the parotid or submandibular region and occasionally these are associated with injuries to the adjacent facial structures such as the facial and lingual nerves, the ear, and bony structures of the face. Other causes of salivary gland trauma involve direct blunt injuries and trauma following radiotherapy of the head and neck. To our knowledge, there are no reports of mTBI affecting salivary function. Literature searches revealed a significant decrease of blood to saliva protein extravasation or transudation with increasing molecular weight (FIG. 1B). Thus, the steady-state permeability of the blood-to-saliva protein diffusion is preserved even at times when the BBB is breached. This results in selective exclusion of larger protein from salivary transudate even when these are present in blood.

Results of this model show, as described in (Janigro, D. *Assay devices for detecting neurological conditions or assessing brain health using peripheral markers of blood-brain barrier disruption* (2017) 115/264,682), which is also incorporated by reference: 1) changes in serum levels of biomarkers, due to confounders such as age or disease progression, are explained in terms of kidney filtration and molecular weight and size of the marker itself, 2) significant changes in the brain-to-blood volumetric ratio accompany the stages of infant and adult development, and this contributes to differences in biomarker concentrations; 3) the effects of extracranial contribution at steady-state are predicted in our model to be less important than suspected, while the contribution of BBB disruption was confirmed as a significant factor controlling markers' appearance in blood, where the biomarkers are typically detected; and 4) the contribution of skin to blood S100B levels depended on a direct correlation with pigmentation (e.g., tanning) and not ethnicity. Peripheral biomarkers have myriad potential uses for treatment, prediction, prognostication and pharmacovigilance in many diseases, including those of neurological nature. For example, levels of brain protein GFAP, S100B, tau and UCHL-1 in biological fluids have been shown to correlate with presence and severity of many neurological disorders. Blood levels of these markers are low but measurable; levels rise rapidly in blood after head injury, cortical contusions, seizures, or ischemic stroke. The possibility of using serum S100B in patients with minor head injury was first reported in 1995. It was first thought that S100B release was a biomarker of subtle brain damage after MHI, although data suggest that an equally relevant mechanism may involve the release of S100B through a disrupted BBB, without necessarily involving actual cellular damage. Comparable results were obtained with GFAP and UCHL-1 suggesting that these markers also appear in blood when the BBB is compromised.

As it relates to the passage from of these blood markers from blood to saliva, the method employed in the present invention optionally was based on the following assumptions (FIGS. 2 & 3):

$$\frac{\text{Marker concentration in saliva}}{\text{time}} = \text{Salivary flow rate} * (\text{Marker concentration in blood} * \text{Partition coefficient})$$

$$\text{Partition coefficient} = \frac{\text{Marker concentration in saliva}}{\text{Marker concentration in blood}}$$

where dimensions are g/L for marker's levels, partition coefficient is dimensionless and flow rate is expressed in ml/minute. For obvious reasons:

$$\text{Marker concentration(saliva, blood)} = \frac{\text{g}}{\text{organ volume}}$$

The initial values for these variables were set as shown in FIG. 2. The transfer of a protein from blood to the interstitial space in the salivary gland was described as:

$$\text{Transfer}\left(\frac{\text{mol}}{\text{min}}\right) = \text{Salivary blood flow}\left(\frac{\text{ml}}{\text{min}}\right) * (1 - \text{Reflectance}) + (\textit{Conc.grad.}) * \textit{Perm.}\text{marker}\left(\frac{\text{cm}}{\text{sec}}\right) * \text{Surface(cm2)}$$

The coefficient of reflection (reflectance) measures and quantifies protein permeability across membranes. It is one when the membrane is freely permeable to the protein and zero when the membrane is impermeable to protein but still permeable to water. Since the surface of exchange is difficult to determine, the PS product (cm/sec) is best derived from the partition coefficient.

The results of using this method demonstrated that for a low molecular weight protein (less than 40 kD) leaked in the human or animal circulation from a diseased BBB the appearance in saliva vs. arterial blood for these markers is delayed (FIG. 4). However, this delay was negligible and the steady state values for saliva:artery ratios was rapidly achieved (FIG. 5). This demonstrates the feasibility and viability of the present invention's devices and methods of using saliva as a source of brain-derived biomarkers.

Among the different reasons that made the use of brain biomarkers a holy grail for neurology, is the minimally invasive nature of the process required to obtain blood. While typically a venipuncture is required this is clearly less morbid than CSF sampling or use of intravascular contrast agents such as gadolinium or iodinated contrast agents. In addition, imaging modalities such as CT scans expose the patient to radiation. Last, but perhaps not least, is the cost differential between state-of-the-art medical imaging and a simple blood test. However practical a blood draw may be, it is preferred to use saliva as a biomarkers origin, for several reasons including the fact that sampling of saliva is usually economical, safe, easy and can be performed without the help of health care workers, allowing home-based sampling. Saliva contains little interference from other proteins, has virtually no cellular components, clotting or red blood cells, which improves the diagnostic approach because no centrifugation is required. The present invention utilizes considerations related to intrapersonal variability for blood biomarkers can be easily adapted to salivary markers, since the ratio saliva:blood can be estimated or experimentally determined, and an algorithm for such application was developed. While the advantages of peripheral biomarkers are well-understood, their widespread use has been confounded until the present invention by several factors including the intra-individual variability in "control values", the effect of age on markers' presence or levels, ethnic differences, and the like. While a number of groups have attempted to described some of this variability, and while most of the data presented so far focused on the astrocytic protein S100B, until the present invention no one or grouping of such data have painted a clear picture until the present invention. This biomarker (S100B) has been studied for several years, but also investigated as a tool to diagnose a non-CNS condition, mainly malignant melanoma. Other markers are being investigated, and it's very likely that a number of new markers will become available in the next decade. One of the obstacles for a widespread acceptance of this approach to diagnose neurological diseases is the lack of understanding on how levels of biomarkers in serum or plasma are holistically controlled by other bodily functions. For example, it has been suggested that S100B levels directly depend on BMI, but others have suggested that the increased permeability of the BBB in diabetes or conditions associated with obesity are the underlying factors. To address this and other issues, the present invention includes an algorithm that mimics the distribution of these proteins, BBB permeability, excretion, and the like not only for S100B but for a broad range of markers. In addition, the effect of molecular size on the overall bioavailability of a given marker was not only determined but its effect on the quantification of the screening and diagnosis of such neurological conditions was indeed determined.

For the algorithms described herein, the arterial-to-venous transfer of biomarkers was simplified by assuming a homogeneous distribution of the biomarker in all of systemic circulation, and that the volume of this idealized vascular structure was equalized to the total volemia. An additional consideration was made for the cerebral region of blood circulation, where permeability across the blood-brain barrier was incorporated as a governing factor to free diffusion of brain-specific biomarkers. Each marker's blood concentration was set to zero at the beginning of the simulation so that a kinetic progression toward steady-state levels could be observed at t>0, and that the blood-brain barrier permeability factor spanned an arbitrary range of 0 to 100%. This dynamic range theoretically spans from a permeation velocity (cm/s) of zero to a permeation velocity that equals the free diffusion of a given molecule in bodily fluids. This spectrum of values is biologically unrealistic, but was established for convenience. The extent of "opening" for the blood-brain barrier was, however, based on clinical observations, and the kinetic property of molecule extravasation was based on empirical results. While there is obviously a large difference between measurements based on contrast-enhancement versus diffusion of a molecule from brain to blood, this "Radiologic Index" is currently the best comparative approach to model the behavior of a diffusible marker against clinically acceptable means.

Biological markers are present in different CNS compartments. For example, S100B and GFAP are expressed at high levels in astrocytes (but not neurons or other brain cell types) but can also be detected in cerebrospinal fluid (CSF) as well as in interstitial fluid (ISF). Since the dynamic process of intracellular-to-extracellular movement of these markers is currently unknown, clinically available data was used as set points for biomarker "brain levels". In fact, these levels reflect what can be measured in extracellular fluid in normal brain. In spite of this simplification, the approach and modeling allow for replication of the common features of many neurological diseases i.e., gliosis. The latter is a secondary sequela of many acute injuries such as TBI, stroke, etc. During the gliotic process, GFAP and S100B are increased in astrocytes as well as in ISF and CSF.

Data from patients undergoing BBB disruption by osmotic means were used (Kroll, R. A. and Neuwelt, E. A. *Outwitting the blood-brain barrier for therapeutic purposes: osmotic opening and other means* (1998) Neurosurgery 42; 1083-1099; Rapoport, S. I. *Osmotic opening of the blood-brain barrier: principles, mechanism, and therapeutic applications* (2000) Cell Mol. Neurobiol. 20; 217-230; Rapoport, S. I. *Advances in osmotic opening of the blood-brain barrier to enhance CNS chemotherapy* (2001) Expert. Opin. Investig. Drugs 10; 1809-1818) (Kroll, R. A. and Neuwelt, E. A. *Outwitting the blood-brain barrier for therapeutic purposes: osmotic opening and other means* (1998) Neurosurgery 42; 1083-1099; Rapoport, S. I. *Osmotic opening of the blood-brain barrier: principles, mechanism, and therapeutic applications* (2000) Cell Mol. Neurobiol. 20; 217-230; Rapoport, S. I. *Advances in osmotic opening of the blood-brain barrier to enhance CNS chemotherapy* (2001) Expert. Opin. Investig. Drugs 10; 1809-1818) (Kroll, R. A. and Neuwelt, E. A. *Outwitting the blood-brain barrier for therapeutic purposes: osmotic opening and other means* (1998) Neurosurgery 42; 1083-1099; Rapoport, S. I. *Osmotic opening of the blood-brain barrier: principles, mechanism, and therapeutic applications* (2000) Cell Mol. Neurobiol. 20; 217-230; Rapoport, S. I. *Advances in osmotic opening of the blood-brain barrier to enhance CNS chemotherapy* (2001) 10; 1809-1818) to determine the rate of S100B increase in blood, both of which are herein incorporated by reference. The time-dependent data corresponding to the sudden increase in S100B for these patients was fitted to:

$$[S100B]_{serum}=0.29-0.20*0.79^{time}$$

where time is expressed in minutes after the osmotic shock.

Validation of "goodness of BBB opening" was performed, in brief, by setting optimal, maximal osmotic and hemispheric BBB disruption to 100% while no effect of BBBD was computed as 0%. S100B was measured at time of imaging by contrast CT and plotted as the difference between post- and pre-disruption S100B values in serum. In the model, the time-dependent change in BBB permeability was expressed according to Equation 1 and resulting change in blood S100B after BBB permeability changes according to Equation 2. It was assumed in the simulation that a steady-state, physiological "leak" of S100B across a healthy BBB as 1-5% of maximal possible hemispheric disruption:

$$\Delta[S100B]_{serum}=0.0022*[\text{Radiologic index}]$$

The relationship between molecular size of a brain biomarker and its propensity to be filtered by the kidneys, referred to herein as the Filtration Coefficient ($C_F$), was based on:

$$C_F=(-0.04094+(1.19614)/(1+10\hat{}((27096-\text{molecular weight})*-3.1E-5)))$$

where the value of $C_F$ falls between 0 (no filtration) and 1.0 (complete filtration). Empirical data were used to create this fitted equation which was further refined by Cockcroft-Gault estimate of glomerular filtration (GFR).

The algorithm encompasses several features of human physiology that are age-and-biomarker-dependent, and therefore the effects of age on serum values for markers of varying molecular weight were analyzed. Data on UCHL-1 and GFAP in healthy newborns were not available, so instead S100B values which decrease from an average of 0.9 ng/ml to 0.3 ng/ml in the first postnatal months and further decrease to 0.11 ng/ml in adolescence were used (Bouvier, D., Duret, T., Rouzaire, P., Jabaudon, M., Rouzaire, M., Nourrisson, C., Bourgne, C., Pereira, B., Evrard, B., and Sapin, V. *Preanalytical, analytical, gestational and pediatric aspects of the S100B immuno-assays* (2016) Clin. Chem. Lab Med. 54; 833-842) (Bouvier, D., Duret, T., Rouzaire, P., Jabaudon, M., Rouzaire, M., Nourrisson, C., Bourgne, C., Pereira, B., Evrard, B., and Sapin, V. *Preanalytical, analytical, gestational and pediatric aspects of the S100B immuno-assays* (2016) Clin. Chem. Lab Med. 54; 833-842)(Bouvier, D., Duret, T., Rouzaire, P., Jabaudon, M., Rouzaire, M., Nourrisson, C., Bourgne, C., Pereira, B., Evrard, B., and Sapin, V. *Preanalytical, analytical, gestational and pediatric aspects of the S100B immuno-assays* (2016) Clin. Chem. Lab Med. 54; 833-842) (Bouvier, D., Duret, T., Rouzaire, P., Jabaudon, M., Rouzaire, M., Nourrisson, C., Bourgne, C., Pereira, B., Evrard, B., and Sapin, V. *Preanalytical, analytical, gestational and pediatric aspects of the S100B immuno-assays* (2016) Clin. Chem. Lab Med. 54; 833-842), all of which are incorporated by reference. For healthy adults, S100B levels in serum are below 0.1 ng/ml. Of the physiological variables that may contribute to different biomarker concentrations between newborns and adults, three possible, non-mutually exclusive factors were focused on: 1) Glomerular filtration rate (GFR) is significantly lower in the neonatal stage of development, and does not reach fully mature levels until after infancy; 2) Body size, and specifically the ratio of brain volume to volemia/body weight, is dramatically different in babies; and 3) Homeostatic BBB function may differ post-gestation compared to adulthood. This algorithm also incorporated reference values for both neonatal and adult GFR. The simulation was run as follows: initially a level of zero for serum biomarker and observed the reaching of a steady-state based on age-specific variables was used. After steady-state was established, a maximal BBB disruption (BBBD) was simulated, which persisted for 1-2 hours before leakage rates returned to homeostatic levels. Serum biomarker levels decreased to steady-state at a rate dependent upon kidney function and the properties of the biomarker. The simulation was ended after 24 hours. Note that newborn steady-state levels of S100B prior to BBBD were significantly elevated compared to that of a healthy adult. Similarly, the extent of the maximal BBBD-induced serum increase for S100B was exaggerated in the newborn. There was a strong correlation between experimental results and output of the algorithm.

Since one goal of the algorithm was to include other markers, a variable that takes into account protein excretion at a given GFR for different molecular weights was added. Equation 3 shows the algorithm relationship used to extrapolate kidney filtration vs. molecular weight. An increased molecular weight resulted in pronounced increases in clearance time, which translated into longer persistence of the signals. In adults, similar results were obtained. Although neonates and adults were modeled using physiological values for body size and kidney function, the initial concentration of brain markers in adults was set equal to neonates. These results emphasize how age-related differences in homeostatic and post-BBBD serum levels of each marker may be explained by anatomic (e.g., brain volume) or physiologic (steady-state BBB permeability) variations.

This algorithm also predicted minimal physiological changes in serum biomarker levels between an adult male and female. This is consistent with actual results with S100B showing no gender-specific variations in steady-state levels. Although the Cockcroft-Gault formula for estimating glomerular filtration rate provides a lower level of protein elimination for females than males, rate of contribution by the brain is also decreased due to a smaller brain-to-blood volumetric ratio. This deviation from the physiology of the adult male resulted in a slightly varied kinetic curve due to reduced clearance removal of biomarkers from serum of the female subjects. This slight difference predicted by the algorithm is not clinically relevant as a gender-driven difference has not been reported.

Recent literature has demonstrated a clinically relevant difference in serum S100B levels based on race and regional/seasonal variance, where individuals of a darker complexion or African-American descent have been reported to have steady-state levels nearly twice as high as individuals of lighter complexion or Caucasian descent. Specifically, it was initially believed that ethnicity is the main driving factor for elevated S100B in African-American subject. If this were the case, based on available GFR data, our algorithm would predict a lower biomarker level due to its increased clearance. Since this is obviously not the true reason for the observed differences, a skin compartment was added to the algorithm to reproduce on the one hand a steady-state contribution of dermal tissue to S100B levels while on the other hand, allowing to "titrate" S100B levels to a broad range of values. This was done to test the hypothesis that sun exposure is sufficient to account for the differences originally attributed to ethnic factors. An obvious limitation of this approach is that one needs to input a value for S100B concentrations in skin or any other organ contributing to serum levels. Therefore, levels of S100B were measured by ELISA in freshly resected surgical samples from normal access tissue and these values were added to an appropriate (matched to average body size of a given subject) volume of skin. Only adult males were considered for this portion of the study but the algorithm can encompass a broad range of ages or body size/ethnicity. The results confirmed that when using the measured values of skin [S100B] and the appropriate volumetric ratios, the algorithm accurately predicted increases in serum S100B based only on skin pigmentation but not to race. The algorithm predicts that a range of S100B values can be found in any ethic group and that these differences depend primarily on S100B released by skin and not on genetic factors. Changes in BBBD-induced S100B were minimally effected. This is to be expected given that BBBD only affects cerebral vasculature permeability.

The data demonstrated that one of the chief regulators of the markers' levels in blood (and therefore in saliva) is the presence or absence of normal GFR. It also showed that kidney function (both physiologic and pathologic) affects markers' half-life in a size-dependent manner. In other words, with physiologic kidney function, half-life was linearly related to markers' molecular size. However, when approaching kidney failure, the effect was overwhelmingly shifted toward markers with 40 kD molecular weight. This is important because markers of brain and BBB damage can be very small (S100B, 10 kD), of intermediate size (tau, 46 kD), or large (autoreactive IgGs, 140 kD). It is thus important to underscore that without adjusting for molecular weight and kidney function, one may misinterpret the true clinical meaning of a given marker. For example, if one wishes to determine the delayed sequelae of a given event (e.g., stroke, TBI) it is best to use a marker with a longer half-life (higher molecular weight).

Another aspect that should be underscored is the use of accepted values for the markers' initial assignments in the brain. The relative changes in brain-to-blood volume due to changes in age and gender were also modeled, as well as extracranial sources of a given marker. In the case of S100B, it is widely reported that skin and fat contain substantial levels of S100B. The algorithm used measured values for fat and skin S100B content. By doing so, the algorithm showed that skin levels directly affect steady-state serum S100B levels, and what is more important, they also reproduce changes in basal S100B levels due to ethnicity, exposure to sun and skin complexion. Real data was used to confirm or disprove the output of the algorithm. Fat tissue, when measured in abroad range of BMI, did not influence blood S100B. This may be surprising since the measured levels of S100B in skin were in fact lower than levels in fat. This discrepancy can be explained by two mechanisms, namely the high cellular turnover and death rate of dermal cells and the poor vascularization of adipose tissue compared to dermis.

The present invention is based on monitoring or measuring a marker or markers of BBB and its permeability. One example of such a marker is S100B which is synthesized primarily in the brain by astrocytes and is released from the brain into the blood when the BBB is disrupted. S100B has also been found in other tissues, but at much lower concentrations, and although S100B in blood typically indicates disruption of the BBB, S100B has also been shown to increase in blood, plasma, CSF resulting from other pathologies not limited to the CNS. S100B may be indicative of brain damage or advanced metastasis in melanoma patients, for example. The present invention, in its various embodiments, provides systems, devices and methods for diagnostic and prognostic evaluation of the permeability of the BBB.

Blood S100B directly correlates with the serum-albumin quotient (QA) due to the QA's measurements of the integrity of the blood brain barrier (BBB). S100B also correlates with radiological indices of BBB disruption. When the BBB is caused to open, such as through injury, proteins that are predominantly present in the central nervous system (CNS), for example UCHL-1, GFAP and S100B, are able to diffuse through the BBB into the patient's blood. Thus, where a spinal tap and a blood sample are both required in order to measure the QA—requiring both measures of the concentration of albumin in the blood as well as the cerebral spinal fluid (CSF), S100B levels can be measured in saliva with a much less invasive and intensive process, simply by taking a salivary sample and measuring for the concentration of S100B. If S100B levels are elevated in the saliva, then there is a high likelihood that the BBB integrity has been compromised. Work by others investigated the presence of S100B in saliva. A reference curve of the protein in this biological fluid in normal preterm and term newborns was also established. (Gazzolo, D., Lituania, M., Bruschettini, M., Ciotti, S., Sacchi, R., Serra, G., Calevo, M. G., Corvino, V., Buonocore, G., and Michetti, F. *S100B protein levels in saliva: correlation with gestational age in normal term and preterm newborns* (2005) Clin Biochem. 38; 229-233). Salivary S100B was also measured in adults (Traxdorf, M., Wendler, O., Tziridis, K., Bauer, J., and Scherl, C. *S100B in serum and saliva: a valid invasive or non-invasive biomarker in obstructive sleep apnea*? (2016) Eur. Rev. Med. Pharmacol. Sci. 20; 4766-4774). These results have demonstrated the excellent correlation between the algorithm proposed by us (see above) and experimental data. The above references are herein incorporated by reference.

S100B, therefore, is an excellent marker useful for providing a negative predictive indication for sequelae of BBB disruption or TBI—a simple saliva sample tested for S100B yielding low or non-elevated levels of the protein provides a good negative indication that the BBB has not been disrupted and there is little or no injury to the patient's brain, even if elevated levels may not be a specific positive predictor of such injuries or conditions. Conversely, other markers measured in blood or saliva may be used in a similar manner for providing positive predictive values for BBB disruption and/or TBI, for example serum levels of the marker UCHL-1 where a significant increase of serum UHCL-1 is directly correlated with the presence of TBI. Various embodiments of the present invention can be adapted to provide analysis of different proteins or markers in saliva for either negative prediction or positive prediction of BBB integrity or the presence of TBI. With specific respect to S100B, measurement of the protein in saliva will provide and accurate prediction of normal CT results, thus indicating either presence of a minor injury or lack of injury. Thus, when saliva, blood or serum levels of S100B are low, it can be determined to be safe to omit further imaging tests, such as CT or MRI in order to avoid unnecessary testing and expense.

Saliva is mostly composed of water, but food particles or floating cells may also be present. This implies that a filtration step may be under some conditions desirable before testing for the presence of analytes. This can be achieved a number of embodiments one optionally being by use of a hollow fiber inlet where passage from lumen to testing chamber is restricted to <0.5 micrometers. Fluid can be pushed through the fiber manually, where the operator exerts a positive pressure to facilitate the process or by applying negative pressure in the recording chamber.

In order to most accurately predict normal CT results indicating very minor injury or no injury, measurement an analysis of the patient's saliva S100B levels should be performed rapidly and as close in time to the potential injurious event as possible. Preferably, S100B levels in a patient's saliva are measured within 8 hours of injury. More preferably, S100B levels in a patient's saliva are measured within 6 hours of injury. Still more preferably, S100B levels in a patient's saliva are measured within 4 hours of injury. Yet more preferably, S100B levels in a patient's saliva are measured within 3 hours of injury. Even more preferably, S100B levels in a patient's saliva are measured within 2.5 hours of injury. Still yet more preferably, S100B levels in a patient's saliva are measured within 2 hours of injury. Yet even more preferably, S100B levels in a patient's saliva are measured within 1.5 hours of injury. Even still more preferably, S100B levels in a patient's saliva are measured within 1 hours of injury. Yet still more preferably, S100B levels in a patient's saliva are measured within 45 minutes of injury. Even yet more preferably, S100B levels in a patient's saliva are measured within 30 minutes of injury. Still even more preferably, S100B levels in a patient's saliva are measured within 15 minutes of injury. Most preferably, S100B levels in a patient's saliva are measured within 10 minutes of injury.

With respect to measurements of markers, the terms "above normal" and "above threshold" refer to a level of the given marker (e.g., S100B) that is greater than the level of the marker observed in normal individuals and when taking demographic variables and a given environment into account, that is, individuals who are not undergoing an event or suffering from an injury such as TBI and/or BBB disruption, or opening of any other blood-brain or CSF-blood barriers. These terms refer to a level of the marker that is statistically significantly above the normal level. The assay method by which the analysis for the marker is carried out must be sufficiently sensitive to be able to detect the level of the marker which is present over the concentration range of interest and also is preferably specific to that marker. S100B levels measured in the patient's saliva can readily be determined to be normal or elevated based on the assayed salivary sample. However, normal values are determined by many factors, including demographic information such as age and race or ethnicity. If, given the various demographic factors of a specific patient, salivary S100B is elevated enough, further testing can be performed to determine whether TBI is present, or the BBB is disrupted, using the more intensive, expensive and cumbersome tests including CT or QA measurement. Preferably, additional testing is not performed unless salivary S100B levels reach a certain level. The determination for performing further testing for TBI can be made based on many measurements or values related to S100B, including, but not limited to, raw measured salivary S100B levels or percentage increase of salivary S100B levels above normal. It is important that the demographic effects be taken into consideration, however. An S100B saliva value of 0.005 ng/ml may be abnormal for one person but may be perfectly normal for another person, depending on age, race, etc. Generally, however, preferably a saliva S100B concentration of 0.003 ng/ml or less is considered negative for TBI or BBB disruption. More preferably, a saliva S100B concentration of 0.005 ng/ml or less is considered negative for TBI or BBB disruption. Still more preferably, a saliva S100B concentration of 0.007 ng/ml or less is considered negative for TBI or BBB disruption. Yet more preferably, a saliva S100B concentration of 0.009 ng/ml or less is considered negative for TBI or BBB disruption. Even more preferably, a saliva S100B concentration of 0.01 ng/ml or less is considered negative for TBI or BBB disruption. Still yet more preferably, a saliva S100B concentration of 0.015 ng/ml or less is considered negative for TBI or BBB disruption. Yet even more preferably, a saliva S100B concentration of 0.02 ng/ml or less is considered negative for TBI or BBB disruption. Even still more preferably, a saliva S100B concentration of 0.05 ng/ml or less is considered negative for TBI or BBB disruption. Yet still more preferably, a saliva S100B concentration of 0.07 ng/ml or less is considered negative for TBI or BBB disruption. Most preferably, a saliva S100B concentration of less than 0.1 ng/ml is considered negative for TBI or BBB disruption. Thus, it can be said that if the system of the present invention measures saliva S100B levels to be 0.1 ng/ml or greater, and in the patient is a light skinned average size adult male, that the patient is not showing a negative indication for the presence of TBI or BBB disruption, and that the patient may benefit from undergoing further testing to provide a positive diagnosis of TBI and/or BBB disruption. Thus, the present invention's negative prediction capabilities can help avoid unnecessary testing and expense while still allowing for such measures to be taken when appropriate.

Given the differences between patients and the various demographic and other factors that affect normal S100B levels, and the variation between types of tests, it may be difficult to determine whether the patient is positive or negative based merely on a measure of salivary concentration of S100B. Therefore, it may be preferable to base a determination of positive or negative results for TBI and/or BBB disruption on changes in the particular patient's levels of salivary S100B, which can be compared to known normal or TBI populations. Generally, a very large percentage of normal patients exhibits a very low saliva S100B measurement, therefore, if a patient's measured saliva S100B concentration is compared to a normal distribution, it can be determined if the subject is likely to be exhibiting a higher level of saliva S100B than normal, and thus be more likely to have suffered TBI and/or BBB disruption. Preferably, in order to make a negative TBI and/or BBB disruption determination, the patient's measured saliva S100B concentration is in the 75$^{th}$ percentile or less compared to a normal population. More preferably, in order to make a negative TBI and/or BBB disruption determination, the patient's measured saliva S100B concentration is in the 60$^{th}$ percentile or less compared to a normal population. Still more preferably, in order to make a negative TBI and/or BBB disruption determination, the patient's measured saliva S100B concentration is in the 45$^{th}$ percentile or less compared to a normal population. Yet more preferably, in order to make a negative TBI and/or BBB disruption determination, the patient's measured saliva S100B concentration is in the 30$^{th}$ percentile or less compared to a normal population. Even more preferably, in order to make a negative TBI and/or BBB disruption determination, the patient's measured saliva S100B concentration is in the 20$^{th}$ percentile or less compared to a normal population. Still yet more preferably, in order to make a negative TBI and/or BBB disruption determination, the patient's measured saliva S100B concentration is in the 10$^{th}$ percentile or less compared to a normal population. Yet even more preferably, in order to make a negative TBI and/or BBB disruption determination, the patient's measured saliva S100B concentration is in the 5$^{th}$ percentile or less compared to a normal population. Logically, in order to make a positive determination of the likelihood of TBI and/or BBB disruption, the converse of these measurements would be true, such that a positive determination could be made if the patient's saliva S100B concentration is in the 75$^{th}$, 80$^{th}$, 85$^{th}$, 90$^{th}$, 92$^{nd}$, 94$^{th}$ or 95$^{th}$ percentile or greater.

Yet another measurement that could be used is the standard deviation of saliva S100B concentration compared to a normal population. When the standard deviation is used, preferably, in order to make a negative determination of the likelihood of TBI and/or BBB disruption, the patient's saliva S100B concentration is greater than 2 standard deviations from a normal population. More preferably, in order to make a negative determination of the likelihood of TBI and/or BBB disruption, the patient's saliva S100B concentration is greater than 1.75 standard deviations from a normal population. Yet more preferably, in order to make a negative determination of the likelihood of TBI and/or BBB disruption, the patient's saliva S100B concentration is greater than 1.5 standard deviations from a normal population. Still more preferably, in order to make a negative determination of the likelihood of TBI and/or BBB disruption, the patient's saliva S100B concentration is greater than 1.25 standard deviations from a normal population. Even more preferably, in order to make a negative determination of the likelihood of TBI and/or BBB disruption, the patient's saliva S100B concentration is greater than 1 standard deviation from a normal population. Still yet more preferably, in order to make a negative determination of the likelihood of TBI and/or BBB disruption, the patient's saliva S100B concentration is greater than 0.8 standard deviations from a normal population. Yet even more preferably, in order to make a negative determination of the likelihood of TBI and/or BBB disruption, the patient's saliva S100B concentration is greater than 0.5 standard deviations from a normal population. Even still more preferably, in order to make a negative determination of the likelihood of TBI and/or BBB disruption, the patient's saliva S100B concentration is greater than 0.5 standard deviations from a normal population. Similar to above, logically, in order to make a positive determination of the likelihood of TBI and/or BBB disruption, the converse of these measurements would be true, such that a positive determination could be made if the patient's saliva S100B concentration is less than 0.5, 0.6, 0.8, 1, 1.25, 1.5, 1.75 or 2 standard deviations from a normal population.

Alternatively, the increase in saliva S100B levels can be measured in terms of a percentage increase compared to normal levels for the patient in order to make the determination of whether the patient is negative for TBI and/or BBB disruption. Preferably, an increase in saliva S100B levels of 1% or less is considered negative for TBI and/or BBB disruption. More preferably, an increase in saliva S100B levels of 2% or less is considered negative for TBI and/or BBB disruption. Still more preferably, an increase in saliva S100B levels of 3% or less is considered negative for TBI and/or BBB disruption. Yet more preferably, an increase in saliva S100B levels of 5% or less is considered negative for TBI and/or BBB disruption. Even more preferably, an increase in saliva S100B levels of 7% or less is considered negative for TBI and/or BBB disruption. Most preferably, an increase in saliva S100B levels of less than 10% is considered negative for TBI and/or BBB disruption. If saliva S100B levels increase by a high enough percentage, then the test cannot be considered negative for TBI and/or BBB disruption and further testing can be scheduled to try and ascertain whether a positive diagnosis can be made.

Preferably, the system operates in real-time. By real-time, it is meant that the system can preferably be used to obtain a determination within close temporal proximity to the time at which the injury occurs and the systems is employed; more specifically, real-time relates to the time in which the system can provide an indication of the level or increase of saliva S100B or other marker concentration from the time at which a blood or other fluid sample is taken. Preferably, the system can provide an indication of the level or increase of saliva S100B or other marker concentration within 30 minutes of taking a salivary or body fluid sample. More preferably, the system can provide an indication of the level or increase of saliva S100B or other marker concentration within 25 minutes of taking a saliva or other body fluid sample. Yet more preferably, the system can provide an indication of the level or increase of saliva S100B or other marker concentration within 20 minutes of taking a saliva or other body fluid sample. Still more preferably, the system can provide an indication of the level or increase of saliva S100B or other marker concentration within 15 minutes of taking a saliva or other body fluid sample. Even more preferably, the system can provide an indication of the level or increase of saliva S100B or other marker concentration within 10 minutes of taking a saliva or other body fluid sample. Still yet more preferably, the system can provide an indication of the level or increase of saliva S100B or other marker concentration within 5 minutes of taking a saliva or other body fluid sample. Even still more preferably, the system can provide an indication of the level or increase of saliva S100B or other marker concentration within 4 minutes of taking a saliva or other body fluid sample. Still yet more preferably, the system can provide an indication of the level or increase of saliva S100B or other marker concentration within 3 minutes of taking a saliva or other body fluid sample. Even yet more preferably, the system can provide an indication of the level or increase of saliva S100B or other marker concentration within 2 minutes of taking a saliva or other body fluid sample. Yet even more preferably, the system can provide an indication of the level or increase of saliva S100B or other marker concentration within 1 minute of taking a saliva or other body fluid sample. Still even more preferably, the system can provide an indication of the level or increase of saliva S100B or other marker concentration within 25 minutes of taking a saliva or other body fluid sample. Even still yet more preferably, the system can provide an indication of the level or increase of saliva S100B or other marker concentration within 30 seconds of taking a saliva or other body fluid sample. Still yet even more preferably, the system can provide an indication of the level or increase of saliva S100B or other marker concentration within 15 seconds of taking a saliva or other body fluid sample. Yet even still more preferably, the system can provide an indication of the level or increase of saliva S100B or other marker concentration within 10 seconds of taking a saliva or other body fluid sample. Yet still even more preferably, the system can provide an indication of the level or increase of saliva S100B or other marker concentration within 5 seconds of taking a saliva or other body fluid sample. Still even yet more preferably, the system can provide an indication of the level or increase of saliva S100B or other marker concentration within 1 second of taking a saliva or other body fluid sample. Most preferably, the system can provide an indication of the level or increase of saliva S100B or other marker concentration substantially instantaneously after a saliva or other body fluid sample is taken and applied to the system.

Many system and/or device embodiments of the present invention are intended for point of care (POC) application. That is, the systems and/or devices are designed to be portable, easy to carry and store, easy to carry and deploy such that they can be kept ready or be otherwise readily available for deployment quickly, easily, and without large equipment or resources required. For example, the systems and/or devices of POC embodiments are intended to be used readily as soon after an injury occurs as possible, at the point or near to the point where the injury occurred such that the patient does not to be moved long distances in order to use the system and/or device or to have the system and/or device used on them—such as on the sports field or at the scene of a car accident, by way of two non-limiting examples. Preferably the POC system and/or device is easily storable and can be carried and/or stored on or near a person for ready deployment, such as in a carrying case, a medical bag, a purse, or perhaps even in a pocket. Point-of-care diagnostics are tests that do not involve the use of laboratory staff and facilities to provide the result. This is a crucial problem in diagnostic of concussions or head injury. The analytical "targets" include proteins, nucleic acids, metabolites, drugs, dissolved ions and gases, human cells, and microbes. Samples are blood, saliva, urine, or other bodily fluids or (semi)solids. Whether used "near patient" in a hospital, clinic, or doctor's office, or administered at home to maintain health, manage disease, or monitor therapy, or in the field to test the safety of water, food, or compliance with laws and regulations, these tests accept a sample with little or no pre-preparation and provide a result, the "answer", in seconds to hours. Ideally, these tests require only elementary instruction to use. Interpretation may be as simple as viewing a stripe or spot of color on a strip of paper or polymer; increasingly, however, readers ranging from hand-held devices to benchtop instruments read the analytical test, provide a comprehensible result, and if necessary, control and operate the sample-containing platform that executes the analytical process.

Preferably the present invention utilizes saliva as the bodily fluid as described above in the Summary of the Invention. In additional and optionally preferably the saliva osmolality is indexed or the samples used on normalized depending on the state or level of hydration of the subject being tested. One optional technique for determining osmolality is described in U.S. Pat. Nos. 8,349,610 and 8,426,207, which are incorporated by reference. Other techniques measuring the flow or the viscosity of the saliva may also be used to index or normalize the saliva used for the state of hydration of the subject. These steps can be used with the POC device and an additional well and/or additional sensors may be used to provide such measurement.

These devices have several obstacles to overcome, for example POC: 1) are challenged by small sample volumes (hundreds of nanoliters to 1 mL) of complex biological media with femtomolar to millimolar concentrations of analytes; 2) should be inexpensive disposable chips or cartridges that include microfluidic features to provide or control sample preparation, flow rate, mixing with reagents, reaction time associated with binding events, filtration of non-analytical components of the sample, separation of interfering agents and of multiple analytes, and an effective measurement capability; 3) POC diagnostic cost parameters differ from those of conventional laboratory analysis. Readers (instruments) are smaller and more specialized than laboratory systems, so they cost less but do only one or a few different tests. Samples do not directly contact the reader; hence self-cleaning subsystems are not needed. The POC chip, strip, or cartridge, a consumable that contains the sample but is not designed for cleaning or reuse, may include fluidics, on-board reagents and dyes, optics, electrodes, even thermal control. Relative to a blood-draw tube, the POC device's greater complexity and functionality make it costlier, so tests sold in large volume derive most of their revenue from the consumable.

Advantages of POC are equally impressive, for example: 1) Home testing: In-home POC testing reduces the frequency of hospital visits, travel expenses, and lost work time. The success of glucose meters and pregnancy tests has motivated more people to opt for self-testing, conferring increased responsibility to maintain their own medical records and notify their physicians should abnormal results arise. Empowering individuals to do their own tests can improve patient compliance (adherence to diagnosis and treatment regimens); 2) POC tests can indirectly, sometimes drastically, lower medical costs: sample mislabeling and mishandling, along with misdirection of results, are less likely. Results are provided more quickly, enabling more effective treatment of rapidly progressing afflictions. Rapid POC results can obviate hospital admissions, e.g., when a suspected myocardial infarct is determined rapidly to be indigestion; 3) Indirect cost savings are also related to and consequence of decreased reliance of other diagnostic means, for example MR and CT imaging. Specifically, in the case of POC for TBI as described in the present proposal, CT scans are routinely administered to all head injury victims, but most are negative adding costs that may be avoided if a rapid POC alternative were used. This has been underscored in a European study; 4) Another indirect advantage of rapid POC for head injury is the avoidance of exposure to potentially harmful X rays used during CT scans. For example, for a routine head CT scan it was estimated one in 8,100 women 40 years of age at the time of the scan (or one in 11,080 men) would develop cancer. The risks were projected to double for 20-year-old patients; for 60-year-old patients the risks were about 50 percent lower (see for example, in the context of TBI).

Preferably, POC embodiments utilize a system or device that is less than 100 $in^3$ in total volume. More preferably, POC embodiments utilize a system or device that is less than 90 $in^3$ in total volume. Still more preferably, POC embodiments utilize a system or device that is less than 80 $in^3$ in total volume. Yet more preferably, POC embodiments utilize a system or device that is less than 70 $in^3$ in total volume. Even more preferably, POC embodiments utilize a system or device that is less than 60 $in^3$ in total volume. Still yet more preferably, POC embodiments utilize a system or device that is less than 50 $in^3$ in total volume. Yet even more preferably, POC embodiments utilize a system or device that is less than 40 $in^3$ in total volume. Even still more preferably, POC embodiments utilize a system or device that is less than 30 $in^3$ in total volume. Yet still more preferably, POC embodiments utilize a system or device that is less than 20 $in^3$ in total volume. Still even more preferably, POC embodiments utilize a system or device that is less than 10 $in^3$ in total volume. Even yet more preferably, POC embodiments utilize a system or device that is less than 5 $in^3$ in total volume. Yet still even more preferably, POC embodiments utilize a system or device that is less than 4 $in^3$ in total volume. Still even yet more preferably, POC embodiments utilize a system or device that is less than 3 $in^3$ in total volume. Even yet still more preferably, POC embodiments utilize a system or device that is less than 2 $in^3$ in total volume. Still yet even more preferably, POC embodiments utilize a system or device that is less than 1 $in^3$ in total volume.

Similarly, again, the system and/or device of POC embodiments should be preferably lightweight and easy to carry and deploy. Preferably, POC embodiments utilize a system or device that weighs less than 10 lbs. More preferably, POC embodiments utilize a system or device that weighs less than 9 lbs. Still more preferably, POC embodiments utilize a system or device that weighs less than 8 lbs. Yet more preferably, POC embodiments utilize a system or device that weighs less than 7 lbs. Even more preferably, POC embodiments utilize a system or device that weighs less than 6 lbs. Still yet more preferably, POC embodiments utilize a system or device that weighs less than 5 lbs. Yet even more preferably, POC embodiments utilize a system or device that weighs less than 4 lbs. Even still more preferably, POC embodiments utilize a system or device that weighs less than 3 lbs. Yet still more preferably, POC embodiments utilize a system or device that weighs less than 2 lbs. Still even more preferably, POC embodiments utilize a system or device that weighs less than 1 lb. Even yet more preferably, POC embodiments utilize a system or device that weighs less than 12 oz. Still yet more preferably, POC embodiments utilize a system or device that weighs less than 8 oz. Yet even still more preferably, POC embodiments utilize a system or device that weighs less than 4 oz.

The system, however, need not comprise a portable and/or POC device. Some embodiments of the present invention may utilize a larger scale or permanent assay system or device such as those located in hospitals or laboratory settings.

The system and methods of the present invention may utilize immunoassay techniques known in the art, including enzyme-specific immunosorbent assay (ELISA) techniques. ELISA systems and methods are powerful in detecting and quantifying a specific analyte in a complex mixture. It is well established that among immunoassay methods, enzyme-linked immunosorbent assay (ELISA) is the most frequently applied. ELISA is a powerful method for detecting and quantifying a specific analyte in a complex mixture. This immunoassay technique has revolutionized immunology and is commonly used in medical research laboratories and commercial applications. However, the current needs in the (bio)chemical analytical field demands the development of more fast, sensitive, high-throughput and point of care analysis. Screen-printed arrays of eight wells up to 96-well plates have been developed, enhancing the potentialities of the use of disposable electrodes and becoming high-throughput attractive analytical platforms. The use of printed electrodes as means for point of care diagnostics has also been explored.

The present invention, however, is directed to even faster systems and methods with higher sensitivity, increased throughput, and most importantly, point of care analysis rather than typical assays which require laboratory staff, techniques and equipment. The point of care systems and methods of the present invention seek to analyze target compounds such as proteins, nucleic acids, metabolites, drugs, dissolved ions and gases, human cells, microbes and the like from samples of blood, saliva, urine or other body fluids, solids or semi-solids. The point of care systems and methods of the present invention preferably are designed to accept samples with little or no pre-preparation and to provide a result in real-time as defined herein, requiring little or no training or instruction to use. Results may be displayed in any form that readily indicates to the viewer valuable information regarding the test results and/or their meaning. For example, the system may merely use a strip of paper or polymer that displays a stripe or spot or otherwise changes color in order to indicate results. Other embodiments may utilize reusable systems with digital or analog displays capable of displaying actual measured values, calculated indexes based on the measured values, signals or warnings based on measured values or other more robust information.

The various embodiments of the present invention can be used to identify patients at risk for developing a disease associated with increased permeability of the blood-brain barrier, as well as to provide insight on the ability of an agent or agents to pass the blood-brain barrier.

The various embodiments of the present invention are intended for use in any setting where injury, particular injury to a person's head, neck or central nervous system, may occur. Such injuries are the type that may cause a disruption in the BBB and/or mTBI or TBI. Such injuries may occur in the course of athletic performances at any level, professional, amateur or personal hobby or fitness, work place or employment settings, recreational activities, or in settings of everyday life where concussive injuries may occur. Examples of athletic performance where the present invention may be useful include, but are not limited to, professional sports competitions such as football, soccer, baseball, hockey, basketball, Olympic competitions and the like, or practice or training activities for such activities. Examples of workplace or employment settings where the present invention may be used include any work setting where concussive injuries may occur as a course of performing one's occupation, such as construction or other occupations requiring regular physical labor or activity, or any other workplace environment where a person may encounter a concussive injury such as by falling debris or items or even slip and fall injuries, and the like. Everyday life settings where the present invention may be used similarly include any setting where a person may encounter a concussive injury by falling objects or by falling themselves. Other instances of everyday life concussive injuries may include anything from falling from a tree, hitting one's head on a door or door frame, automobile accidents, accidental blows to the head, physical altercations with other individuals or animals, or any other such occurrence.

At least one embodiment of the present invention can be used to identify whether or not a patient has undergone an event that by affecting blood-brain barrier integrity may also impact brain health.

Embodiments of the present invention preferably involve the use of patient-derived blood samples to determine the occurrence and level of circulating proteins indicative of blood-brain barrier permeability or integrity.

In one embodiment, the present invention is a method of diagnosing blood-brain barrier permeability markers comprising the steps of (a) taking a biological fluid sample from a patient; (b) determining a plurality of patient-specific properties and medical history via a questionnaire, observation (e.g., gender, race/ethnicity, or the like), or measures (e.g., height, weight, and the like); (c) entering the patient-specific properties into the POC assay device or a separate device such as a computer, tablet, cell or smart phone or the like of a blood-brain barrier permeability marker test system; (d) analyzing, with an analyzer component of the blood-brain barrier permeability marker test system, the content in the biological fluid sample of at least one blood-brain barrier permeability marker to arrive at an unadjusted value of marker content for each tested marker; (e) processing, based at least in part on the entered patient-specific properties, the unadjusted value of the marker content to arrive at an adjusted value indicative of the level of blood-brain barrier disruption; and (g) determining, based at least in part on the level of blood-brain barrier disruption, a level of diseased state of the patient.

In another embodiment, the present invention is a method of diagnosing blood-brain barrier permeability markers comprising the steps of (a) taking a biological fluid sample from a patient; (b) determining a plurality of patient-specific properties via a questionnaire; (c) entering the patient-specific properties into a computer system of a blood-brain barrier permeability marker test system; (d) analyzing, with an analyzer component of the blood-brain barrier permeability marker test system, the content in the biological fluid sample of at least one blood-brain barrier permeability marker to arrive at an unadjusted value of marker content for each tested marker; (e) analyzing the biological fluid sample to arrive at sample-specific properties; (f) processing, based at least in part on the entered patient-specific properties and the determined sample-specific properties, the unadjusted value of the marker content to arrive at an adjusted value indicative of the level of blood-brain barrier disruption; and (g) determining, based at least in part on the level of blood-brain barrier disruption, a level of diseased state of the patient.

Still another embodiment of the present invention includes an assay device for determining a likelihood that a subject has a neurological condition or to assess brain health comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one binding agent adapted to elicit a chemical reaction and bind to a target marker in the blood or other body fluid sample; at least one sensor having a signal and adapted to measure an electrical current output from the chemical reaction, and being disposed in or about the at least one assay chamber; a processor comprising an algorithm, the processor adapted to process the signal from the at least one sensor and the processor and algorithm adapted to output a determination based at least in part on the signal from the at least one sensor, the determination being a likelihood that the subject has a neurological condition or an assessment of brain health of the subject; and an output device adapted to display or indicate at least the determination.

Yet another embodiment of the present invention includes an assay device for determining a likelihood that a subject has a neurological condition or to assess brain health comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one binding agent adapted to elicit a chemical reaction and bind to a target marker in the blood or other body fluid sample; one or more sensors each having a signal, the one or more sensors each adapted to measure an electrical current output and/or a chemiluminescent output from the chemical reaction, and each sensor being disposed in or about the at least one assay chamber; a processor comprising an algorithm, the processor adapted to process the signals from the one or more sensors and the processor and algorithm adapted to output a determination based at least in part on the signals from the one or more sensors, the determination being a likelihood that the subject has a neurological condition or an assessment of brain health of the subject; and an output device adapted to display or indicate at least the determination.

Even another embodiment of the present invention includes an assay device for determining a likelihood that a subject has a neurological condition or to assess brain health comprising: an inlet adapted to receive a blood or other body fluid sample taken from a subject; at least one assay chamber in fluid connection with the inlet adapted to perform an assay on the blood or other body fluid sample; a known volume of solution or suspension comprising at least one binding agent adapted to elicit a reaction and bind to a target marker having a molecular weight no greater than about 40,000 Daltons (Da) in the blood or other body fluid sample; at least one sensor having a signal and adapted to measure an output from the reaction, and being disposed in or about the at least one assay chamber; an input adapted to allow a user to input data and/or background information related to the subject, the data and/or background information comprising at least the subject's age; a processor comprising an algorithm, the processor adapted to process the signal from the at least one sensor and the processor and algorithm adapted to output a determination based at least in part on the signal from the at least one sensor, and at least in part on an estimated kidney function of the subject, the estimated kidney function being based on the inputted data and background information, the determination being a likelihood that the subject has a neurological condition or an assessment of brain health of the subject; and an output device adapted to display or indicate at least the determination.

Still yet another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one binding agent adapted to elicit a chemical reaction and bind to a target marker in the blood or other body fluid sample; at least one electrode adapted to measure an electrical current output from the chemical reaction, the electrode having a signal related at least in part to the measured electrical current, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination.

Yet even another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one binding agent adapted to elicit a chemical reaction and bind to a target marker in the biological sample; at least one electrode adapted to measure an electrical current output from the chemical reaction, the electrode having a signal related at least in part to the measured electrical current, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination, wherein the output device is a display adapted to display measured values of the at least one target marker corresponding to the sensor signal, calculated indexes based on the measured values of the target marker, the determination of the likelihood that the subject has a neurological condition, and/or a recommended treatment based on the determination.

Even still another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one capture molecule adapted to elicit a chemical reaction and bind to a target marker in the blood or other body fluid sample; at least one electrode adapted to measure an electrical current output from the chemical reaction, the electrode having a signal related at least in part to the measured electrical current, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination, wherein the wherein at least one binding agent capture molecule captures a molecular target selected from the group consisting of the protein listed in Table 1, in all their forms and polymorphic variants and the at least one target marker is an autoreactive antibody directed against one of the selected molecular targets. These are referred to as "preferred protein".

Yet still another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one capture molecule adapted to elicit a chemical reaction and bind to a target marker in the blood or other body fluid sample; at least one electrode adapted to measure an electrical voltage output from the chemical reaction, the electrode having a signal related at least in part to the

TABLE 1

| UniProt | Protein names | Mass (Dalton) | Salivary source |
|---|---|---|---|
| P59665 | Neutrophil defensin 1 | 10,201 | CF |
| P05109 | Protein S100-A8 (Calgranulin-A) | 10,835 | CF |
| P06702 | Protein S100-A9 | 13,242 | CF |
| A4D1T9 | Probable inactive serine protease 37 | 26,445 | CF |
| P07477 | Trypsin-1 | 26,558 | CF |
| P08246 | Neutrophil elastase | 28,518 | CF |
| P02647 | Apolipoprotein A-I | 30,778 | CF |
| Q9H1X3 | DnaJ homolog subfamily C member 25 | 42,404 | CF |
| Q9ULX6 | A-kinase anchor protein 8-like | 71,649 | CF |
| PO1833 | Polymeric immunoglobulin receptor | 83,284 | CF |
| P13639 | Elongation factor 2 | 95,338 | CF |
| P28325 | Cystatin-D | 16,080 | IP |
| P80511 | Protein S100-A12 | 10,575 | IP |
| P78556 | C-C motif chemokine 20 | 10,762 | IP |
| P55773 | C-C motif chemokine 23 | 13,411 | IP |
| Q9NSA1 | Fibroblast growth factor 21 | 22,300 | IP |
| Q8IXJ6 | NAD-dependent protein deacetylase sirtuin-2 | 43,182 | IP |
| Q96NZ9 | Proline-rich acidic protein 1 | 17,208 | IP |
| O14788 | Tumor necrosis factor ligand superfamily member 11 | 35,478 | IP |
| O43557 | Tumor necrosis factor ligand superfamily member 14 | 26,350 | IP |
| P01135 | Protransforming growth factor alpha | 17,006 | IP |
| P01374 | Lymphotoxin-alpha | 22,297 | IP |
| P13725 | Oncostatin-M | 24,484 | IP |
| P21583 | Kit ligand | 30,899 | IP |
| P78423 | Fractalkine | 42,203 | IP |
| O95630 | STAM-binding protein | 48,077 | IP |
| P09238 | Stromelysin-2 | 54,151 | IP |
| P30203 | T-cell differentiation antigen | 71,801 | IP |
| P14210 | Hepatocyte growth factor | 83,134 | IP |
| O15169 | Axin-1 | 95,635 | IP |
| P28325 | Cystatin-D | 16,080 | PP |
| Q9NRJ3 | C-C motif chemokine 28 | 14,280 | PP |
| P11362 | Fibroblast growth factor receptor 1 | 91,868 | PP |
| P03915 | NADH-ubiquinone oxidoreductase chain 5 | 67,027 | PP |
| P48163 | NADP-dependent malic enzyme | 64,150 | PP |
| Q16378 | Proline-rich protein 4 | 15,097 | PP |
| O43508 | Tumor necrosis factor ligand superfamily member 12 | 27,216 | PP |
| O75888 | Tumor necrosis factor ligand superfamily member 13 | 27,433 | PP |
| P06703 | Protein S100-A6 | 10,180 | PP |
| P59665 | Neutrophil defensin 1 | 10,201 | PP |
| Q9H299 | SH3 domain-binding glutamic acid-rich-like protein 3 | 10,438 | PP |
| P05109 | Protein S100-A8 | 10,835 | PP |
| P06702 | Protein S100-A9 | 13,242 | PP |
| A0A075B6K6 | Immunoglobulin lambda variable 4-3 | 13,330 | PP |
| P06312 | Immunoglobulin kappa variable 4-1 | 13,380 | PP |
| P0DJI8 | Serum amyloid A-1 protein | 13,532 | PP |
| P39019 | 40S ribosomal protein S19 | 16,060 | PP |
| P28325 | Cystatin-D | 16,080 | PP |
| P02810 | Salivary acidic proline-rich phosphoprotein 1/2 | 17,016 | PP |
| P15531 | Nucleoside diphosphate kinase A | 17,149 | PP |
| P22392 | Nucleoside diphosphate kinase B | 17,398 | PP |
| Q9H0U4 | Ras-related protein Rab-1B | 22,171 | PP |
| P37802 | Transgelin-2 | 22,391 | PP |
| P61026 | Ras-related protein Rab-10 | 22,541 | PP |
| Q8IWL1 | Pulmonary surfactant-associated protein A2 | 26,182 | PP |
| Q8IWL2 | Pulmonary surfactant-associated protein A1 | 26,242 | PP |
| P07477 | Trypsin-1 | 26,558 | PP |
| P91981 | 14-3-3 protein gamma | 28,303 | PP |
| O75586 | Mediator of RNA polymerase II transcription subunit 6 | 28,425 | PP |
| P21796 | Voltage-dependent anion-selective channel protein 1 | 30,773 | PP |
| P02647 | Apolipoprotein A-1 | 30,778 | PP |
| P60174 | Triosephosphate isomerase | 30,791 | PP |
| Q04118 | Basic salivary proline-rich protein 3 | 30,980 | PP |
| P23280 | Carbonic anhydrase 6 | 35,367 | PP |
| Q8N474 | Secreted frizzled-related protein 1 | 35,386 | PP |
| P40926 | Malate dehydrogenase, mitochondrial | 35,503 | PP |
| P68032 | Actin, alpha cardiac muscle 1 | 42,019 | PP |
| P68133 | Actin, alpha skeletal muscle | 42,051 | PP |
| P36952 | Serpin B5 | 42,100 | PP |
| P01880 | Immunoglobulin heavy constant delta | 42,353 | PP |
| Q9Y2A9 | N-acetyllactosaminide beta-1,3-N-acetylglucosaminyltransferase 3 | 42,534 | PP |

TABLE 1-continued

| UniProt | Protein names | Mass (Dalton) | Salivary source |
|---|---|---|---|
| P12277 | Creatine kinase B-type | 42,644 | PP |
| P30740 | Leukocyte elastase inhibitor | 42,742 | PP |
| O95084 | Serine protease 23 | 43,001 | PP |
| Q06828 | Fibromodulin | 43,179 | PP |
| P05783 | Keratin, type I cytoskeletal 18 | 48,058 | PP |
| Q04695 | Keratin, type I cytoskeletal 17 | 48,106 | PP |
| P04217 | Alpha-1B-glycoprotein | 54,254 | PP |
| P01042 | Kininogen-1 | 71,957 | PP |
| P08238 | Heat shock protein HSP 90-beta | 83,264 | PP |
| P01833 | Polymeric immunoglobulin receptor | 83,284 | PP |
| P13639 | Elongation factor 2 | 95,338 | PP |
| Q8WUM4 | Programmed cell death 6-interacting protein | 96,023 | PP |
| P28325 | Cystatin-D | 16,080 | PS |
| P80511 | Protein S100-A12 | 10,575 | PS |
| Q9NRJ3 | C-C motif chemokine 28 | 14,280 | PS |
| P11362 | Fibroblast growth factor receptor 1 | 91,868 | PS |
| Q16378 | Proline-rich protein 4 | 15,097 | PS |
| Q9NS68 | Tumor necrosis factor receptor superfamily member 19 | 46,015 | PS |
| P06703 | Protein S100-A6 | 10,180 | PS |
| P59665 | Neutrophil defensin 1 | 10,201 | PS |
| P25815 | Protein S100-P | 10,400 | PS |
| Q9H299 | SH3 domain-binding glutamic acid-rich-like protein 3 | 10,438 | PS |
| P80511 | Protein S100-A12 | 10,575 | PS |
| P05109 | Protein S100-A8 | 10,835 | PS |
| P06702 | Protein S100-A9 | 13,242 | PS |
| A0A075B6K6 | Immunoglobulin lambda variable 4-3 | 13,330 | PS |
| P06312 | Immunoglobulin kappa variable 4-1 | 13,380 | PS |
| P0DJI9 | Serum amyloid A-2 protein | 13,527 | PS |
| P0DJI8 | Serum amyloid A-1 protein | 13,532 | PS |
| P28325 | Cystatin-D | 16,080 | PS |
| P32320 | Cytidine deaminase | 16,185 | PS |
| P02810 | Salivary acidic proline-rich phosphoprotein 1/2 | 17,016 | PS |
| P15531 | Nucleoside diphosphate kinase A | 17,149 | PS |
| P02144 | Myoglobin | 17,184 | PS |
| P22392 | Nucleoside diphosphate kinase B | 17,298 | PS |
| P07998 | Ribonuclease pancreatic | 17,644 | PS |
| Q06830 | Peroxiredoxin-1 | 22,110 | PS |
| P62081 | 40S ribosomal protein S7 | 22,127 | PS |
| Q9H0U4 | Ras-related protein Rab-1B | 22,171 | PS |
| P45973 | Chromobox protein homolog 5 | 22,225 | PS |
| P37802 | Transgelin-2 | 22,391 | PS |
| Q92522 | Histone H1x | 22,487 | PS |
| Q8IWL1 | Pulmonary surfactant-associated protein A2 | 26,182 | PS |
| O75015 | Low Affinity immunoglobulin gamma Fc region receptor III-B | 26,216 | PS |
| Q8IWL2 | Pulmonary surfactant-associated protein A-1 | 26,242 | PS |
| P07477 | Trypsin-1 | 26,558 | PS |
| P23396 | 40S ribosomal protein S3 | 26,688 | PS |
| P61981 | 14-3-3 protein gamma | 28,303 | PS |
| P08246 | Neutrophil elastase | 28,518 | PS |
| P20151 | Kallikrein-2 | 28,671 | PS |
| P62753 | 40S ribosomal protein S6 | 28,681 | PS |
| P02647 | Apolipoprotein A-I | 30,778 | PS |
| P60174 | Triosephosphate isomerase | 30,791 | PS |
| Q13151 | Heterogenous nuclear ribonucleoprotein A0 | 30,841 | PS |
| Q04118 | Basic salivary proline-rich protein 3 | 30,980 | PS |
| P23280 | Carbonic anhydrase 6 | 35,367 | PS |
| Q8N474 | Secreted frizzled-related protein 1 | 35,386 | PS |
| P40926 | Malate dehydrogenase, mitochondrial | 35,503 | PS |
| Q9UBQ7 | Glyoxylate reductase/hydroxypyruvate reductase | 35,668 | PS |

measured electrical voltage, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination.

Still even another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one capture molecule adapted to elicit a chemical reaction and bind to a target marker in the biological sample; at least one electrode adapted to measure an electrical voltage output from the chemical reaction, the electrode having a signal related at least in part to the measured electrical voltage, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination, wherein the output device is a display adapted to display measured values of the at least one target marker corresponding to the sensor signal, calculated indexes based on the measured values of the target marker, the determination of the likelihood that the subject has a neurological condition, and/or a recommended treatment based on the determination.

Even yet another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one capture molecule adapted to elicit a chemical reaction and bind to a target marker in the blood or other body fluid sample; at least one electrode adapted to measure an electrical voltage output from the chemical reaction, the electrode having a signal related at least in part to the measured electrical voltage, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination, wherein at least one binding agent capture molecule captures a molecular target selected from the group consisting of the protein listed in Table 1, in all their forms and polymorphic variants and the at least one target marker is an autoreactive antibody directed against one of the selected molecular targets.

Yet even still another embodiment of the present invention includes a portable point-of-care assay device for determining a likelihood that a subject has a neurological condition comprising: an inlet adapted to receive a blood or other body fluid sample taken from a subject; at least one assay chamber in fluid connection with the inlet adapted to perform a chemical assay on the blood or other body fluid sample; a known volume of solution or suspension comprising at least one capture molecule adapted to elicit a chemical reaction and bind to a target marker in the blood or other body fluid sample; at least one electrode adapted to measure an electrical voltage output from the chemical reaction, the electrode having a signal related at least in part to the measured electrical voltage, and being disposed in or about the at least one assay chamber; an input mechanism adapted to allow a user to input data and background information related to the subject; a processor comprising an algorithm adapted to process the sensor signal and output a determination based at least in part on the sensor signal and at least in part on the data and background information related to the subject, the determination being correlated to a likelihood that the subject has a neurological condition; and an output device adapted to display or indicate the determination, wherein at least one binding agent capture molecule captures a molecular target selected from the group consisting of the protein listed in Table 1, in all their forms and polymorphic variants and the at least one target marker is an autoreactive antibody directed against one of the selected molecular targets.

Even still yet another embodiment of the present invention includes a portable point-of-care assay device for determining a likelihood that a subject has a neurological condition comprising: an inlet adapted to receive a biological sample taken from a subject; at least two assay chambers in fluid connection with the inlet adapted to perform a chemical assay on the biological sample; a first known volume of solution or suspension corresponding to one of the at least two assay chambers, the first solution or suspension comprising at least one first capture molecule, and a second known volume of solution or suspension corresponding to another of the at least two assay chambers, the second solution or suspension comprising at least one second capture molecule, each of the capture molecules being adapted to elicit a chemical reaction and bind to at least one first and second target markers in the blood or other body fluid sample, wherein the at least one first and second target markers corresponding wherein at least one binding agent capture molecule captures a molecular target selected from the group consisting of the protein listed in Table 1, in all their forms and polymorphic variants and the other target marker is an autoreactive antibody directed against one of the selected molecular targets; at least two sensors adapted to measure an electrical output from the chemical reactions in each assay chamber, the sensors each having a signal and at least one sensor being disposed in or about each of the at least two assay chambers; an input mechanism adapted to allow a user to input data and background information related to the subject; a processor comprising an algorithm adapted to process the sensor signals and output a determination based at least in part on the sensor signals and at least in part on the data and background information related to the subject, the determination being correlated to a likelihood that the subject has a neurological condition; and an output device adapted to display or indicate the determination.

Still yet even another embodiment of the present invention includes a portable point-of-care assay device for determining a likelihood that a subject has a neurological condition comprising: an inlet adapted to receive a biological sample taken from a subject; at least two assay chambers in fluid connection with the inlet adapted to perform a chemical assay on the biological sample; a first known volume of solution or suspension corresponding to one of the at least two assay chambers, the first solution or suspension comprising at least one first capture molecule, and a second known volume of solution or suspension corresponding to another of the at least two assay chambers, the second solution or suspension comprising at least one second capture molecule, each of the capture molecules being adapted to elicit a chemical reaction and bind to at least one first and second target markers in the blood or other body fluid sample, the at least one first and second target markers corresponding to the at least one first and second target molecules respectively; at least two sensors adapted to measure an electrical output from the chemical reactions in each assay chamber, the sensor each having a signal and at least one sensor being disposed in or about each of the at least two assay chambers; an input mechanism adapted to allow a user to input data and background information related to the subject; a processor comprising an algorithm adapted to process the sensor signals and output a determination based at least in part on the sensor signals and at least in part on the data and background information related to the subject, the determination being correlated to a likelihood that the subject has a neurological condition; and an output device adapted to display or indicate the determination, wherein the output device is a display adapted to display measured values of the at least one target marker corresponding to the sensor signal, calculated indexes based on the measured values of the target marker, the determination of the likelihood that the subject has a neurological condition, and/or a recommended treatment based on the determination.

Even yet still another embodiment of the present invention includes a portable point-of-care assay device for determining a likelihood that a subject has a neurological condition comprising: an inlet adapted to receive a biological sample taken from a subject; at least two assay chambers in fluid connection with the inlet adapted to perform a chemical assay on the biological sample; a first known volume of solution or suspension corresponding to one of the at least two assay chambers, the first solution or suspension comprising at least one first capture molecule, and a second known volume of solution or suspension corresponding to another of the at least two assay chambers, the second solution or suspension comprising at least one second capture molecule, each of the capture molecules being adapted to elicit a chemical reaction and bind to at least one first and second target markers in the blood or other body fluid sample, the at least one first and second target markers corresponding to the at least one first and second molecules respectively; at least two sensors adapted to measure an electrical output from the chemical reaction, the sensors each having a signal and at least one sensor being disposed in or about each of the at least two assay chambers; an input mechanism adapted to allow a user to input data and background information related to the subject; a processor comprising an algorithm adapted to process the sensor signals and output a determination based at least in part on the sensor signals and at least in part on the data and background information related to the subject, the determination being correlated to a likelihood that the subject has a neurological condition; and an output device adapted to display or indicate the determination, wherein the at least one first and at least one second capture molecules are different capture molecules, and where the at least one first capture molecule is selected from the group consisting of the protein listed in Table 1, and the corresponding target marker is an antibody directed against the selected capture molecule, and the at least one second capture molecule is the same as the at least one first target marker and the at least one second target marker is the same as the at least one first capture molecule.

Even yet another embodiment of the present invention includes an assay system or device for determining a likelihood that a subject has a neurological condition or to assess brain health comprising a test sheet adapted to receive a saliva fluid sample given by a subject; the test sheet comprising a base layer and at least one binding agent coated onto the base layer, and adapted to elicit a chemical reaction and bind to a target marker in the saliva; and the binding agent adapted to bind with target markers with lower molecular weights no greater than about 60,000 Daltons (Da) and to provide a color change, a fluorescent signal, or chemical luminescence upon binding with a certain quantity of the target marker with the lower molecular weights in the saliva.

Still yet another embodiment of the present invention includes an assay system or device for determining a likelihood that a subject has a neurological condition or to assess brain health comprising a test sheet adapted to receive a saliva fluid sample given by a subject; the test sheet comprising a base layer and at least one binding agent coated onto the base layer, and adapted to elicit a chemical reaction and bind to a target marker in the saliva; and the binding agent adapted to bind with target markers with lower molecular weights no greater than about 60,000 Daltons (Da) and to provide a color change fluorescence or chemical luminescence upon binding with a certain quantity of the target marker in the saliva with the lower molecular weights wherein the wherein at least one binding agent is a capture molecule which captures a molecular target selected from the group consisting of whole protein or fragments thereof the protein listed in Table 1, in all their forms and polymorphic variants and the at least one target marker is an autoreactive antibody directed against one of the selected molecular targets of diagnostic significance.

Even yet still another embodiment of the present invention includes An assay system for determining a likelihood that a subject has a neurological condition or to assess brain health comprising a test sheet adapted to receive a saliva fluid sample given by a subject; the test sheet comprising a base layer and at least one binding agent coated onto the base layer, and adapted to elicit a chemical reaction and bind to a target marker in the saliva; the binding agent adapted to bind with target markers with lower molecular weights no greater than about 60,000 Daltons (Da) and to provide a color change or chemical luminescence upon binding with a certain quantity of the target marker in the saliva with the lower molecular weights; at least one detector having a signal and adapted to measure the color change or chemical luminescence from the chemical reaction, and being disposed or used in close proximity to the test sheet; a processor comprising an algorithm, the processor adapted to process the signal from the at least one detector and the processor and algorithm adapted to output a determination based at least in part on the signal from the at least one detector, the determination being a likelihood that the subject has a neurological condition or an assessment of brain health of the subject; and an output device adapted to display or indicate at least the determination.

The embodiments of the present invention also provide screening methods for diagnosis, prognosis, susceptibility, or degree of permeability of penetration of the blood-brain barrier by detecting the presence of markers of blood-brain barrier disruption such as S100B, tau protein, amyloid beta, GFAP and UCHL-1 and by evaluating their true peripheral levels by a mathematical algorithm. The present invention further provides for kits including detection apparatus and appropriate software for carrying out the above described methods.

It is to be understood that both the foregoing general description and the following detailed description are merely exemplary of the invention with various steps or components being optional in certain circumstances, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

BRIEF DESCRIPTION OF THE DRAWINGS

FIGS. 22A-D. Diagrams depicting various considerations of a pharmacokinetic model for peripheral blood biomarkers and region-specific groupings of initial assignments including A) parameters incorporated into the central nervous system portion of the model, B) initial assignments for various biomarker levels, C) extracranial contribution to concentrations of S100B, and D) representation of passage of biomarkers into and through the kidneys.

DESCRIPTION OF THE PREFERRED EMBODIMENTS

Figure 1A:
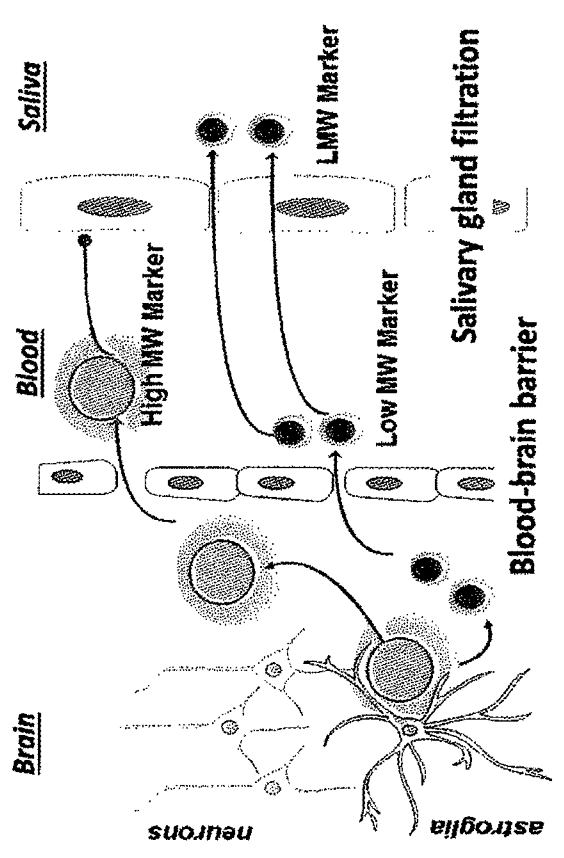
FIG. 1A. Schematic representation of passage of markers from brain to saliva.
Figure 1B:
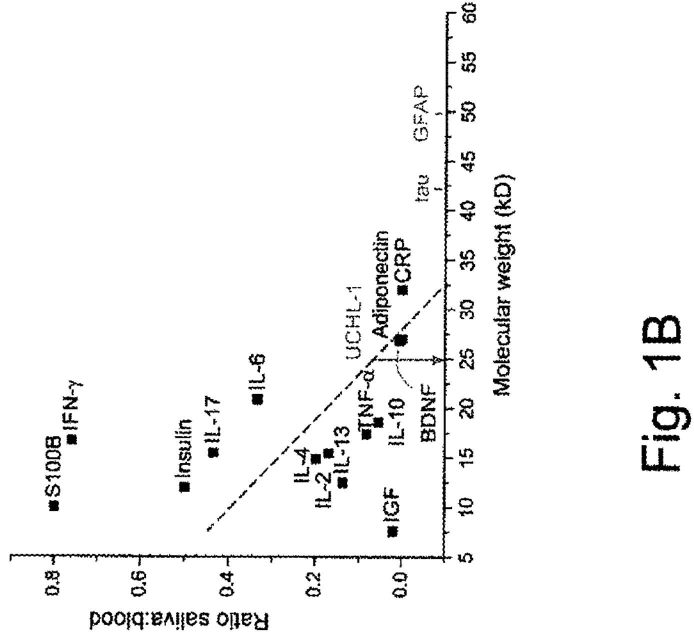
FIG. 1B: Cutoff of salivary protein
Figure 2:
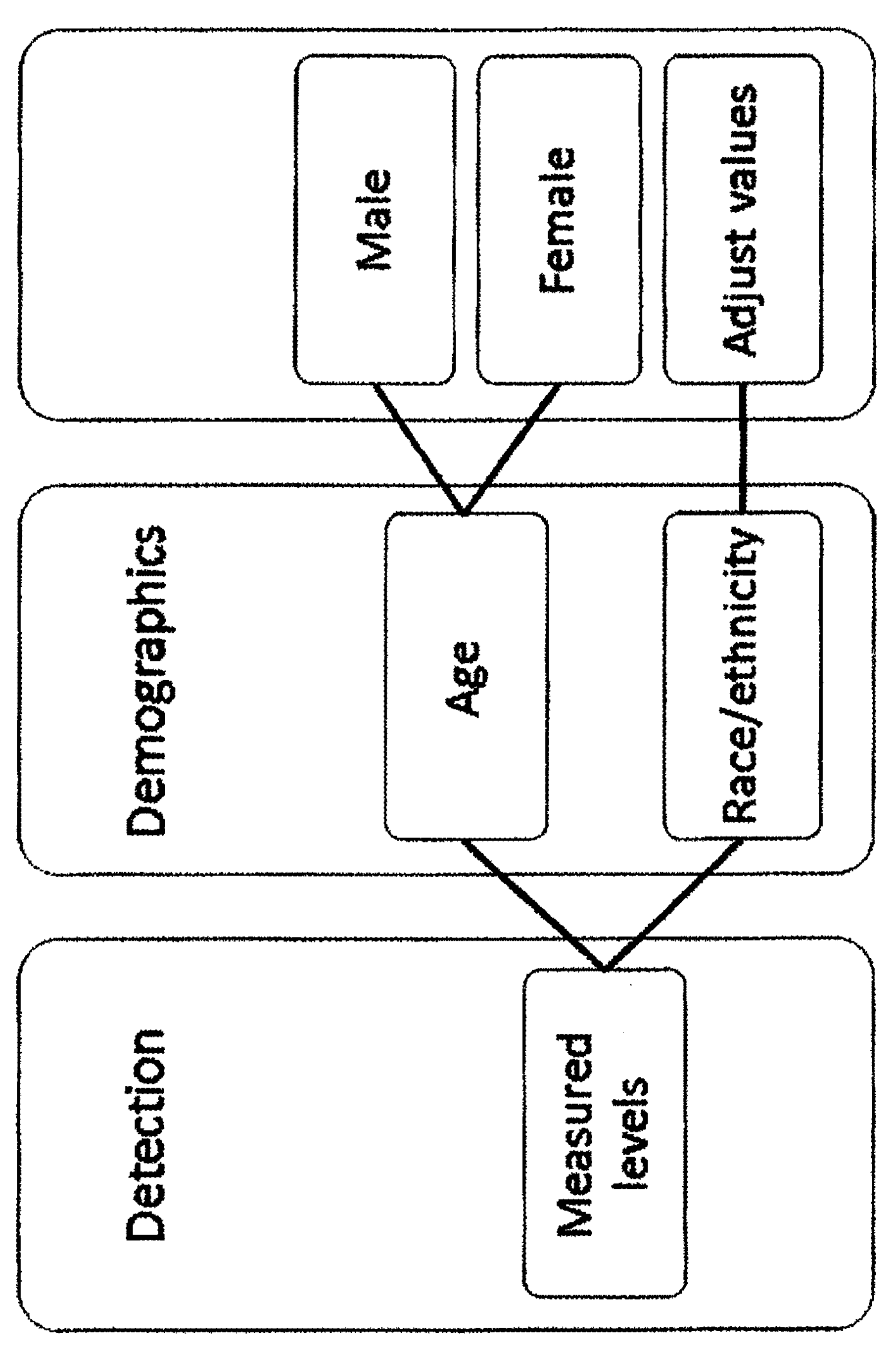
FIG. 2. Algorithm and model assumptions.
Figure 3:
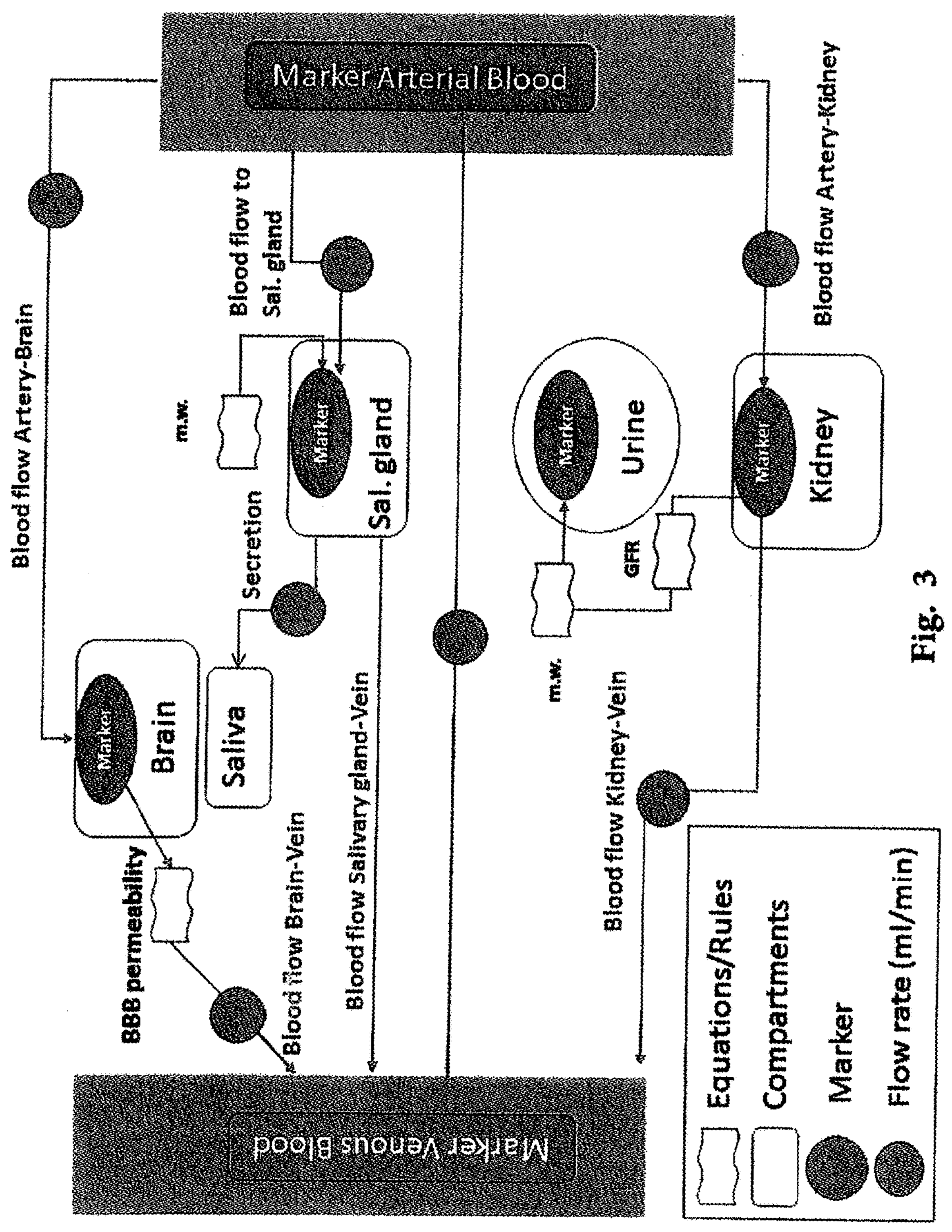
FIG. 3. Schematic depicting passage of markers from blood to saliva.
Figure 4:
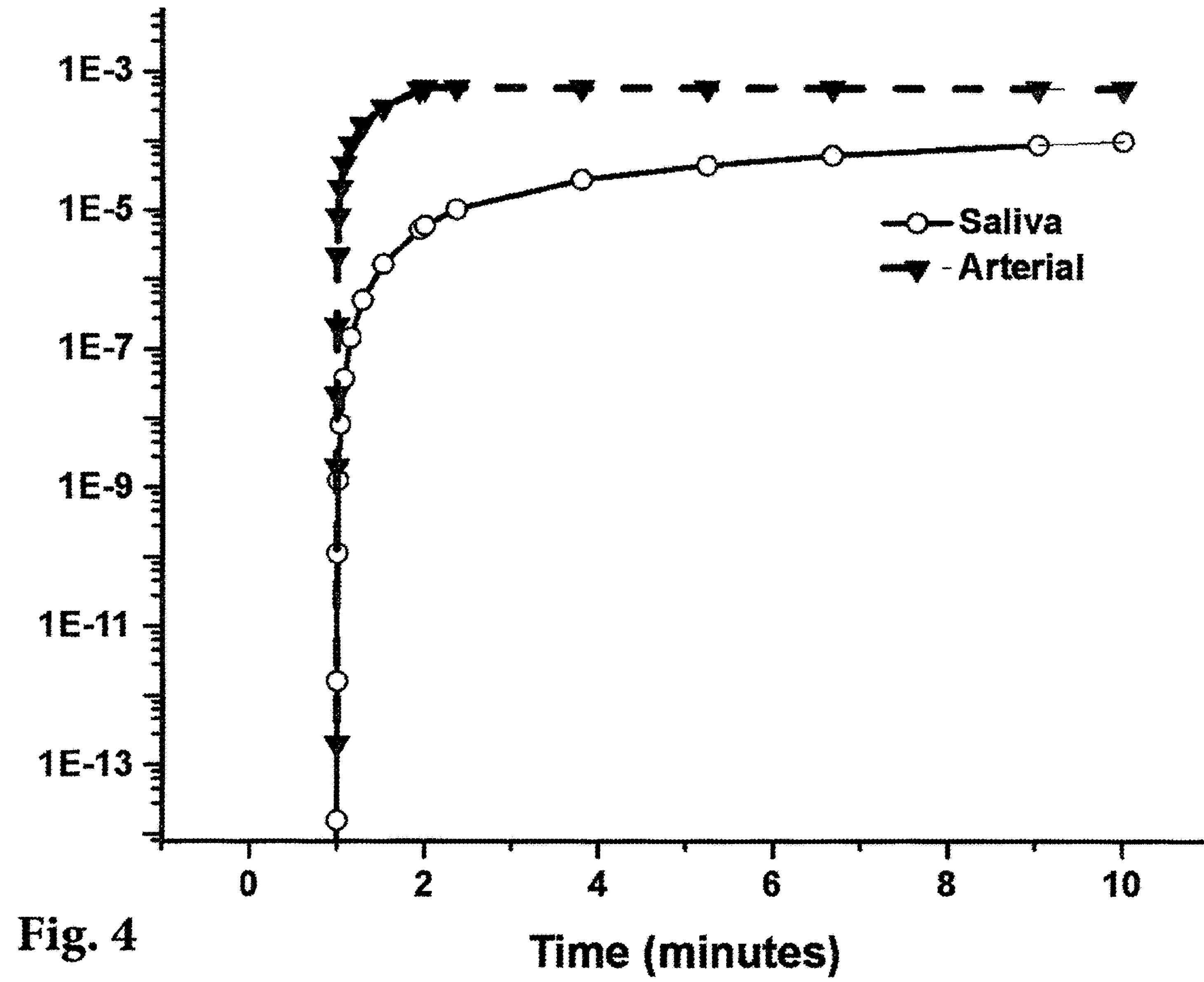
FIG. 4. Graph of results of model demonstrated that for a low molecular weight protein (less than 40 kD) leaked in the circulation from a diseased BBBH the appearance in saliva vs. arterial blood is slightly delayed.
Figure 5:
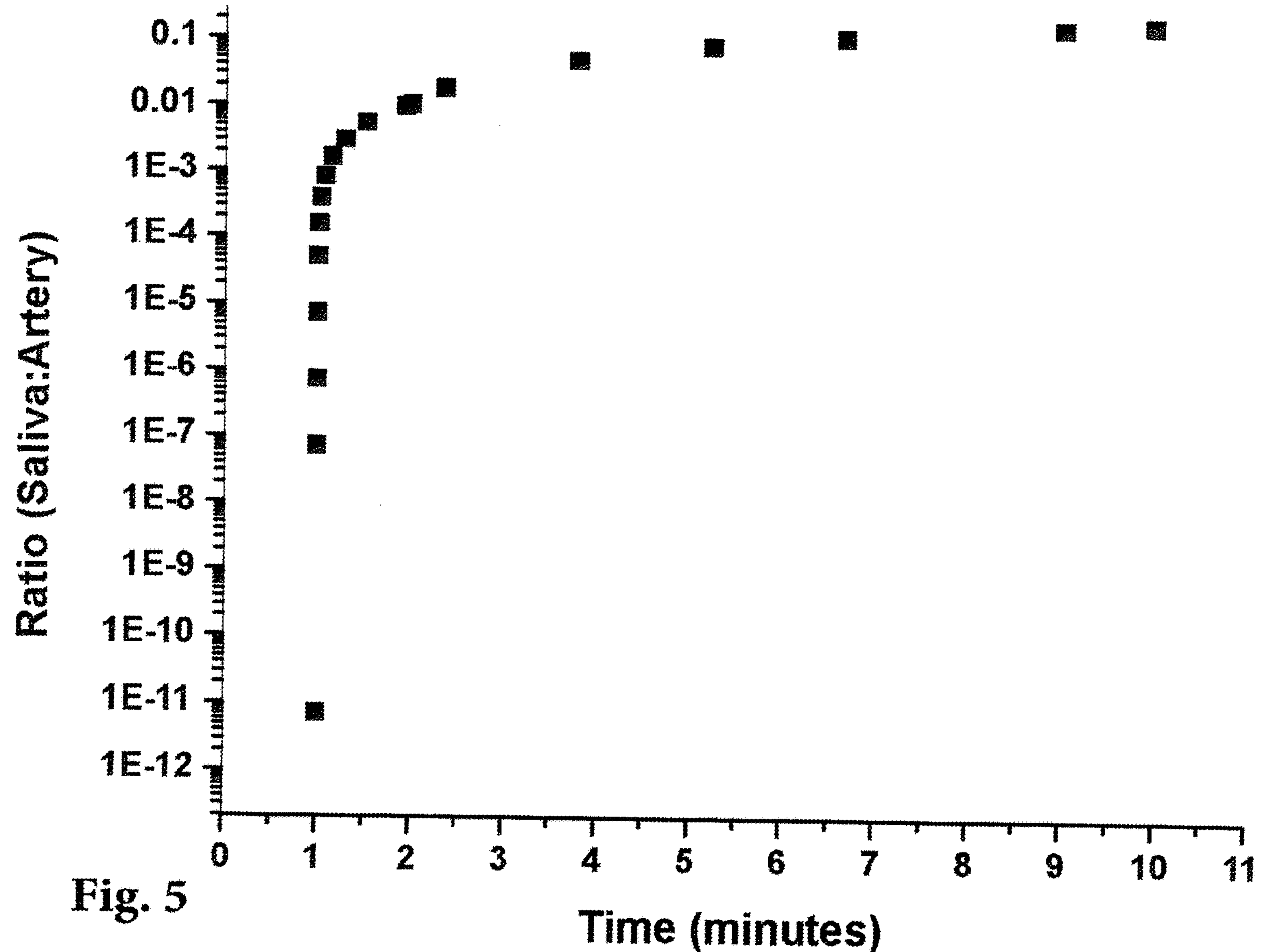
FIG. 5. Graph showing delay is negligible and the steady state values for saliva:artery ratios are rapidly achieved.

The present invention relates to devices and methods for point of care to rule out acute and long term consequences of mild traumatic brain injury (mTBI), to quantify traumatic brain injury (TBI), and to screen or diagnose other neurological disorders such as stroke, epileptic seizures, and psychosis. Various embodiments of the present invention include a device or apparatus in or on which immobilized capture (organic or inorganic) molecules or atoms can be used directly or in conjunction with secondary detection molecules to elicit an electrical signal that is used to quantify a target analyte. Other embodiments of the present invention include a device, system, method or apparatus in or on which immobilized capture (organic or inorganic) molecules or atoms can be used directly or in conjunction with secondary detection molecules to elicit a color change or chemical luminescence reaction to determine the extent of a target marker or protein in the subject's saliva, blood or other bodily fluids. Several analytes may be measured, including, but not limited to, proteic, brain-derived blood markers used to assess acute post-traumatic sequelae, autoreactive immunoglobulins against the same brain-derived protein biomarkers, or other analytes that may be known in the art or become known. The present invention can be use at home, in the field, at sporting events, and just about anywhere there is a need for providing a screening or diagnostic test detecting a neurological condition such as mTBI, TBI, stroke, psychosis or the like particularly where a neurological injury occurs and a decision needs to be made as to whether further diagnosis or treatment is or may be necessary. The present invention further can be used in any emergency setting such as an emergency room, nursing home, military theatre, medical transport, or in any setting, social or private, where a concussive injury occurs and a quick decision regarding the triage status of a post-traumatic victim needs to be made. The acute test for concussion or mTBI is particularly useful as a triage panel for CT or MRI scans in a population of TBI victims with a favorable Glasgow Coma Score, a minority of whom is nevertheless at risk for intracranial sequelae. In addition, the present invention can be used as a screening test for neuroimaging studies to assess long-term sequelae of previous concussion(s), TBI or mTBI. In general, the present invention is directed to systems, devices and methods for determining a likelihood that a subject has a neurological condition or for providing a general or directed assessment of brain health.

With regards to the assays performed within the POC device, some embodiments may include a reactive paper or polymer that can be placed in contact with a biological fluid or other biological sample from the patient, and whereby an enzyme, chemical, binding agent, antibody or other reactive compound on the strip reacts with the biological sample to alter the appearance of at least a portion of the strip such as to change the color, shading or chemical luminescence of an area of the strip to provide an indication of the concentration of the target marker in the biological sample. Such indication on the strip would then be analyzed by a user or clinician in order to determine the patient's disease state or injury status in order to determine a recommended treatment or course of action. In addition various patterns may be used on the test strip to indicate what level of target marker is in the sample of bodily fluid being tested. For example various lines could be used each being indicative of a different threshold of target marker. In this case level of the target marker could be measured based on how many lines (or thresholds) changed color or provided chemical luminescence. In other embodiments the level of color change, shading or chemical luminescence could be measure with a photo detection sensor (detector) such as provided on a smart phone along with an app that would allow the detector to very accurately measure the amount of target maker in the body fluid based on chemical reactions described below providing for this color change/shading or chemical luminescence.

Various membranes or substrates can be used for eliciting a chemical reaction between a binding agent and target marker. Nitrocellulose and polyvinylidene difluoride (PVDF) are the preferred substrates, however, depending on the application, various other binding agents and target markers may also be used.

Preferably, the assays described herein are performed by eliciting a chemical reaction between a binding agent and a target marker. Preferably, the binding agent is a capture molecule which captures a molecular target. Examples of target markers that may be used, depending on the assay include, but are not limited to, the protein listed in Table 1. Alternatively, one of these or similar agents may be the binding agent, and the binding agent may be an autoreactive antibody directed against the selected binding agent.

More preferably, the system and device or apparatus is automated or semi-automated adapted to accept a biological sample and process the results of an assay that takes place on or within the system or device. The system preferably comprises a housing or substrate that provides a base and structure for the system. The housing or substrate can be made of any biocompatible or functionally sufficient material known in the art, such that the material can come into contact with biological samples and not react with such samples or cause any change to the structure, makeup or integrity of the sample. Preferably the housing is manufactured from a polymer material and further from a material that is biodegradable. Further, the housing can be either reusable or disposable, and if reusable may comprise replaceable parts. Preferably, for embodiments where the system or device is more robust with electronic components for performing analysis and providing complex or detailed outputs, the system is reusable and is thus preferably easy to open or disassemble for easy cleaning and sanitization after use. The housing or substrate preferably comprises an inlet port or entry adapted to allow the biological fluid or other biological sample to be input into the system. The system also preferably includes a sample chamber or an area where the sample is either placed, comes into contact with or comes to rest after being introduced through the inlet port or entry. Some embodiments may include a conduit connecting the inlet port or entry to the sample chamber which allows the biological fluid or other biological sample to traverse any distance between the inlet port or entry and enter the sample chamber. Other embodiments may provide for a saliva collection pad, an inlet for collecting saliva, and other devices and methods for placing the saliva in contact with a test strip. The sample chamber or a test strip allows the biological sample, preferably saliva, to be put in contact with a reagent, chemical, binding agent, antibody, enzyme or other reactive compound thus allowing the sample and compound to interact and react.

Using a sensor or detector is optional for a color change or chemical luminescence reaction. When a sensor is used, the system also preferably includes a sensing chamber comprising at least one sensor adapted to detect an output or product of the reaction between the sample and the reactive compound. With an electrochemical reaction a sensing chamber may be the same or distinct and separate from the sample chamber depending on the embodiment. The sensing chamber preferably comprises a well (or substrate in the case of a color change or chemical luminescence) in which the sample may rest (or be carried respectively), and depending on the type of sample utilized may further comprise a substrate such as a solid phase support or carrier which is adapted to hold the sample (typically when the sample is a fluid) and potentially immobilize any analytes, markers and/or proteins in the sample. The at least one sensor is disposed within the sensing chamber such that the sensor can detect the output or product of the reaction including when looking at color change or chemical luminescence. The reaction and sensing steps, described in greater detail below, which in the case of an electrochemical reaction are carried out in the respective chambers such that the sample and compound react with each other and a chemical reaction occurs which produces an output or product that is detected by the sensor, which sends a signal that is based on the reaction detected. This sensor signal is then sent to a transducer which processes and converts the sensor signal into an electrical signal that is based at least in part on the sensor signal and which is indicative of the level of the reaction between the sample and the reactive compound. The system preferably further includes a processor which is adapted to analyze the electrical signal produced by the transducer, in some embodiments utilizing an algorithm designed to take into account the signal as well as various patient-specific properties, and to provide an output signal. The output signal preferably is directly correlated with the concentration of the target analyte or marker in the biological sample. Preferably, the processor and/or algorithm are adapted to provide an output signal, based at least in part on the signal(s) from the sensor(s), that is a determination that the subject has some neurological condition, a likelihood that the subject has some neurological condition, and/or an assessment of the subject's brain health. The output signal may comprise multiple forms of information including simple indicators as to the patient's status or likelihood of the presence of TBI and/or BBB disruption, or detailed information such as indexes calculated from the signals of the system related to the concentration of the target analyte or marker, descriptions of the patient's status, diagnosis determinations, recommended treatments or courses of action, or the like. The system may preferably include an output device to communicate such output information, such as a display screen or monitor, a light device, an audio output device or the like. Such information can be as simple as providing a "yes", "+", "−", "seek attention" or the line across the substrate, monitor or screen output. Some embodiments may comprise a screen or monitor adapted to display the detailed information described above. Other embodiments may comprise a simple light, preferably an LED light, adapted to emit a certain light based on the results of the assay and indicating whether the patient is in good condition (no or only minor TBI and/or BBB disruption requiring no further testing) or bad or uncertain condition (thus indicating further testing is required for a proper diagnosis). The system may also comprise audio output devices adapted to output a message, alarm or other indicator as to the patient's status or instructions. Various embodiments of the present invention may include any one or more of the above elements, including one or more of the output devices.

The assay device may be a portable device, and more preferably may be a portable point-of-care (POC) device capable of being deployed at the scene of a potential injury. The portable or POC device may be a standalone assay unit that is capable of performing the assay and providing feedback by itself. Alternatively, the portable or POC device particularly in the case of an electrochemical reaction may be designed such that it is a modular unit that interfaces with a stationary assay system, such as those located in hospital or laboratory settings. Interface assay devices may be adapted to house all the necessary components for performing the assay and then be interfaced with the stationary assay system to perform further analysis and our output of results, or may be adapted to house a biological sample and/or assay solutions and compounds until the portable or POC assay device is interfaced with the stationary system which performs the assay and output. Most preferably, the portable or POC device is capable of performing either/both functions depending on the particular circumstances and environment.

The various system embodiments of the present invention may include at least one or more elements including an inlet port or opening adapted to receive a biological fluid or other biological sample taken from a patient, a conduit or test strip connecting the inlet port or opening to a reaction chamber or window opening in the case of a test strip housing. With an electrochemical reaction preferably there is a preparation chamber, a sensing compartment comprising at least one sensor having a signal, the sensor being adapted to sense an electrochemical reaction between the sample and a binding agent, a transducer adapted to process the signal from the sensor and produce an electrical signal based at least in part on the sensor signal, a processor adapted to analyze and/or process the electrical signal, an output device adapted to display or otherwise communicate an output signal based at least in part on the processed and/or analyzed electrical signal, and the like. Many embodiments may include other elements as well. The assay device of various embodiments of the present invention preferably includes an inlet port. The inlet port provides an entry point for the biological sample to be entered or otherwise placed into the assay device. Once the biological sample has entered the inlet port, it preferably traverses through a conduit or pathway or along a test strip that connects the inlet port to a sample chamber or the reactive portion of the test strip where the sample collects and rests in order to be tested or in the case of a test strip reacts with the binding agent. In embodiments where the assay device is designed to open, such as with a hinged or removable lid or cap, the sample may be placed directly into the sample chamber or on a portion of the test strip or on a collection pad connected to the test strip, and thus no inlet port and/or conduit or pathway would be required. However, many preferred embodiments utilize the inlet port and sample chamber design in order to maintain sterility of the system and to prevent any contaminants from entering the sample chamber.

Many assay device embodiments of the present invention also preferably include a sensing compartment comprising at least one sensor having a signal where the sensor is adapted to sense an electrochemical reaction or a photo chemical reaction between the sample and a chemical. The chemical is preferably a binding agent of a type that binds to a target analyte or marker in the sample. In some embodiments, the sample chamber and sensing chamber may be one in the same, or two separate chambers may be used. Single or separate chamber systems may be preferable depending on the particular assay being performed. For example, if the assay is one where the reaction between the sample and the binding agent must be measured substantially immediately upon the sample and binding agent coming into contact with each other, it may be preferable to utilize a separate chamber system such that the sample can be placed into the device and rest in the sample chamber until the time when the reaction is ready to be measured, and then can be moved, or caused to move, into the sensing chamber to come into contact with the binding agent, thus causing the necessary reaction and allowing the reaction to be measured. Other assays may not require substantially immediate measurement, and the sample and binding agent can be allowed to come into contact immediately, in a single sample/sensing chamber, and the reaction measured when appropriate.

The sensor having a signal can be any type of sensor capable of measuring the output of the particular assay. Many embodiments utilize assays designed to output an electrical signal, in the form of electrons release during the chemical reaction. Thus, many preferred embodiments may utilize an electrode capable of detecting the electrical signal. Such sensors may measure an electrical current, electrical voltage, or impedance. The sensor, upon detecting electrochemical reaction between the sample and the binding agent, outputs a signal based on the detected electrochemical reaction. The assay device further comprises a transducer which is adapted to receive the signal output from the sensor and processes the sensor signal, converting it into a different electrical signal based on the sensor signal and correlating to a measurement of the electrochemical reaction. For example, if the electrode senses a strong electrochemical reaction between the sample and the binding agent, the sensor signal would correspond or correlate to a large electrical charge output from the reaction. The resultant sensor signal would then be transmitted to the transducer which would convert the strong electrical sensor signal into a separate electrical signal correlating, in some embodiments, to a measured quantification of the electrical signal from the sensors—thus providing a measurement of the electrochemical reaction. Other assay types, such as chemiluminescent, utilize sensors that are capable of detecting light output, typically in the form of photons, such as a photodiode sensor with a light source disposed on the opposite side of the sample such that the photodiode detects changes in light output from the light source as affected by the chemical reaction in the assay chamber. Another optional sensor type is a radioactive sensor to measure output of radioactive reactions, photochromatic sensors to measure changes in light or color, and the like. In some embodiments, multiple types of assays might be performed on an individual sample or a partitioned sample. Multiple types of assays performed have been found in clinical studies to significantly enhance the accuracy, sensitivity and specificity, of assay determinations.

The transducer signal may then be transmitted to processor, which is adapted to receive and process the transducer's electrical signal. Depending on the embodiment, the processor may be a part of the assay device attached to, embedded into, or otherwise integrated into the device. However, other embodiments may utilize a separate processor remote from the POC assay device. Utilizing a separate processor may be preferable for assay device embodiments that are designed to be disposable in order to minimize cost and electrical components that are discarded, for example. In embodiments where a separate, remote processor is utilized, the processor may be part of a computer, tablet, cell or smart phone or the like. The POC assay device would then require a communications component, such as a radio antenna, to transmit the transducer signal to the processor. Such communication could be performed via any communication platform known or later-developed, including, but not limited to, radio frequency (RF), Wi-Fi, Bluetooth, cellular phone, or the like. In any embodiment, the transducer signal is communicated to the processor which processes the signal in order to output a signal to an output device. The output device is preferably adapted to display or otherwise communicate an output signal based at least in part on the processed and/or analyzed signal from the processor. The output device, similar to the processor, may be a part of the assay device attached to, embedded into, or otherwise integrated into the device, or may be separate and remote from the POC assay device. The output device may be a visual output device such as a display, such as a monitor, screen, LED screen, one or more lights or LEDs, or any other such system for communicating a test result and/or indication as to whether further testing is required to a user. Alternatively, the system may utilize audio or tactile outputs. Audio outputs may include audio messages such as a readout of the measured concentration of the marker measured or an indication that the marker's concentration is high or low or that the subject is injured and needs further testing or no further testing is required, or may be a simple sound or series of sounds that convey the patient's condition and/or need for further testing. Tactile outputs may include vibration, for example if the patient requires further testing the output device could vibrate. The output of the system, communicated via the output device, can be quantitative or semi-quantitative. Quantitative output preferably includes a direct concentration measurement of the target marker, though may be a measure of any of the electrical signals within the system that may be used to determine the concentration of the marker. Semi-quantitative output may include an indication of whether the patient requires further testing, has suffered a TBI and/or BBB disruption, is exhibiting marker concentrations above normal or above threshold, or the like.

The various method embodiments of the present invention may include one or more of the steps of determining patient-specific demographic information, acquiring a biological fluid or other biological sample from a patient, placing the biological fluid or other biological sample in or in contact with a device, the device adapted to receive a biological fluid or other biological sample, analyzing the sample by performing an assay on the sample using the device, the assay adapted to determine the concentration of at least one biological marker, determining the concentration of at least one given biological marker comprised in the sample, processing the concentration of the at least one marker comprised in the sample, determining a disease state of the patient, determining a probability or likelihood that the patient is suffering from a degree of TBI and/or a disruption of the BBB, outputting a determination, determining a recommended treatment or course of action, providing a signal, warning or message indicating the determination and/or the recommended treatment or course of action, or the like. Many embodiments may include other steps as well.

One step of various method embodiments of the present invention is determining patient-specific demographic information. Baseline S100B, or other biological markers used in conjunction with the present invention, are often affected by demographic information such as age and race or ethnicity. In order to properly assess the patient's condition and to get an accurate analysis of the outputs of the system, it may be important to ascertain specific information about a given subject or patient. This demographic information may be used as input to the system, particularly for automated or semi-automated systems utilizing electronic components and algorithm(s) to process the sample and provide analysis, or for analog systems, such as where the test is performed using a reactive test component such as a strip of paper or polymer, the demographic information may be noted or recorded and considered by a user when analyzing the analog results. The patient-specific demographic information may be obtained by any method available at the time the present invention is employed, including questionnaire, verbal questioning of the patient, inquiring with bystanders or witnesses to the injury, checking known sources of information such as medical records or identification cards, or the like. The method by which the patient-specific information is acquired may be variable and is dependent upon the status of the patient. Preferably, the patient-specific properties include the disease condition of the patient at time of blood or fluid draw. Given that the present invention is particularly useful for injuries that cause mTBI, the patients are likely to be conscious or semi-conscious and coherent or semi-coherent, and thus able to respond to questions regarding their demographic status. However, this is not always the case, and other methods may need to be employed, or they can be used to verify the patient's responses.

For some embodiments, basic demographic information may not be sufficient, and more in-depth patient-specific properties at time of testing or prior to risk factors may be required in order to provide a proper and accurate analysis. This is due to the fact that, as noted, S100B levels for a particular patient are affected by many factors, including, but not limited to, demographic information (e.g., age, race, gender, height, weight), the patient's particular medical history, family history and risk factors, intake to the subject's system such as pharmaceuticals or medications the patient might be taking, and the like. Preferably, the patient-specific properties include genetic, ethnic, physiologic, therapeutic and pathologic properties. Preferably, the patient-specific properties include one or more of age, gender, transgender status, ethnicity, and pregnancy state. Preferably, the age property of the patient is one of four classifications corresponding to a patient of less than ten years of age (pediatric), a patient between the ages of 10 and 30 (young adult), a patient greater than 30 years old but less than 65 years old (adult), and a patient greater than 65 years of age (aged). Preferably, the ethnicity property of the patient is classed as one of (a) Caucasian; (b) African-American or Central African; (c) North African or Arab; (d) Indian; (e) Chinese or Korean; (f) Japanese; or (g) Australasian.

Preferably, the patient-specific properties and/or sample-specific properties include hemodilution of the patient's blood at time of draw and, if applicable, at a presumed time of blood-brain barrier disruption. Preferably, the sample-specific properties include the presence and levels of autoreactive or autoimmune, self-directed immunoglobulins in the sample at time of analysis. Preferably, the patient-specific properties and/or sample-specific properties include therapy received by the patient at time of blood or fluid draw. More preferably, the sample-specific properties include the levels or concentrations of one or more therapeutics in the sample. Preferably, such therapeutics are those that have known effects of glomerular filtration, blood-brain barrier repair, protein binding, or kidney filtration pressure.

Another step of various method embodiments of the present invention includes acquiring a biological fluid or other biological sample from the subject or patient. Depending on the embodiment, and more particularly on the specific target marker(s), the sample may be any body fluid or tissue that is readily obtainable from the injured patient, including, but not limited to, blood, cerebrospinal fluid, saliva, sweat, tears, urine, skin cells, epithelial cells, hair, and the like. Preferably, the sample is easily obtainable in a manner that will not cause further harm or trauma to the patient. The sample may be drawn from the subject by any method known in the art. Samples can be as little as 2.5 ml or less taken from the subject. Further, all markers can preferably be measured with as little as one assay device or by using a separate assay device for each marker, in which case aliquots of the same fluid or tissue sample can be used or different samples can be used.

Another step of various method embodiments of the present invention includes placing the biological fluid or other biological sample into or in contact with a device or apparatus that is adapted to receive a sample for testing. The device or apparatus, described above, is preferably designed to accept (such as via an inlet port or an opening) and house (such as in a sample chamber) a biological sample such that the sample can come in contact with a binding agent that reacts with the sample to detect the target marker. Various embodiments of the system may be adapted differently to accept the sample. In many preferred embodiments where the preferred sample is a saliva sample, the POC assay device may be adapted such that the inlet port can be placed against a source (e.g., in the oral cavity) and act as a capillary tube such that the saliva would be drawn into the inlet port, through a conduit or pathway and into the sample chamber. For embodiments that open, a user may open or remove a lid or covering from the PC assay device, directly place the sample into the sample chamber, and then replace the lid or cover on the device. Given the acute-care environment in which the present invention may often be employed, it is conceived that many methods for collecting samples and placing them into or in contact with the device may be utilized or improvised.

Yet another step of various method embodiments of the present invention includes analyzing the sample by performing an assay on the sample using the device, the assay being adapted to determine the concentration of a target analyte or marker in the biological sample. Many different assays and assay techniques may be used to analyze the sample, including, but not limited to, ELISA, immunodetection assay, detection assays based on mass spectroscopy, "sandwich" immunoassays, immunoprecipitation assays, precipitation reactions, gel diffusion precipitation reactions, immunodiffusion assays, agglutination assays, complement fixation assays, immunoradiometric assays, fluorescent immunoassays, protein A immunoassays, radioimmunoassays, Western blots, and the like. One preferable method is to use an immunoassay whereby a solution comprising antibodies that bind, preferably specifically, to the target analyte or marker are applied to the sample. The antibodies then bind with the target analyte or marker (e.g., S100B). The sample is preferably washed with suitable buffers at least once, though possibly more times, before the binding agent, reagent and/or antibody is added. A second or subsequent buffer wash may be performed after the binding agent, reagent and/or antibody is added in order to remove any unbound antibodies such that only antibodies bound to the analyte or marker are measured. When the target analyte or marker binds with the antibody, in preferred analysis assays, an electrical charge is released. Greater concentrations of the target analyte or marker in the sample lead to more binding reactions, and thus more electrical charge is released. A sensor in the chamber where the sample and solution comprising the binding agent interact is adapted to detect the released electrical charges. Some embodiments may utilize reagents or binding agents other than antibodies, such as polypeptides may be used. Another alternative is to use an enzyme assay whereby the antibodies are linked to an enzyme which, when the antibody binds to the target marker or analyte, the enzyme reacts with a substrate in the reagent or binding agent mixture to produce a chemical output that can be detected by the sensor or perhaps visually, such as with a chromogenic enzyme that changes color upon reaction. Still another alternative is to radioactively label the antibodies and detect a radioactive isotope that is released upon binding of the antibody to the target analyte or marker. Yet another alternative is to label the antibody with a fluorescent compound or a bioluminescent compound and detect the output of fluorescence or luminescence upon binding. In all embodiments, the reagent or binding agent used preferably is chosen based on the analyte or marker that is to be measured, and is selected based on its specificity and sensitivity to that analyte or marker. Analyte- or marker-specific reagents are desired in order to minimize the risk and amount of false positive detections that occur where the reagent or binding agent binds with a macromolecule, compound, element or other analyte that is not the target analyte or marker. The goal is to introduce a binding agent or reagent comprising antibodies that bind as specifically and sensitively as possible to the target analyte or marker, thus allowing the antibodies to bind with any analyte or marker in the sample to produce the attendant reaction and detect, with a sensor, the output of those reactions. The number of individual binding reactions that are detected can be directly correlated to the volume of the target analyte or marker in the sample and used to quantify the concentration of the analyte or marker in the sample.

Still another step of various embodiments of the present invention includes determining the concentration of a target analyte or marker in the biological sample. As just noted, the antibodies are allowed to bind with the analyte or marker in the sample in order to generate an output from the binding reaction and to measure the output of each binding reaction that occurs with a sensor. For assays where the output is an electrical charge (e.g., a single electron released), each electrical charge that is detected can be correlated to an instance of a binding reaction between the antibody (or polypeptide, or other reagent), and can be used to quantify the number of binding reactions that occur. This can then be translated with that transducer and/or processor into a measure of the concentration of the target analyte or marker contained in the sample. The correlation is based in part on the knowledge of the binding reaction and the output of each instance of binding between the antibody or reagent and the target analyte or marker. As long as the preferred binding reaction is known and understood, and the antibody or reagent is chosen to be reasonably sensitive and specific to binding with the target analyte or marker, the output can be measured and quantified to determine the concentration of the target analyte or marker in the sample.

Yet still another step of various embodiments of the present invention includes determining a disease state of the subject and/or a probability or likelihood that the subject is suffering from a degree of TBI and/or a disruption of the BBB. Once the concentration of the target analyte or marker in the sample is known, this concentration can be used to determine that patient's state in regards to a disease state, injury severity or likelihood that some pathologic condition exists. The determination may require more information that just a measured concentration of analyte or marker, however. Given the variation between patients with respect to a "normal" level of many analytes or markers, the raw concentration measurement of a given analyte or marker might not be enough to determine if the particular patient has elevated levels of that analyte or marker. As discussed throughout, patient-specific information may also be required as input into the system to make the determination of whether the patient's measured concentrations are normal or either below or above normal and thus indicative of a pathologic condition, or high likelihood of a pathologic condition. Demographic and other patient-specific information, as described herein, is preferably able to be input into the system in order to tailor the results to the specific patient and his or her normal levels of the analyte or marker. In accordance with this, some embodiments of the POC assay device will have an input component such as a keyboard or touch screen, or will be able to receive such information from another device such as a computer, tablet, cell or smart phone, or the like. Alternatively, the patient specific information may be entered into the separate device comprising a processor, and the results of the assay from the POC assay device can be transmitted to the separate device, again being a computer, tablet, cell or smart phone or the like, and the analysis be performed on the separate device in light of the patient-specific information. Alternatively, or in addition, the patient's assay results may be compared against a normal population of patients, preferably comprising information from a plurality of patients contained in a database on the assay device, a separate device, or a remote database in communication with either the assay device or the separate device, in order to determine whether the patient's concentration of the analyte or marker in the sample could be considered normal, or above or below. The database preferably comprises data, both demographic and diagnostic, from a plurality of other subjects. Such other subjects may include those indicated as "normal", that is without a neurological condition or in good or normal brain health, and/or subjects who have exhibited a disease state in that they had some neurological condition or bad or abnormal brain health. Further preferably, the data in the database corresponds to the chemical assays that were performed in making the clinical determination as to any neurological condition or the subject's brain health assessment, and further corresponding to the target markers that were assayed in order to make the determination. Preferably, demographic information in the database includes at least age, gender, race, height and weight. By cross-referencing the database, the processor and/or algorithm are able to compare the instant subject's measured assay results with those of other subjects previously tested in order to determine how the instant patient, particularly based on similar demographics, compares to other subjects from the past. This comparison allows the processor and/or algorithm to make the determination of presence or absence of a neurological condition or provide an assessment of brain health, based at least in part on what expected values would be for the instant subject based on the demographic information, which greatly influences the expected levels of many target markers. In any embodiment, the measured concentration of the target analyte or marker is compared against expected levels from one or more other sources to determine if the patient is experiencing, or has a certain likelihood of experiencing, a pathologic condition such as a disease state or injury such as TBI and/or BBB disruption. Thresholds for the determination may be preset based on normal populations or may be dynamically set in light of the inputted patient-specific information, or may be based on a combination of sources.

Preferably, the determination of a level of diseased state of the patient is further based one or more previous adjusted levels of blood-brain barrier disruption such that the level of diseased state is noted as a different level of diseased state than a previously determined level of diseased state.

As such, the values of the measured marker may be adjusted by (1) age (infant <1 years old; pediatric <10 years old.; young adult <30 years old.; adult <65; aged >65;) of the patient at time of sampling of peripheral blood or other body fluids; (2) gender of the patient and transgender status; (3) ethnicity (Caucasian; African-American or Central African; North African or Arab; Indian; Chinese or Korean; Japanese; Australasian); and (4) pregnancy-related factors whereby the dual (maternal and fetal) contribution to maternal blood levels of biomarker in the mother needs to be recognized. Clinical guidelines recommend laboratory monitoring of transgender persons on cross-sex hormone therapy, but gender-specific reference intervals leave clinicians with the dilemma of deciding what is "normal" for each patient. Use of correct reference intervals in interpreting laboratory results reduces the risk of testing-related diagnostic error. Preliminary data suggest that new reference intervals need to be established for transgender patients.

The values of the measured marker may also be adjusted based upon hemodilution of the patient's blood at time of draw and if applicable at presumed time of blood-brain barrier disruption. When the marker's molecular weight is less than 40 kD, the marker's value in the sample is also adjusted by glomerular filtration values in the patient at time of draw and if applicable at presumed time of blood-brain barrier disruption. Table 2 presents data relating to the marker's molecular weight and the effect thereof on the time course of serum S100B levels.

TABLE 2

| Effect of Marker's Molecular Weight (N = 83) | |
|---|---|
| Bivariate Fit of High Molecular Weight IgG ng/mL by $cr_{clearance}$ | Bivariate Fit of Low Molecular Weight S100B (ng/mL) By $cr_{clearance}$ |

TABLE 2-continued

| Effect of Marker's Molecular Weight (N = 83) | |
|---|---|
| IgG ng/mL = 2.8770677 − 0.0061373*$cr_{clearance}$ | S100B (ng/mL) = 0.0954183 − 0.0003415*$cr_{clearance}$ |
| Summary of Fit | Summary of Fit |
| RSquare 0.015698<br>RSquare Adj 0.003394 | RSquare 0.106731<br>RSquare Adj 0.095703 |
| Analysis of Variance | Analysis of Variance |
| Prob > F = 0.2621 | Prob > F = 0.0026* |

The marker's value may also be adjusted based upon total plasma or serum protein content in the sample from which the marker of blood-brain barrier disruption is present at time of analysis. The marker's value may also be adjusted based upon the presence and levels of autoreactive or autoimmune, self-directed immunoglobulins in the sample at time of analysis. The marker's values may be evaluated in the context of therapy received by the patient at time of blood or fluid draw. Therapeutics which have known effects of glomerular filtration, blood-brain barrier repair, protein binding, kidney filtration pressure, are computed to determine the clinically relevant values of the marker in blood or fluids. The marker's values may be evaluated in the context of the sampling location used to retrieve peripheral blood (venipuncture, port, arterial blood). The marker's values may be evaluated in the context of the sampling methods used to retrieve peripheral blood (syringe, intravenous or intra-arterial catheter; one- or two-way port). The marker's values may be evaluated in the context of disease condition in the patient at time of blood or fluid draw. Diseases with known direct or indirect effects on blood-brain barrier function or dysfunction or repair are computed to determine the clinically relevant values of the marker in blood or fluids. It is noted that the level of blood-brain barrier disruption may progress or relent over time and therefore indicate different stages of diseased states.

Even still yet another step of various embodiments of the present invention includes outputting a determination as to the subject's disease state and/or probability that the subject is suffering from a degree of TBI and/or BBB disruption. Once the system has made the appropriate determination regarding the patient's condition, the determination is preferably output to a user via an output device or system as described above. The determination may be output as a binary determination of some variety, effectively a go/no go determination which indicates whether the patient is experiencing a pathologic condition and possibly whether the patient should undergo further testing or analysis, such as by imaging (e.g., CT, MRI, etc.). More preferably, the system output may include the binary go/no go determination as well as some more detailed information, including, but not limited to warnings or notifications (audio, visual or a combination) as to the patient's status, quantitative information such as the measured concentration of the target analyte or marker, and/or semi-quantitative information such as the actual determination and/or likelihood that the patient is in a disease state and/or has suffered an injury such as TBI and/or BBB disruption. The output is preferably displayed on and/or emitted from the POC assay device, but may also be transmitted to a separate device such as a computer, tablet, cell or smart phone, or the like. In some embodiments, the output may be one or more light indicators that can change color to indicate patient status (e.g., red to indicate further testing required or green to indicate patient is at low risk or low likelihood of having a pathologic condition), or may light up in a pattern to indicate status. More preferably, the output at least in part comprises a determination of the presence or absence of a neurological condition and/or an assessment of the subject's brain health. Still more preferably, the output comprises a determination or assessment and measured values of the target marker. In any embodiment, the user preferably is readily able to discern and understand the patient's condition upon receiving the output and be able to take immediate action based thereupon.

Even yet still another step of various embodiments of the present invention includes determining a recommended treatment or course of action based on the determination of the subject's disease state and/or probability of suffering a degree of TBI and/or BBB disruption. Based on the outputted determination, either the system or a user preferably determines a recommended treatment or course of action to further address the patient's needs. If the determination indicates that the subject is not experiencing a pathologic condition or has a low likelihood of such, then the system or user may determine that the patient may resume normal activities and/or may need further observation for a period of time to assure that the patient's condition does not change. If the determination indicates that the subject is in a disease state and/or has suffered an injury such as TBI and/or BBB disruption, then the system or user may determine that further testing is required. Further testing may include actions such as more invasive marker measuring methods (e.g., lumbar puncture, etc.), or imaging (e.g., CT, MRI or the like) in order to assess the nature and extent of the patient's condition/injury. Preferably, if the system automatically determines the recommended treatment or course of action, the processor makes the determination using an algorithm related to the algorithm that determines the subject status. If the determined status indicates a disease or injury state, then a recommended protocol may be output in the same fashion as the status determination in order to instruct the user or other medical personnel.

Still even yet another step of various embodiments of the present invention includes providing a signal, warning or message indicating the determination and/or the recommended treatment or course of action. The signal, warning or message is output as described above with respect to the output of the determination and can be of any form described herein including quantitative, semi-quantitative or qualitative.

Figure 6:
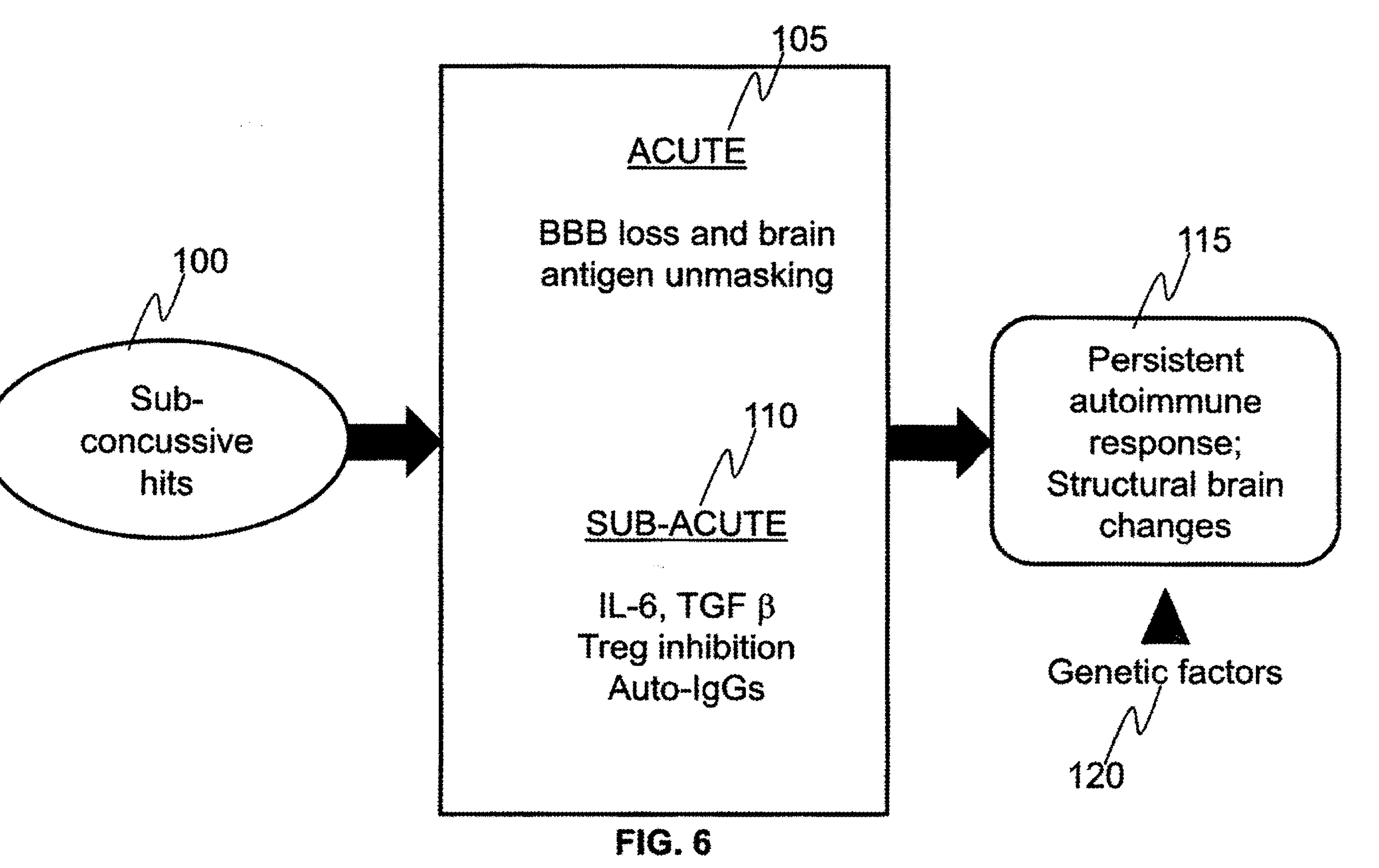
FIG. 6. Diagram depicting the mechanisms linking repeated head injuries to an autoimmune cascade.

Now referring to the Figures, FIG. 6 is a diagram depicting the mechanisms linking repeated head injuries (RHIs) or sub-concussive head hits to an autoimmune cascade. Sub-concussive, repeated head hits 100 are accompanied by surges in S100B in the patient's blood as a result of the disruption of the BBB 105 which is the acute effect 105 of RHIs. Subacute immune response 110 to RHIs includes release of at least Interleukin-6 (IL-6), and transforming growth factor beta (TGF β), as well as inhibition of regulator T cells. A further part of these responses to RHIs is that surges in serum S100B lead to the production of autoantibodies against S100B as part of the patient's autoimmune response and structural changes of the brain 115. Other glio-neuronal proteins, such as synapsin, various isoforms of microtubule-associated protein (MAP) associated with tau protein, neuromodulin, and the like, are also released in serum after RHIs which may also lead to an immune response. The patient's autoimmune response and structural brain changed 115 are further affected by the patients' genetic factors 120.

Figures 7A, 7B:
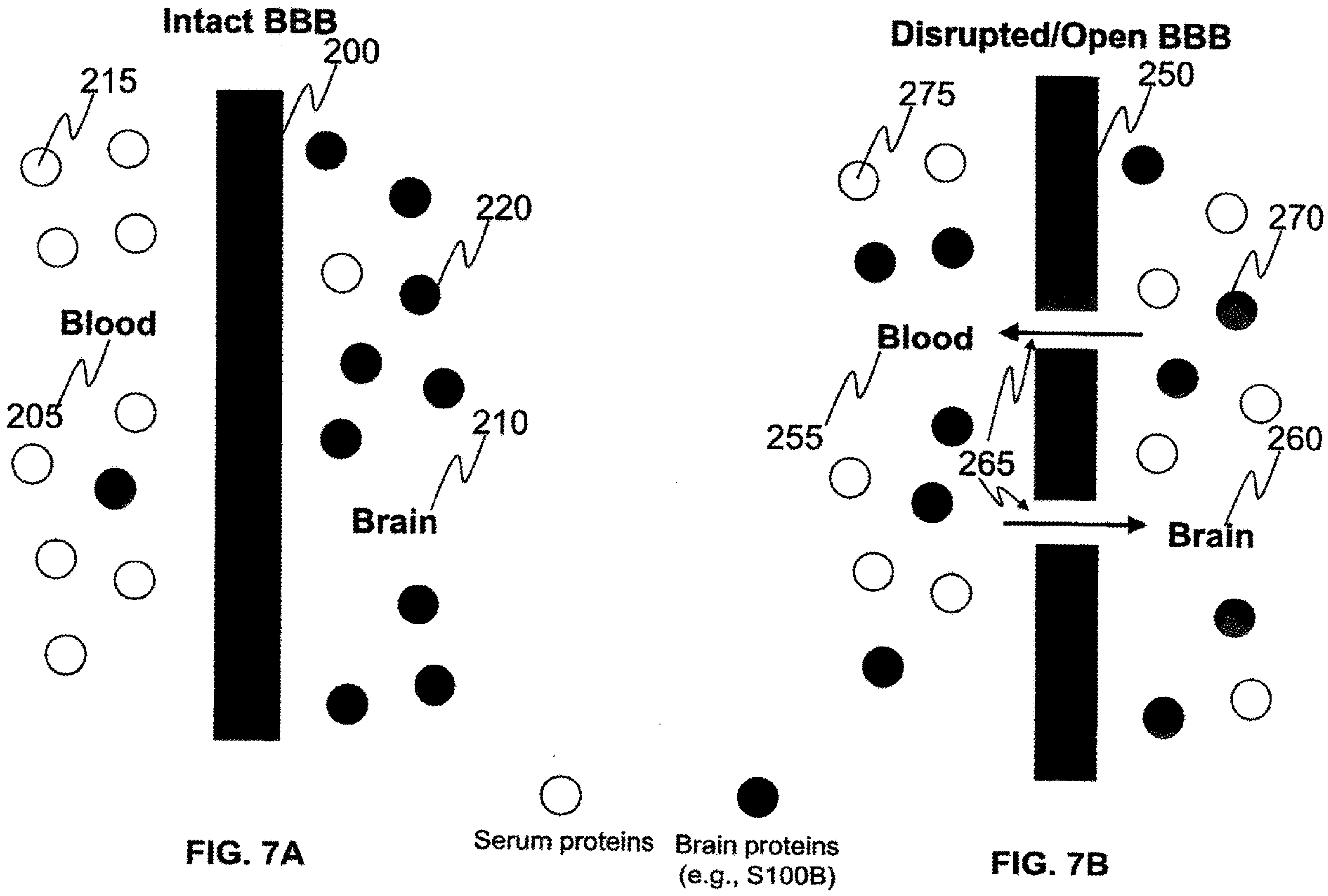
FIGS. 7A-B. Diagrams depicting A) uninjured or undisrupted BBB and B) injured or disrupted BBB and the effect on transfer of proteins.

FIGS. 7A and 7B are pictures depicting a patient's BBB before and after an injury such as TBI. FIG. 7A depicts a normal, undisrupted BBB 200 representative of a person who has not suffered an injury. The undisrupted BBB 200 separates the blood 205 and brain 210 maintaining separation between the two systems and substantially isolates the proteins from each system on either side of the BBB. Thus, blood proteins 215, such as albumin, fibrinogen, and the like remain in the serum or blood 205, and brain proteins 220, such as S100B, glial fibrillary acidic protein (GFAP), and the like remain in the brain with little or no passage of either across the BBB. However, when the patient suffers an injury and the BBB is disrupted, this homeostasis is similarly disrupted. The disrupted BBB 250 opens up providing gaps 265 between the endothelial cells (not shown) that make up the BBB, and no longer maintains separation between the blood 255 and brain 260. These gaps 265 allow the various proteins to cross the disrupted BBB 250 such that brain proteins 270 can enter the patient's serum or blood 255 and blood proteins 275 can enter the patient's brain 260. In other words, when the BBB is disrupted, specific brain proteins can extravasate into the blood according to their concentration gradient, and blood-specific proteins can likewise extravasate into the brain according to their concentration gradient. Thus, measuring the concentration of brain proteins 270 in the patient's blood 255 can provide an indication as to whether the patient has a disrupted BBB 250 as a result of a potential injury.

Figures 8A, 8B:
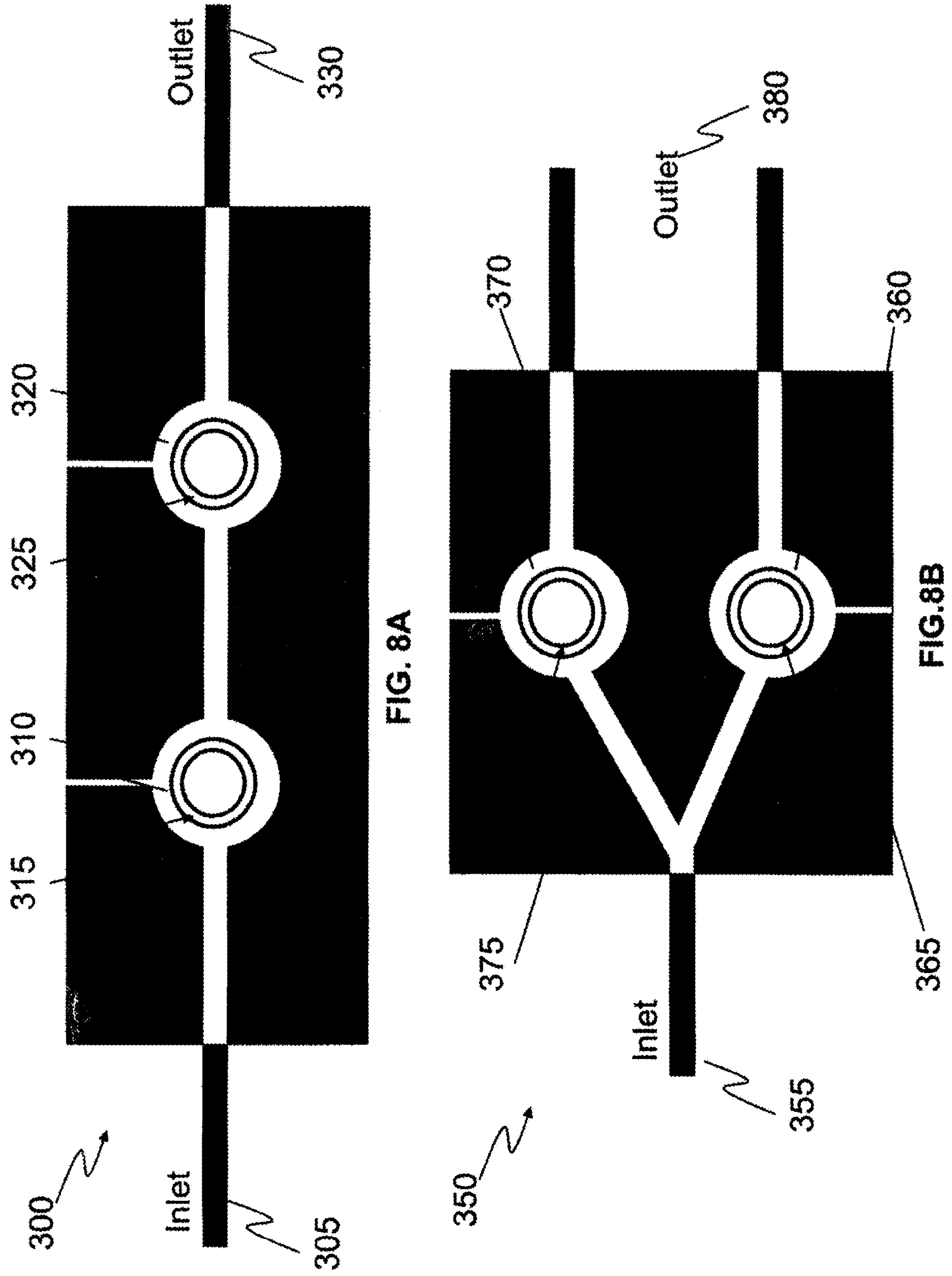
FIGS. 8A-B. Diagrams depicting various embodiments of a POC assay device including A) a serial assay device, and B) a parallel assay device.

FIGS. 8A and 8B are pictures depicting various embodiments of a point of care (POC) or point-of-injury (POI) device for testing a biological sample from a subject to determine the concentration of a target analyte or marker in the sample. FIG. 8A depicts a serial POC assay device 300 designed to measure concentrations of both proteins and antibodies serially. A biological sample, such as fluid or tissue, is entered into the serial POC assay device 300 via the inlet port 305. The sample is allowed and encouraged to travel into the serial POC assay device and to enter a series of sample chambers 310 and 320. In the depicted embodiment, the sample chambers 310 and 320 are actually a combination sample and sensing chamber as each chamber 310 and 320 includes a sensor 315 and 325. The assay is performed according to the techniques described herein, wherein a binding agent or reagent is applied to the sample and preferably the binding agent or reagent reacts with the sample, in each chamber 315 and 320 in order to create a reaction, such as an electrochemical reaction, that provides an output. The reaction is preferably one where the binding agent or reagent binds with the target analyte or marker in the sample. In the depicted embodiment, the first chamber 310 may be used to elicit a reaction whereby the binding agent or reagent binds with a target protein in the sample, and the second chamber 320 may be used to elicit a reaction between the binding agent or reagent and a target antibody in the sample. Each chamber may alternatively be used to assay the sample to determine the concentration of the same analyte or marker in order to provide a redundant test to ensure accuracy. Each reaction preferably is designed to provide a known response, such as an electrochemical output of an electrical charge, or any other output described herein, known in the art, or later developed, whereby the output of the reaction can be detected and measured by the sensor 315 and 325 in each chamber 310 and 320. The reactions in the depicted embodiment are preferably performed serially such that the sample first is assayed in the first chamber 310 to measure the concentration of, for example, a protein in the sample, and then the sample is moved to the second chamber 320 to be assayed to measure the concentration of, for example, an antibody present in the sample. The POC/POI assay device further comprises an outlet port 330 by which the sample may be removed from or allowed to exit the POC/POI assay device. FIG. 8B, depicts a parallel POC assay device 350. The parallel POC assay device 350 is designed to test two subsamples of the same entered sample separately. Again, the sample is introduced into the parallel POC/POI assay device 350 via the inlet port 355, but in the depicted embodiment the sample is separated into two separate subsamples, one of which enters a first chamber 370 and the other of which enters a second chamber 360. Much like the embodiment depicted in FIG. 8A, each chamber 370 and 360 is preferably used to assay the sample contained therein for a different target analyte or marker, though they may be used to test for the same target analyte or marker to provide a redundant test to ensure accuracy. The assays are performed in the same manner as described with respect to FIG. 8A, where, for example, the sample in the first chamber 360 is assayed to determine the concentration of a target protein in the sample, and the sample in the second chamber 370 is assayed to determine the concentration of an antibody in the sample. In either chamber a sensor 365 and 375 is used to measure the output from the assay reaction, and the sensor outputs a signal that correlates to the concentration of the target analyte or marker in each sample. After the assay is complete, each sample may be removed from or allowed to exit the system via an outlet port 380 for each assay channel.

Figure 9:
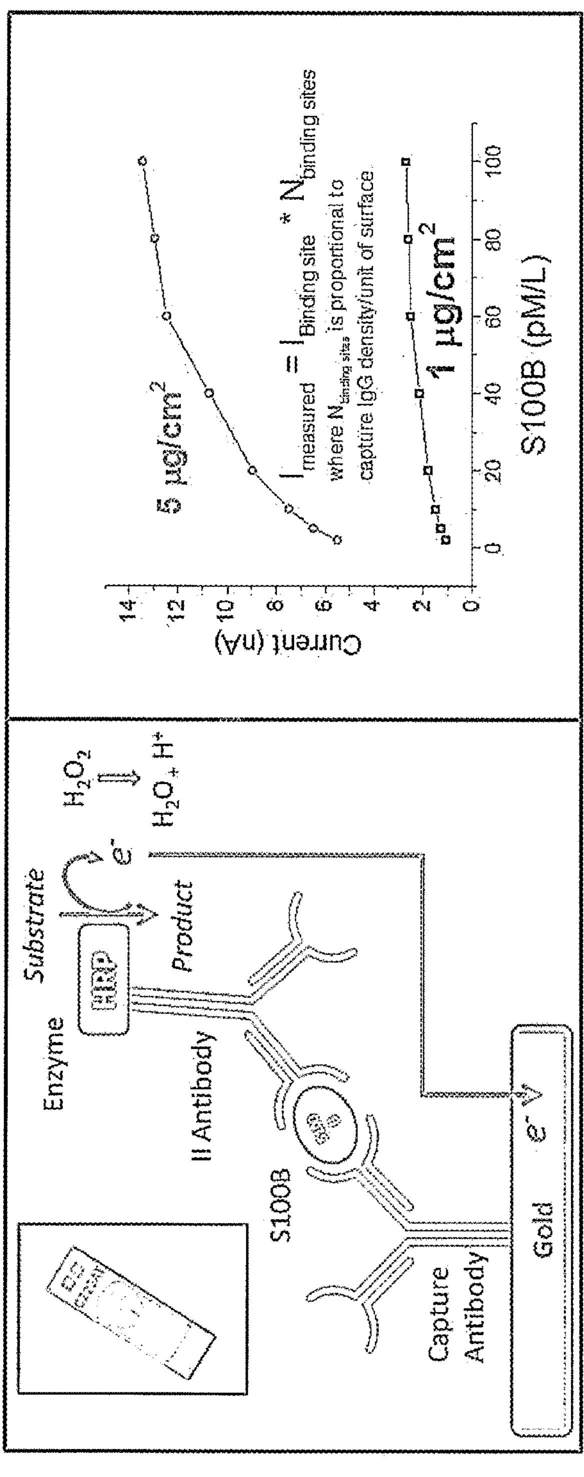
FIG. 9. Diagram of an example assay technique utilized in various embodiments of the present invention.

FIG. 9 depicts an example of an assay technique which may be used in accordance with the present invention. The depicted assay is a sandwich ELISA immunoassay configuration whereby a primary capture antibody 400 captures the target analyte (S100B) 405 and binds to it. The target analyte 405 is labeled using a secondary antibody-enzyme conjugate (II Antibody) 410. Finally, an added enzyme (HRP) 415 becomes converted 420 to an active product, where this conversion releases an electrical charge 425 which is the output of the overall chemical reaction. The figure further depicts an example of an electrode 430 that may be used as the sensor used to measure the output electrical charge 425 of the reaction. Still further, the figure depicts a graph 435 of the relationship between expected current signal and concentration of the immunoglobulin used to coat the working electrode.

In the depicted assay, two approaches can be used to measure the output electrical signal 425 of the reaction: a voltammetric method and an amperometric method. The voltammetric method measures the voltage difference between a gold working electrode 440 and a gold counter electrode. The working electrode is coated with the capture antibody 400, where the coating allows the working electrode 440 to function as an electrode of the second kind, i.e., the coating determines the voltage of the working electrode 440 relative to a reference electrode (not shown) and also to the counting electrode (not shown). The reference electrode (not shown) anchors the system voltage and is used by electronic feedback circuitry in a potentiometer. When the target analyte or marker 405 (GFAP in figure is one example) binds to the capture antibody 400 a change in the voltage of the working electrode 440 ensues. The Goldman equation (Equation 4) predicts that:

$$\frac{V_A}{V_B} = \frac{0.05916}{n} \times \log_{10}\frac{[GFAP]_A}{[GFAP]_B} \qquad \text{Equation 4}$$

That is, an analyte concentration change of a factor of 10, if the analyte/capture antibody involves a single electron discharge, a 59 mV voltage change will be observed. This expression is used to develop a calibration curve my measuring voltage over a range of marker's concentrations. The measurement is a simple measurement of the change in voltage between the working electrode 440 and the counter electrode (not shown), with no current flowing. $V_o$ is the intercept of the calibration curve at zero marker concentration. An amperometric method detects the analyte by measuring current between the working electrode 440 and the counter electrode (not shown). After the marker is added, a "substrate" is formed by a secondary antibody bonded to HRP 415. HRP 415 catalyzes oxidation of $H_2O_2$ in the supporting electrolyte, with an electrical charge 425 being released to the working electrode 440 and protons liberated into the solution. Protons are compensated in the electrolyte by anions released by the counter electrode (not shown). Current from the working electrode (440) to the counter electrode (not shown) is measured by the potentiometer using feedback circuitry. The current magnitude is proportional to the concentration of the analyte, since only those capture antibody sites occupied by analyte bind to secondary antibody/RP to form the electrochemical "substrate" to support the oxidative half reaction. The detector is calibrated by measuring this current at different known analyte concentrations. This calibration can be used to subsequently determine the unknown analyte concentration.

Figures 10A, 10B:
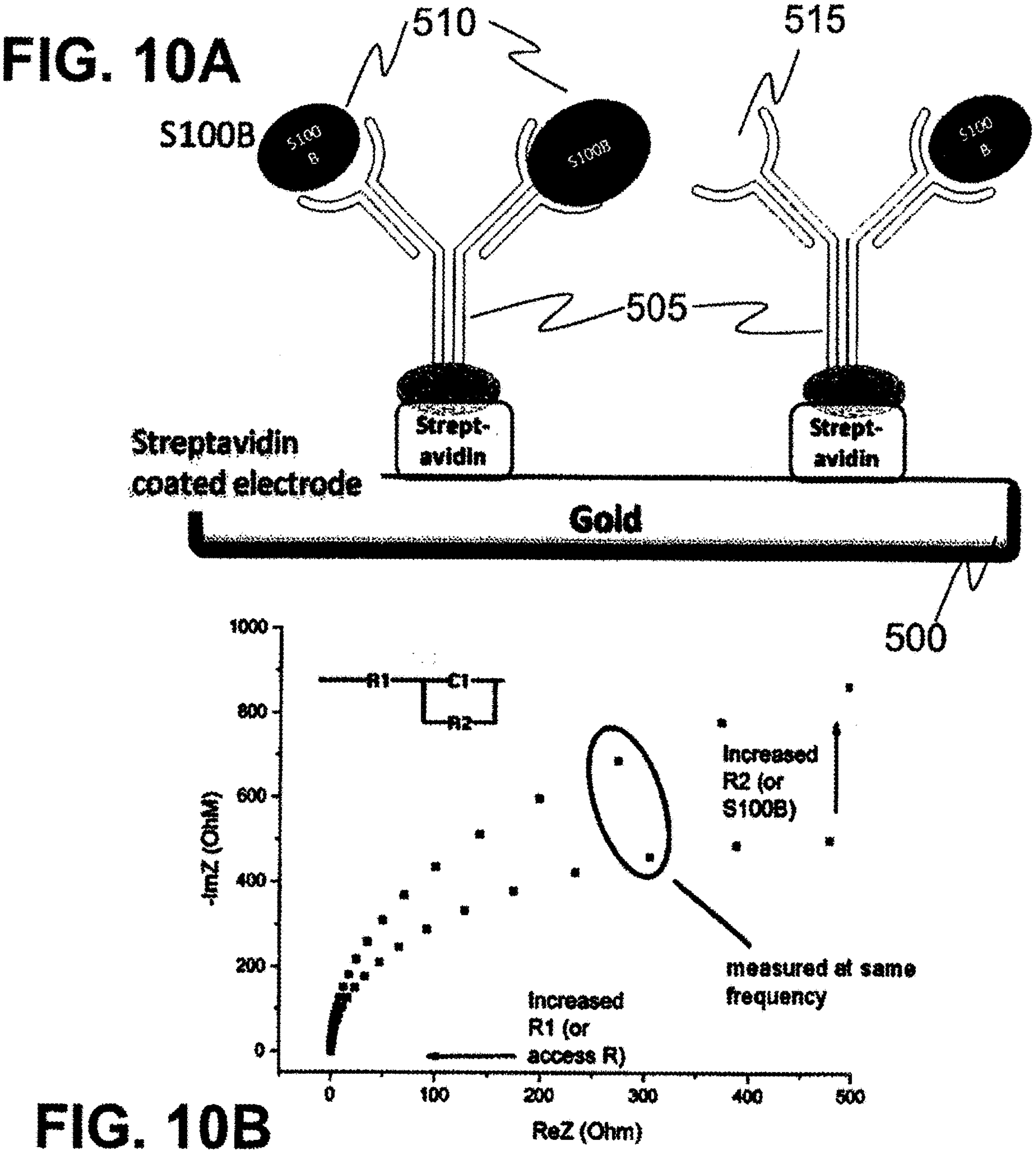
FIGS. 10A-B. A) Diagram of an example assay technique utilized in various embodiments of the present invention, and B) Randles diagram showing an increase in S100b R2 as S100B attaches to binding sites of a capture antibody.

FIGS. 10A and 105B depict another assay technique that may be used in accordance with the present invention utilizing label-free detection of S100B or other analytes. FIG. 10A shows the arrangement of the assay components, similar to the arrangement of the assay in FIG. 9, but wherein no label, enzyme or secondary antibody are required. The working electrode 500 in the present embodiment is coated by streptavidin or a comparable binding agent, which binds another example of capture antibody 505 which may be used for the assays of the present invention. The capture antibody is made available to bind with the target analyte or marker 510 (e.g., S100B) in a manner similar to the embodiment in FIG. 9, and the reaction of this binding is measured by sensors (not shown). FIG. 10B shows a simplified Randles diagram that shows that as S100B attaches to the binding sites, R2 is expected to increase.

In a further embodiment of the invention, a method is disclosed for real-time detection of a signal performing electrochemical impedance spectroscopy (EIS) procedures to generate a set of impedance-related data for the working electrode. According to another embodiment of the invention, a method for real-time detection of a signal dip for a working electrode of a sensor comprises periodically performing an electrochemical EIS procedure to obtain values of real impedance for the electrode; monitoring the values of real impedance over time; and, based on the values of real impedance, determining the concentration of the analyte.

In yet another embodiment of the invention, a sensor system includes a subcutaneous or implanted sensor with one or a plurality of independent working electrodes, a counter electrode, and a reference electrode, and sensor electronics operably coupled to the sensor. The signal is detected by sensor electronics to selectively perform an electrochemical impedance spectroscopy (EIS) procedure. The concentration of the analyte is obtained from impedance data from the working electrodes. The procedure is gated by a programmable microcontroller configured to provide a start and a stop stimulus for the EIS procedure; and an interface configured to operably couple the sensor electronics to a microcontroller and signal detection systems.

Figure 11:
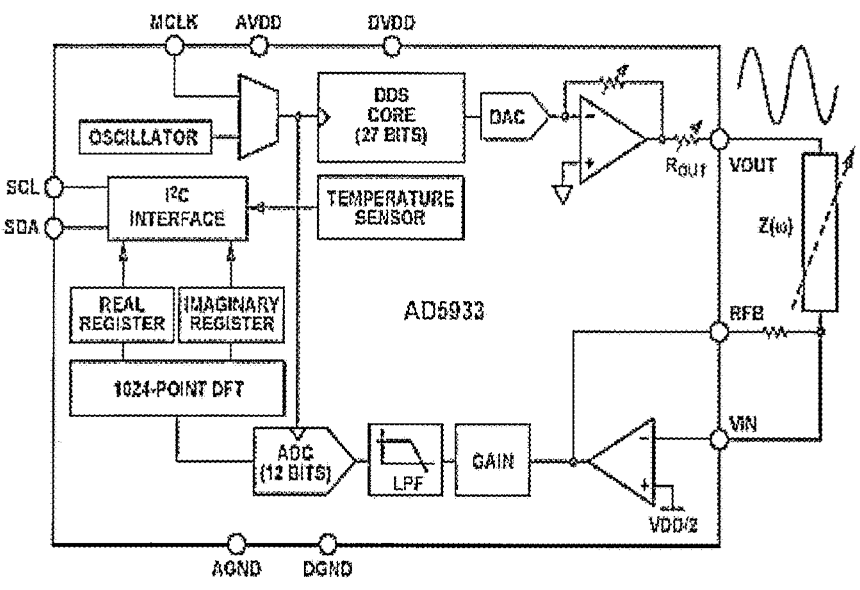
FIG. 11. Electrical schematic of one embodiment of a POC assay device.

FIG. 11 depicts an exemplary electrical schematic of one embodiment of a POC assay device for direct detection of an electrochemical reaction output resulting from the reaction between a target marker or analyte in a sample and a binding agent or reagent added to the sample. As described herein, the reaction of the target analyte or marker binding to an antibody or other compound in the binding agent or reaction produces an output which is an electrical charge. This electrical charge output can be measured as a change in voltage between two sensors in the system where such voltage change corresponds directly to the concentration of the target analyte or marker in the sample.

Figure 12:
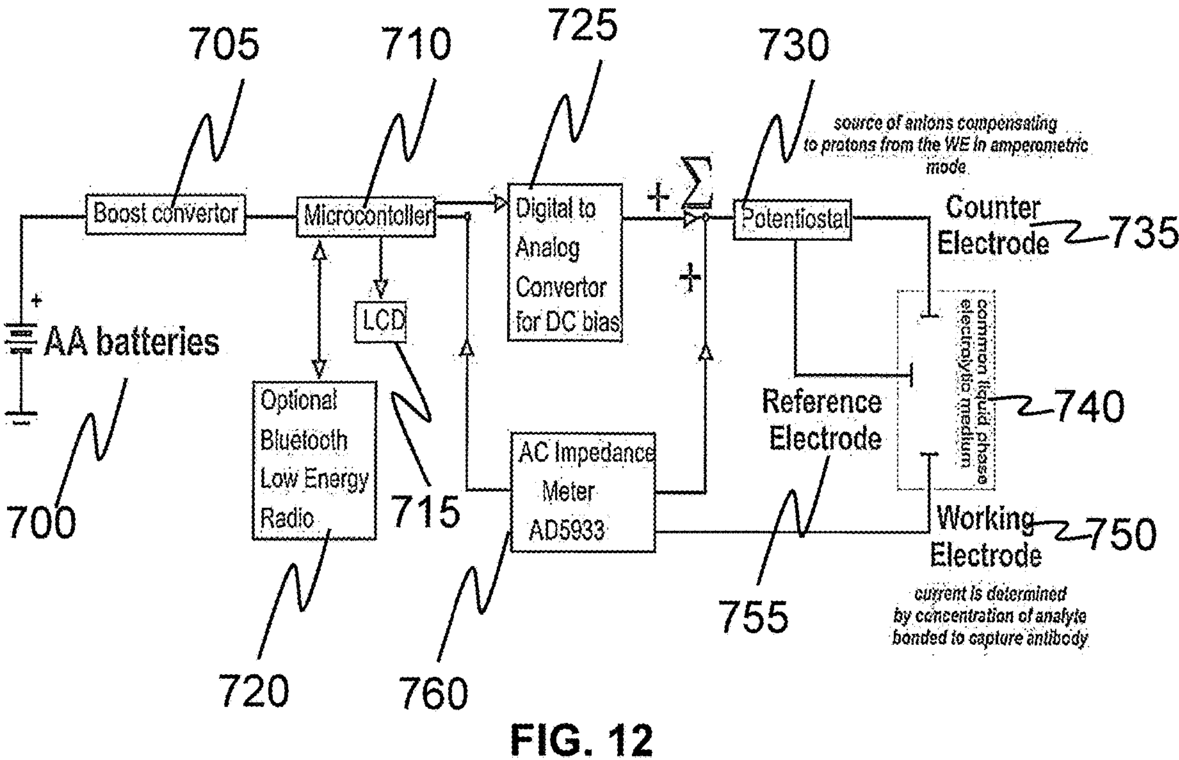
FIG. 12. Block diagram describing one embodiment of a POC assay device.

FIG. 12 depicts a block diagram describing an exemplary embodiment of a POC assay device. The depicted embodiment comprises a power source 700 (e.g., batteries to aid in portability of the POC device), a microcontroller 705 which may include a display 715 (e.g., LCD, LED, etc.) and/or a communications component 720 (e.g., wireless radio transmission—low energy radio, Bluetooth, etc.) for communication with other devices as described herein (e.g., computer, tablet, cell or smart phone, or the like), a digital to analog converter 725, a potentiostat 730, a series of sensors for measuring the reactions within the system including a counter electrode 735, a working electrode 750 and a reference electrode 755, each of which is in connection with the others through a common liquid phase electrolytic medium 740 disposed within the sensing chamber(s) of the device, and an alternating current impedance meter 760. Each of these components is optional and may or may not be included in the various embodiments of the present invention, but are depicted as an exemplary embodiment generally describing the POC device.

Figure 13:
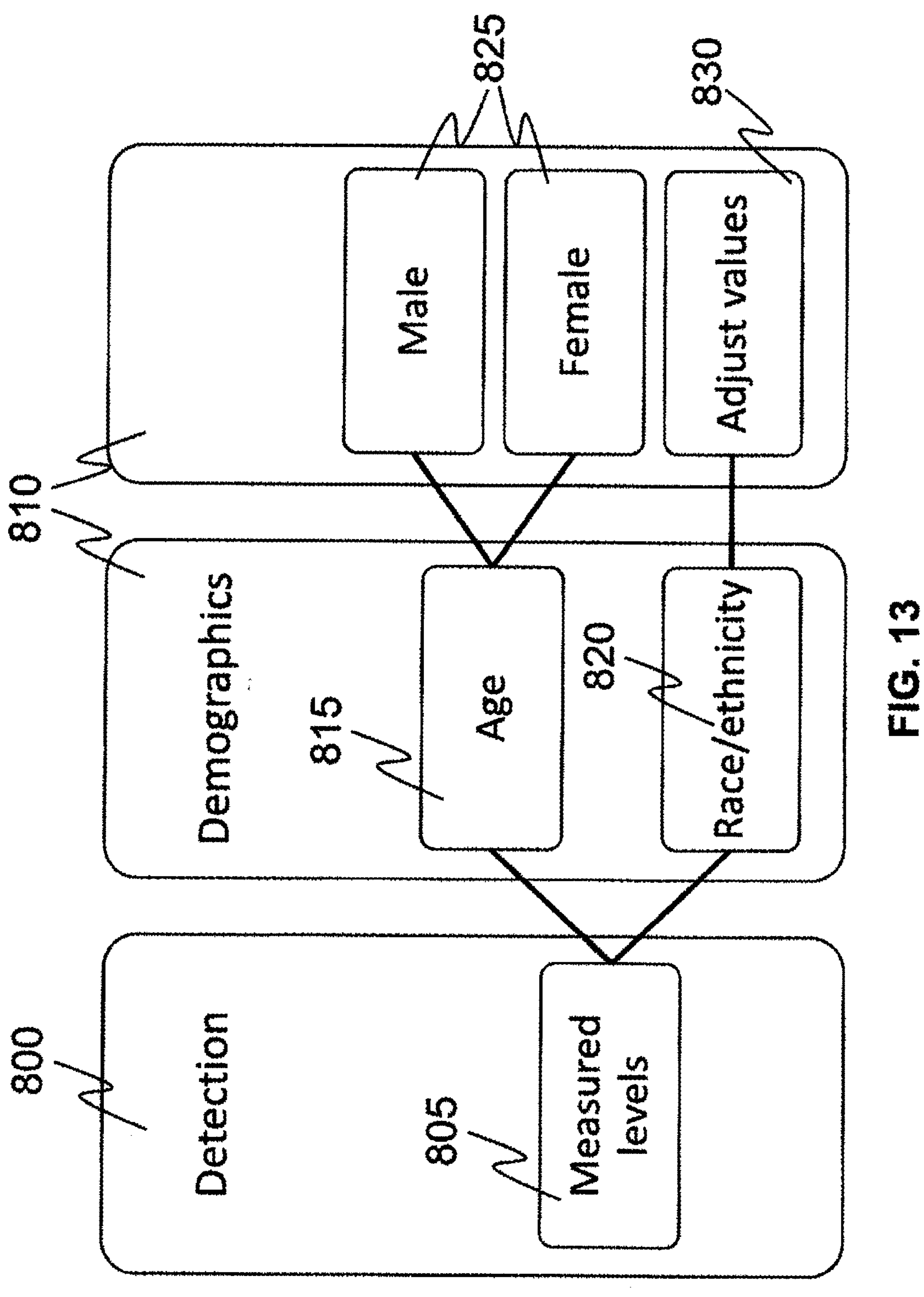
FIG. 13. Flow chart of an algorithm employed in certain embodiments of the present invention showing how measured levels of peripheral markers of blood-brain barrier disruption can be affected by age, gender, and race/ethnicity.

FIG. 13 depicts a flowchart describing an algorithm used in accordance with the present invention in various embodiments whereby patient-specific information is input and utilized to analyze the measured results from the patient's sample due to the fact that measured levels of peripheral markers of BBB barrier disruption can be affected by patient-specific information. In the detection phase 800, the POC assay device is used to measure actual concentrations of at least one target analyte or marker contained in the sample(s) taken from the subject. The system outputs actual measured levels 805, but these measured levels must be interpreted in light of the patient-specific information 810 that affects the results. A patient's age 815, race and/or ethnicity 820, and sex 825, and the like, all affect the measured levels 805 and must be taken into consideration. Once the patient-specific information 810 is input into the system, the algorithm adjusts the measured levels 805 to more accurately reflect the patient's levels based on his or her specific, individualized history, genetics, and the like.

Figure 14:
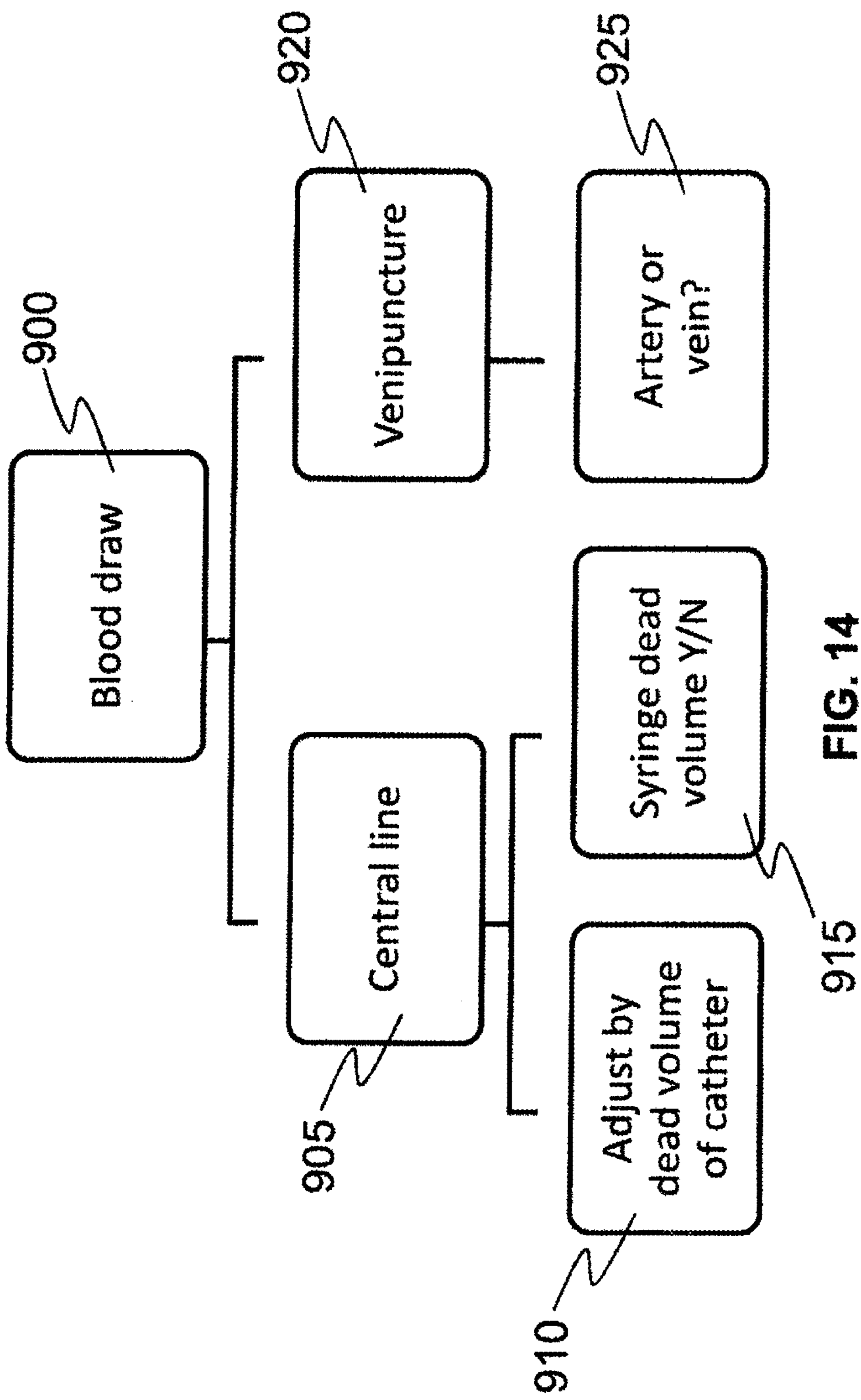
FIG. 14. Flow chart of an algorithm employed in certain embodiments of the present invention showing how measured levels of peripheral markers of blood-brain barrier disruption can be affected by the manner in which the biological fluid sample was obtained.

FIG. 14 presents a flow chart of an algorithm used in accordance with the present invention in various embodiments depicting how peripheral measures of BBB disruption are affected by the manner in which the biological fluid sample was obtained. In this exemplary embodiment, the sample taken from the patient is a blood sample 900. The manner in which the blood was taken from the patient can affect the measured levels of the target marker or analyte in the sample. For example, if the blood sample 900 was taken from a central line 905 the measured values may be adjusted based on the dead volume of a catheter 910 of the central line and/or by syringe dead volume 915. Similarly, if the blood sample 900 is taken via large vessel puncture 920, the sample may be affected by whether it was taken from an artery or vein 925. Each of these inquiries may alter the analysis based on the expected concentration of the analyte or marker at the location from which the sample was taken based on the distance from the BBB, the circulation rate of blood, and other such factors that may alter the expected results.

Figure 15:
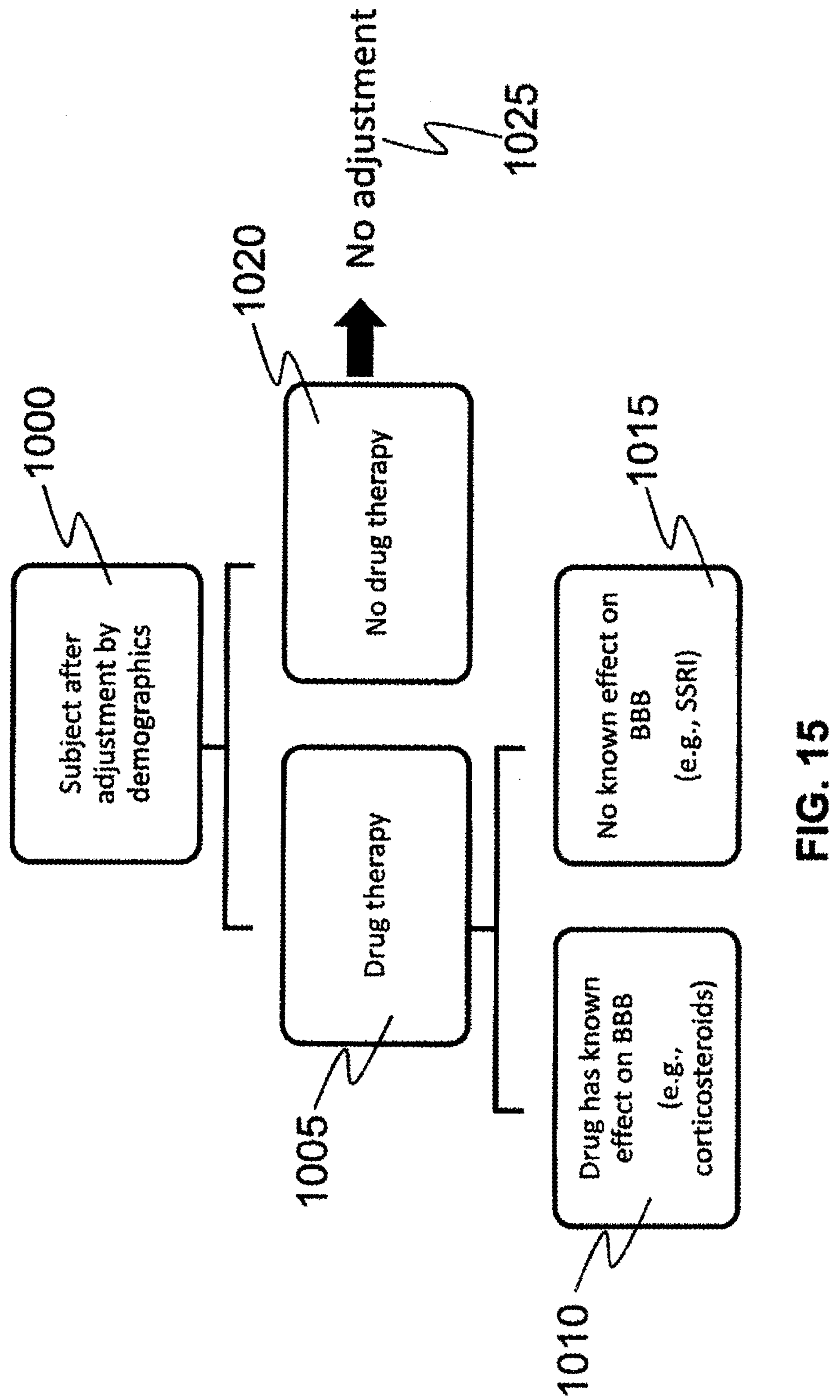
FIG. 15. Flow chart of an algorithm employed in certain embodiments of the present invention showing how measured levels of peripheral markers of blood-brain barrier disruption can be affected by the type of drug therapy that the patient is undergoing.

FIG. 15 presents a flow chart of an algorithm used in accordance with the present invention in various embodiments depicting how peripheral measures of BBB disruption are affected by various types of drug therapies (as another form of patient-specific information) the patient is undergoing. The depicted portion of the adjustment algorithm takes into account the measured levels of the marker after being adjusted by demographic information 1000. The next level of input asks whether the subject is undergoing any form of drug therapy 1005 or is receiving no drug therapy 1020. If there is no drug therapy, then no adjustment is required 1025. If the patient is undergoing drug therapy(ies) 1005, then that particular drug(s) known effect on BBB 1010 can be input into the system to adjust the levels accordingly (e.g., corticosteroids have a known effect on the BBB), or the system can determine how to adjust (or not adjust) the levels based on a drug therapy whose effect on BBB is not known (1015.

Figure 16:
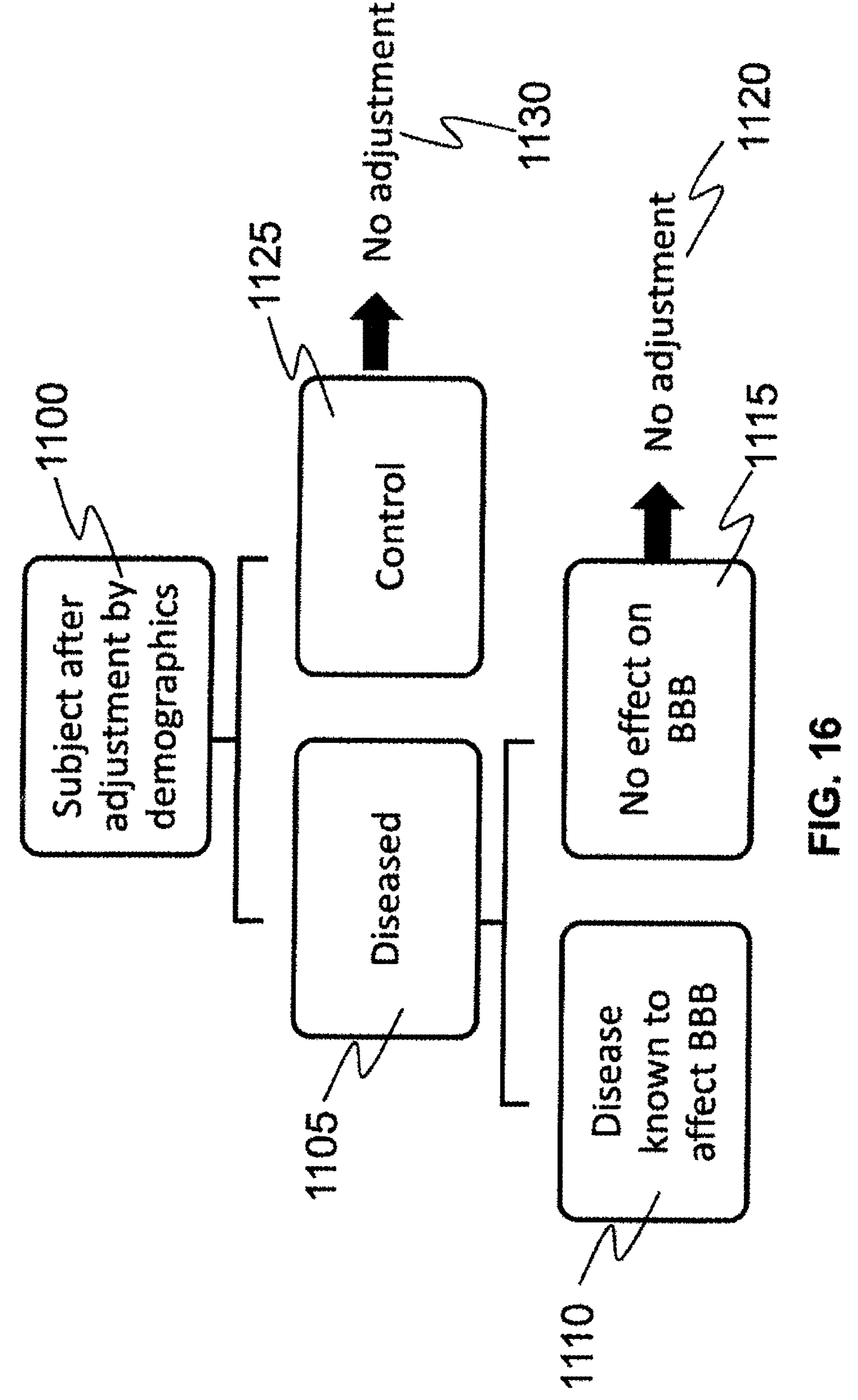
FIG. 16. Flow chart of an algorithm employed in certain embodiments of the present invention showing how peripheral measures of BBB disruption are affected by various disease states of a patient.

FIG. 16 presents a flow chart of an algorithm used in accordance with the present invention in various embodiments depicting how peripheral measures of BBB disruption are affected by various disease states of a patient. After the measured levels have been adjusted based on patient-specific information 1100, another input is any disease state the particular patient may be in. If there is no disease state or the subject is normal 1125, then no adjustment 1130 to the measured levels of the analyte or marker are required. However, if the patient is in a diseased state 1105, the particular disease state may have a known effect on the BBB 1110, in which case the measured levels may be adjusted based on the known effect, or may have no effect on the BBB 1115, in which case no adjustment 1120 is required.

Figure 17:
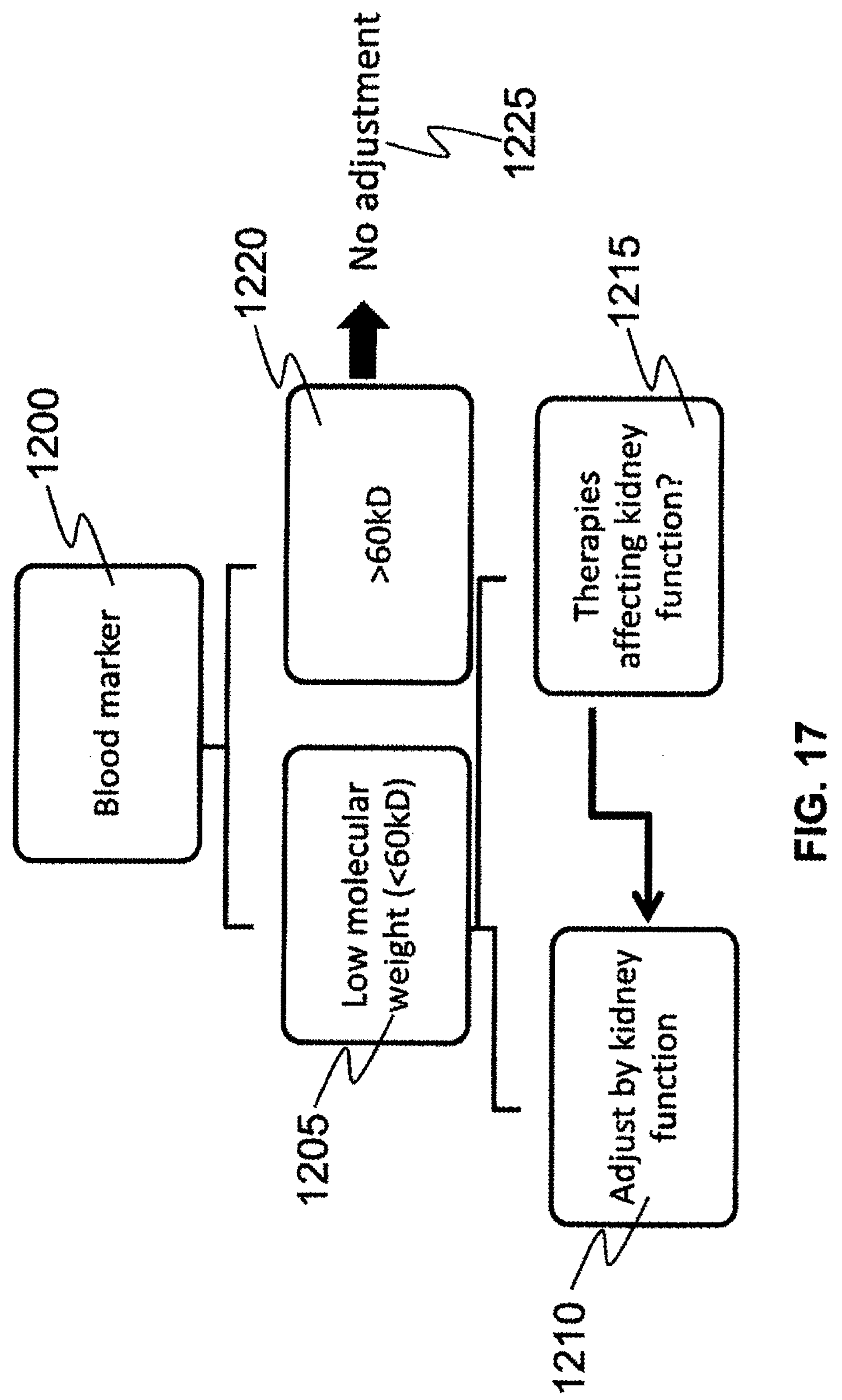
FIG. 17. Flow chart of an algorithm employed in certain embodiments of the present invention showing how peripheral markers of BBB disruption are affected by the molecular weight of the target analyte or marker.

FIG. 17 presents a flow chart of an algorithm used in accordance with the present invention in various embodiments depicting how peripheral measures of BBB disruption are affected by the molecular weight of the target analyte or marker. The target analyte or marker 1200 used in the assay is a known quantity with a known molecular weight. Based on the patient-specific information, particularly kidney function and the kidneys' ability to filter out the analyte or marker through circulation of the blood, the measured levels of the analyte or marker may need to be adjusted. For a normal functioning patient's kidney, for example, an analyte or marker with a molecular weight of greater than 60 kD 1220 likely requires no adjustment to the measured levels as they are unlikely to be filtered out by the kidneys and thus lost to analysis. If the analyte or marker has a molecular weight less than approximately 60 kD 1205, for example, then the measured values of the analyte or marker may need to be adjusted based on the patient's kidney function 1210. This adjustment may further be affected by any therapies 1215 the subject may be undergoing that affect kidney function. Nonetheless, this is another form of patient-specific information that must be taken into account by the algorithm.

Figure 18:
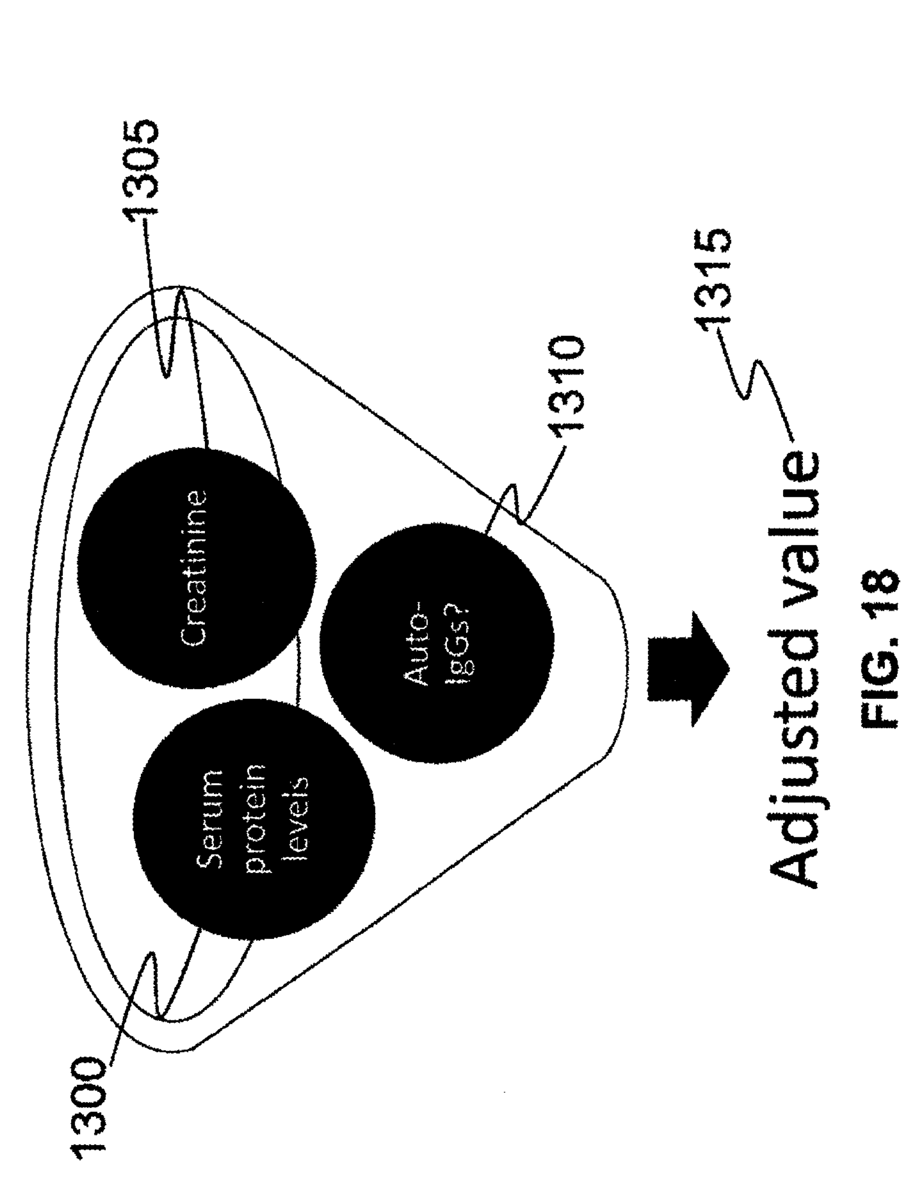
FIG. 18. Illustration of an algorithm employed in certain embodiments of the present invention showing how measured levels of peripheral markers of blood-brain barrier disruption can be affected by serum protein levels, creatinine, and antibody levels of the patient.

FIG. 18 presents an illustration of an algorithm used in accordance with the present invention in various embodiments depicting how peripheral measures of BBB disruption are affected by various inputs or factors. Effectively, a large number of inputs or factors specific to the patient, including compounds normally present in the patient's blood or serum, affect the measured values of the target analyte or marker and must be considered when determining the actual concentration level output by the algorithm. Serum protein levels 1300, creatinine 1305 and antibodies already present normally in a patient's blood effect the measured values of the target analyte or marker, and all preferably are taken into account by the algorithm in determining the adjusted values 1315 of the target analyte or marker concentration.

Figure 19C:
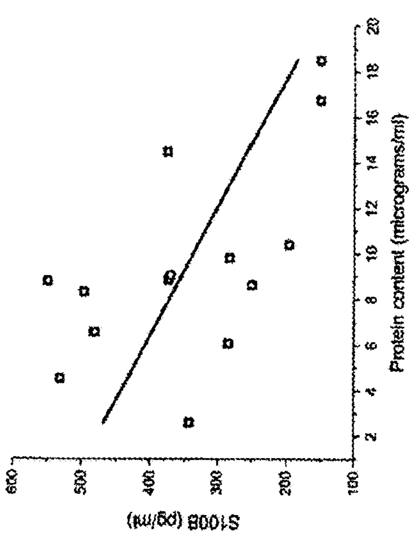
FIGS. 19A-C. Graphs depicting the effect of hemodilution and protein content of serum on measured concentrations of the BBB disruption marker S100B where A) all measured values of S100B are shown B) only S100B values less than 150 μg/ml are shown, and C) only S100B values greater than 150 μg/ml are shown.
Figure 19B:
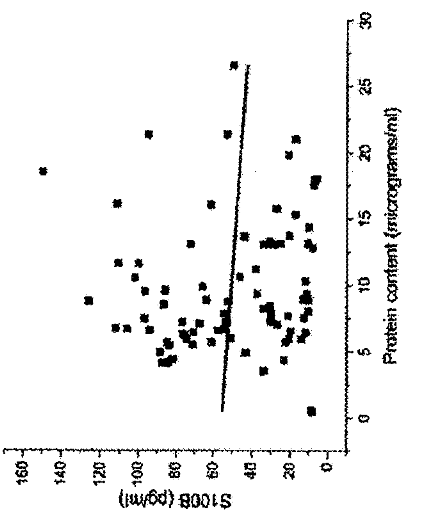
Figure 19A:
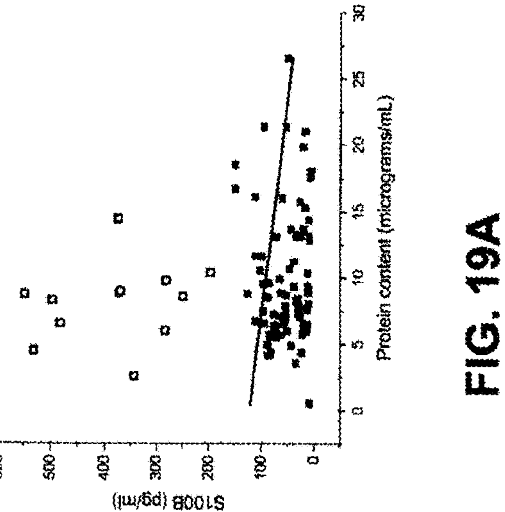

FIG. 19A is a graph depicting the effect of hemodilution and protein content of serum on measured concentrations of the BBB disruption marker S100B. The fit gave a relationship S100B=122−3.06*Protein content. The relationship was not statistically significant. FIG. 19B is a graph depicting the effect of hemodilution and protein content of serum on measured concentrations of the BBB disruption marker S100B. Only values of S100B<150 μg/ml are shown. The fit gave a relationship S100B=54−0.48*Protein content. The relationship was not statistically significant. FIG. 19C is a graph depicting the effect of hemodilution and protein content of serum on measured concentrations of the BBB disruption marker S100B. Only S100B values>150 μg/ml are shown. The fit gave a relationship S100B=514−17*Protein content. The relationship was statistically significant ($p=0.02$).

Figure 20:
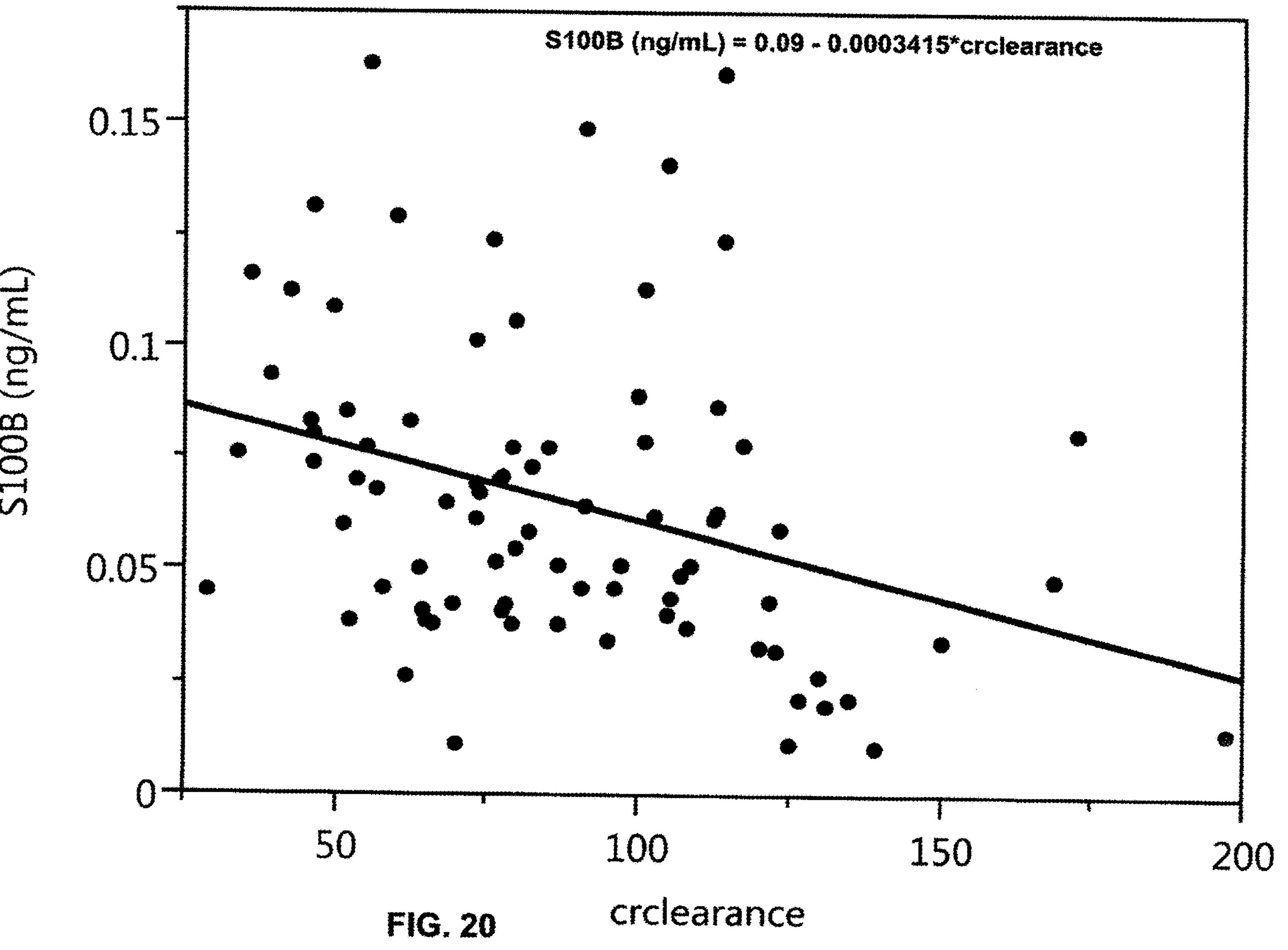
FIG. 20. Graph depicting the effect of creatinine clearance and kidney function on measured concentrations of the BBB disruption marker S100B.

FIG. 20 is a graph depicting the effect of creatinine clearance and kidney function on measured concentrations of the BBB disruption marker S100B. The fit shows S100B (ng/mL)=0.0954183−0.0003415*$cr_{clearance}$.

Figure 21:
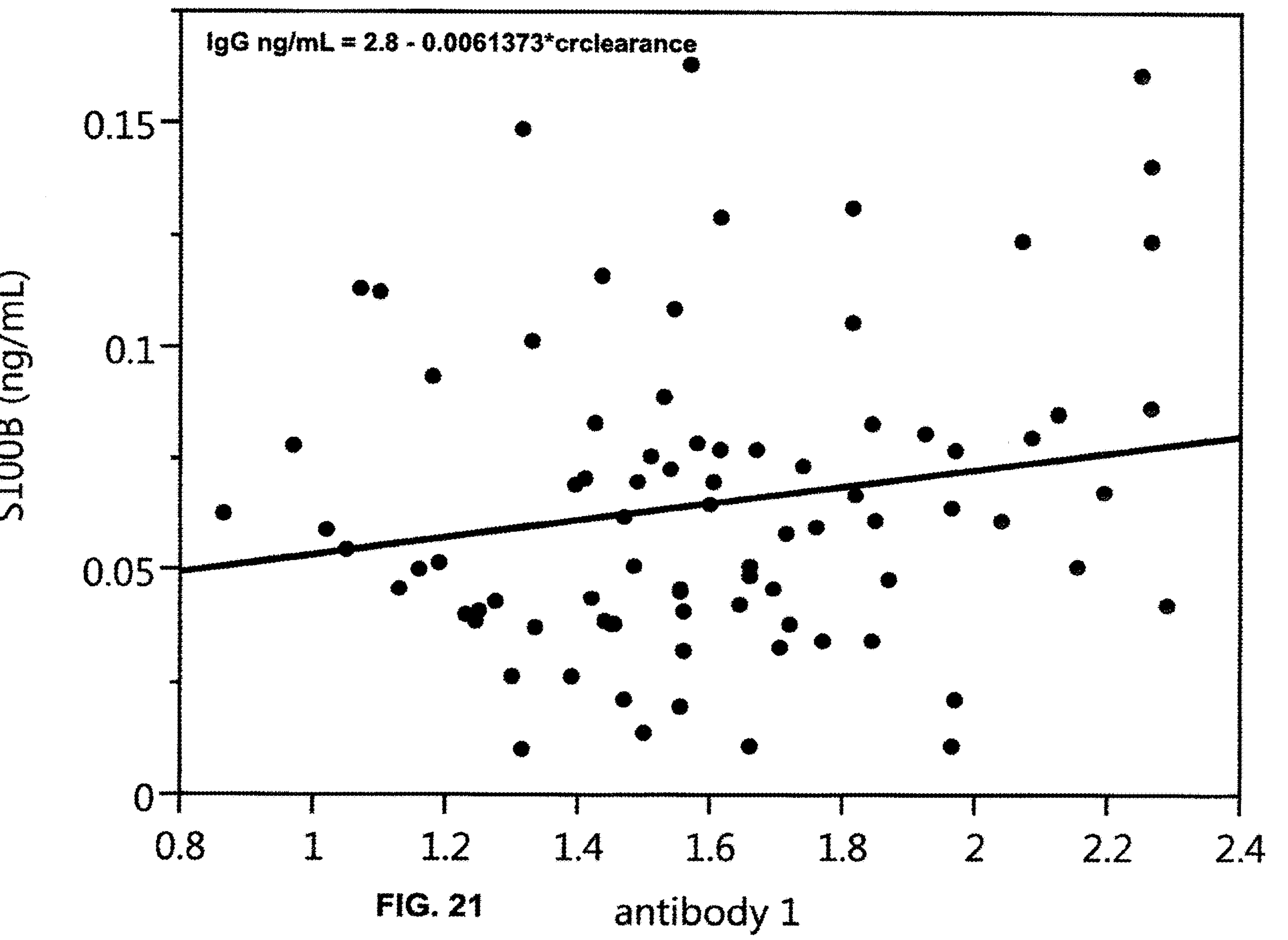
FIG. 21. Graph depicting the effect of anti-S100B serum antibodies on measured concentrations of the BBB disruption marker S100B.

FIG. 21 is a graph depicting the effect of anti-S100B serum antibodies on measured concentrations of the BBB disruption marker S100B. The line is fit by S100B (ng/mL)= 0.0346366+0.0192986*antibody 1.

FIGS. 22A-D, together, depict various considerations taken into account in developing a pharmacokinetic model for using measured values of peripheral blood biomarkers to assess brain health and detect neurological conditions. The various subparts of the figure provide region-specific groupings of all initial assignments and assumptions considered in a kinetic model of biomarker distribution used in development of the present invention. FIG. 22A includes parameters incorporated into the Central Nervous System (CNS). Biomarker initial assignments 1700 included molecular weights for the biomarkers selected to use which included S100B, S100BB, GFAP, and UCHL-1. CNS initial assignments 1705 are also depicted, and are separated into brain volume and blood volume values for infants and adults. CNS initial assignments 1705 for adults are further separately defined for male and female adults. Blood-brain barrier initial assignments 1710, included BBB permeability values and are also delineated between infants and adults. These initial assignments were used to produce a model for mimicking the passage of biomarkers from the brain across the blood-brain barrier, into circulation, and through filtration and removal from the body, such as through kidney filtration and passing with urine. FIG. 22B depicts assumptions and results of extracranial contributions to serum concentrations of the biomarker S100B. Initial assignments for extracranial biomarker sources 1725 were made including the assumption that biomarkers are only intracellular and steady-state rate of leakage from cells to blood is essentially equal to the ratio of transfer from brain to blood. More specifically, extracranial sources of S100B were quantified using published data and each organ's rate of transfer to blood was set to a fixed rate of 1-5%. Thus, the leakage 1730 of biomarkers from cells into the blood was tested using the model in order to test the hypothesis that extracranial contributions to serum biomarker levels do not significantly differ from a model whose only contributions are from the brain—in other words, elevated levels of cranial biomarkers in the blood is likely not affected by leakage of such biomarkers from non-cranial cells. The bar graph 1735 shows organ-specific contribution to serum levels of S100B according the model. Multiple data points for skin are presented in order to represent the difference between complexion or ethnicity and the effect such characteristic has on serum S100B concentrations. FIG. 22C represents the initial assignments where arterial and venous blood volumes were combined into a common, systemic blood compartment, and the initial assignments for circulated biomarker concentrations 1750 were that venous concentrations were effectively equivalent to arterial concentrations. The initial value for biomarker concentration in this blood compartment was 0 ng/ml. Kidney initial assignments 1755 included various glomerular filtration rates (GFR) based on gender and race. FIG. 22D depicts the passage of biomarker mass 1770 into the kidneys 1775, and from the kidneys passed from the body via urine 1780. Such passage was dependent on the initial assignment of GFR.

Figures 23A, 23B, 23C, 23D:
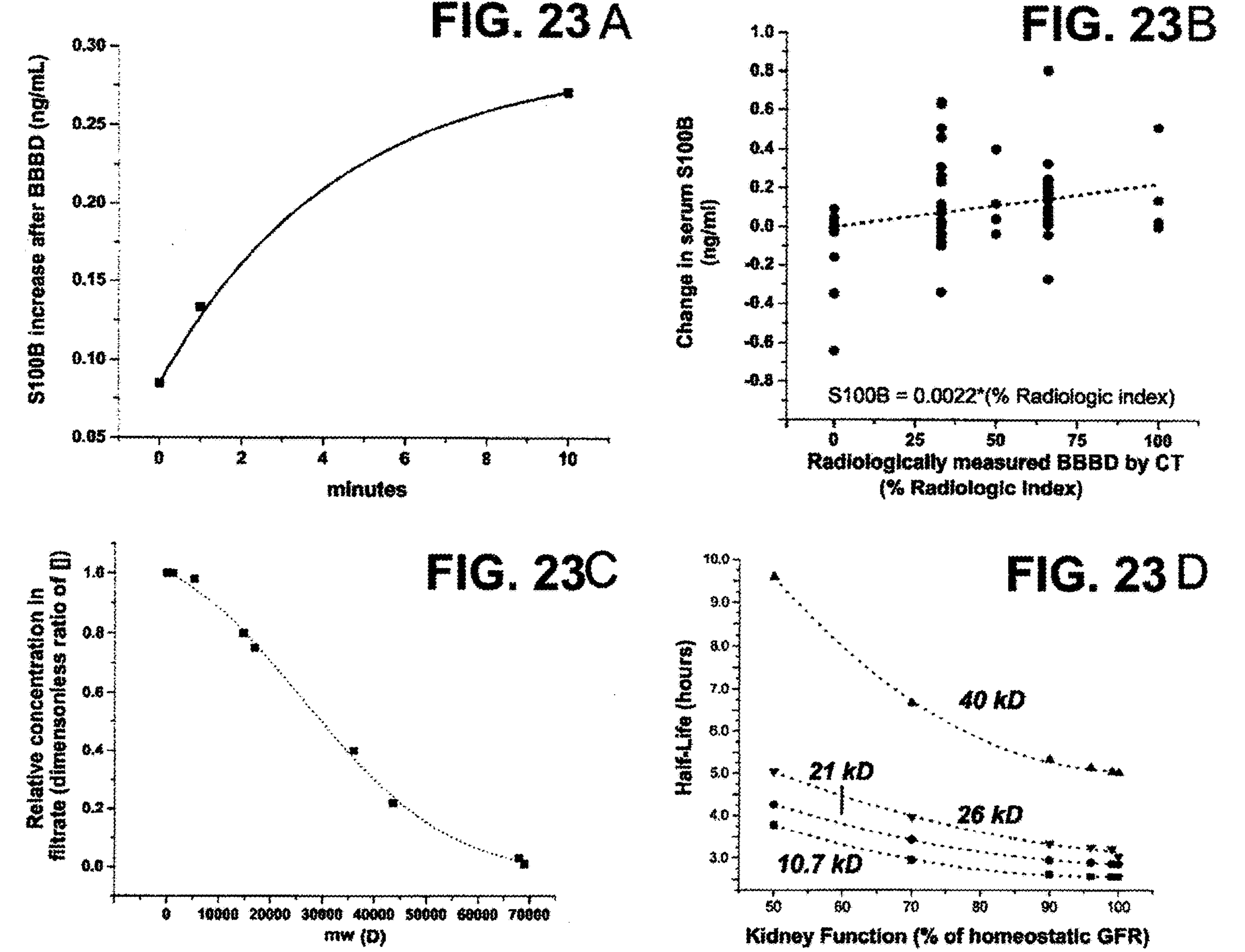
FIGS. 23A-D. Graphs depicting empirical determination of blood-brain barrier characteristics under a pharmacokinetic model for peripheral blood biomarkers, and quantitative assessment of molecular weight on serum biomarker levels.

FIGS. 23A-D are graphs depicting the empirical determination of blood-brain barrier characteristics under a pharmacokinetic model for peripheral blood biomarkers, and quantitative assessment of molecular weight on serum biomarker levels. The kinetics of blood-brain barrier disruption (BBBD) in the model were derived from empirical data of previous studies that involved human patients receiving artificial, osmotic opening of the barrier. Time-dependent opening of the BBB was modeled in accordance with Equation 1. FIG. 23A shows the time course of serum S100B elevation after intra-arterial infusion with 1.6 M mannitol. The extent at which serum S100B levels were affected by BBBD was modeled in accordance with Equation 2 where a radiologic scale of BBB opening shows that 0% BBBD promotes no change in serum S100B, while maximal BBBD causes an increase of ~0.22 ng/ml in serum S100B (FIG. 23B). In this case, the hyperosmotic mannitol solution was perfused through the internal carotid artery (ICA). In addition to glomerular filtration rate, a biomarker's Filtration Coefficient (CF) determined the rate at which a marker is cleared through the kidneys in accordance with Equation 3, with proteins of higher molecular weight had a lower turnover rate from blood into urine (FIG. 23C). FIG. 18D demonstrates the dependency of biomarker half-life on molecular weight, as well as renal function. Proteins of higher molecular weight will experience a longer half-life in blood overall, but all biomarkers will show an exponential increase in half-life as a result of diminished renal function.

Figure 24A:
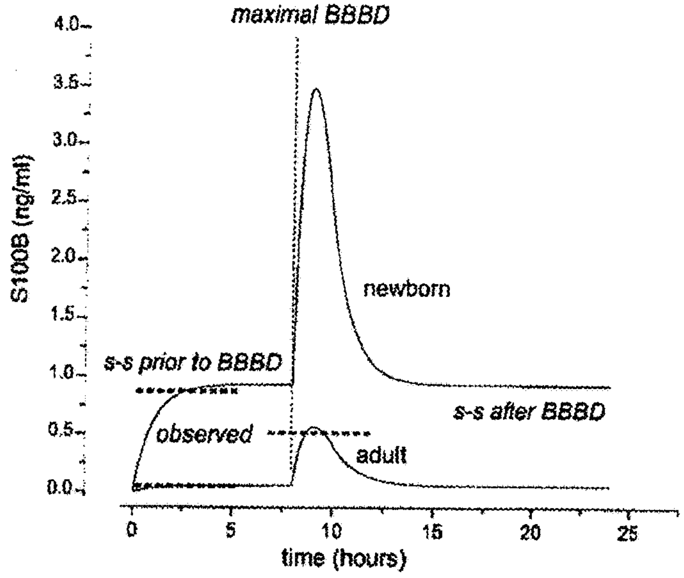
FIGS. 24A-C. Graphs depicting predicted differences in biomarker kinetics between patients of varying age based on glomerular filtration rate, body size, and steady-state blood-brain barrier function.
Figure 24B:
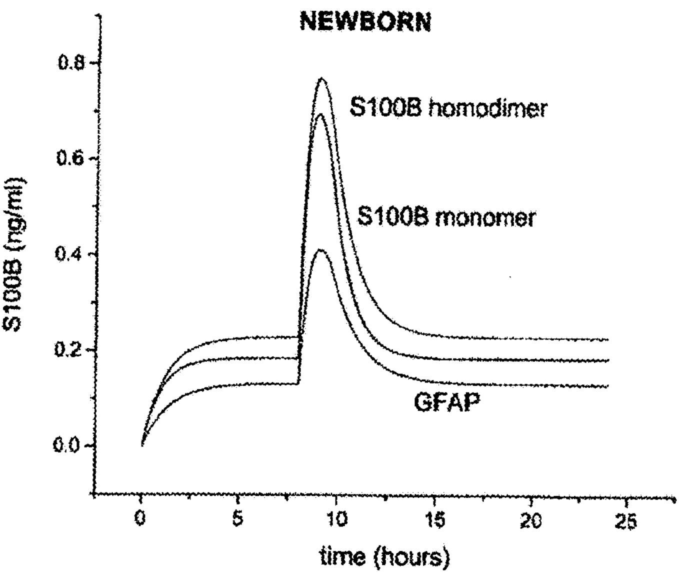
Figure 24C:
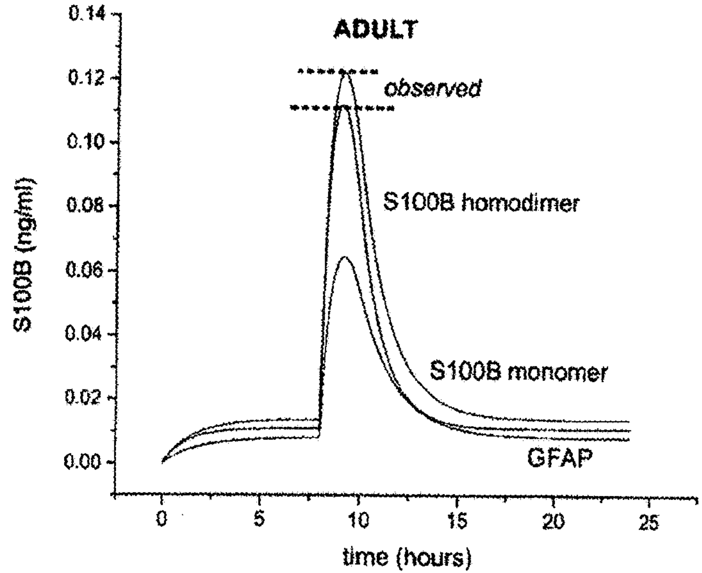

FIGS. 24A-C are graphs depicting predicted differences in biomarker kinetics between patients of varying age based on glomerular filtration rate, body size, and steady-state blood-brain barrier function. FIG. 24A demonstrates, for steady-state S100B levels in blood, a ~16-fold increase for newborns compared to adults (0.92 ng/ml and 0.055 ng/ml, respectively). After maximal BBBD, newborns presented a more dramatic increase in serum S100B concentrations. The horizontal dashed lines in FIG. 24A show a consistency between the observed levels and results from prior literature, for steady-state as well as maximal BBBD in adults. FIGS. 24B and 24C show the behavior for serum levels of the homodimeric form of S100B (21 kD), as well as GFAP (26 kD) and S100B monomer. The concentration profiles in a newborn, as depicted in FIG. 24B, show a significantly increased steady-state and post-BBBD serum level for all biomarkers, compared to an adult, as depicted in FIG. 24C. The differences among markers within a neonatal or adult population was entirely attributed in the model to GFR values. The horizontal dashed lines in FIG. 24C again show consistency between model predictions and results from previous studies.

Figure 25:
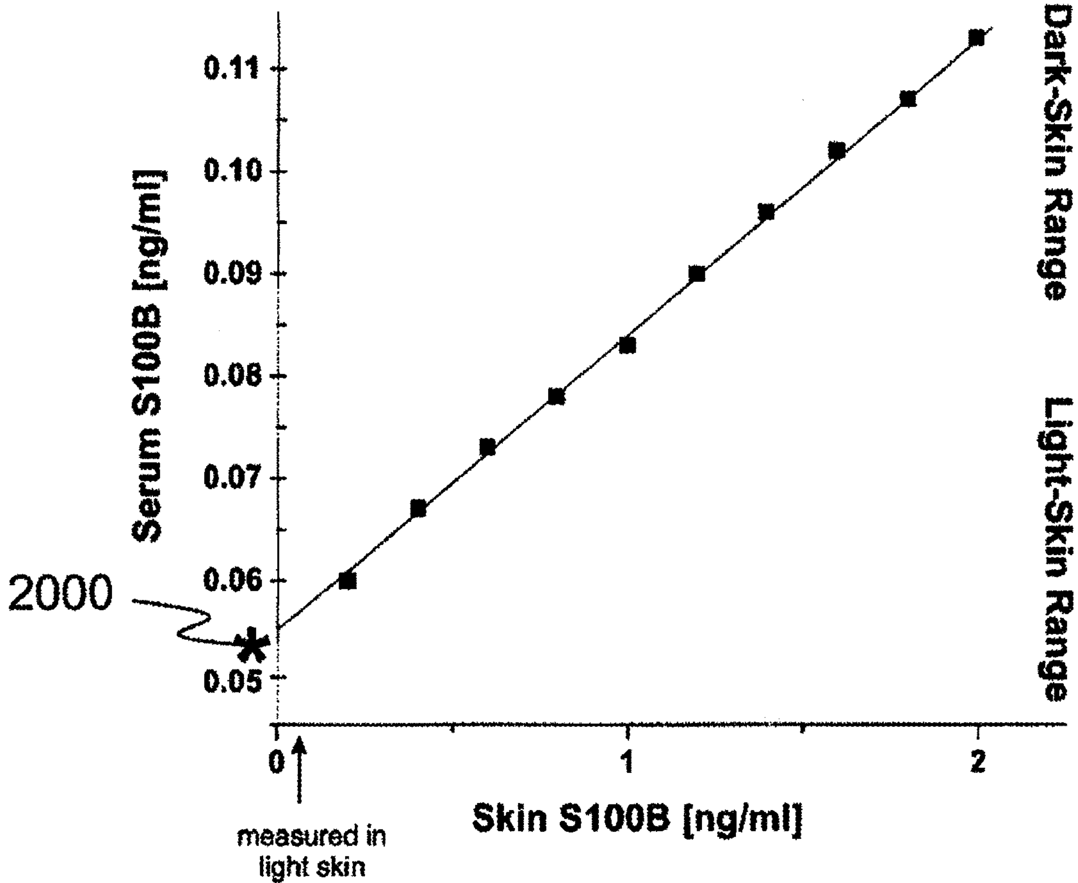
FIG. 25. Graph depicting predicted differences in serum S100B levels as a result of skin pigmentation.

FIG. 25 is a graph depicting predicted differences in serum S100B levels as a result of skin pigmentation. The model described above was used to test the hypothesis that different levels of serum S100B between ethnicities could be explained by skin's contribution to S100B levels under steady-state conditions regardless of the genetic background of an individual. When the initial parameters shown in 22B were used, these parameters predicted a serum S100B level of 0.065 ng/mL for light-skinned subjects, which is comparable to previously recorded findings within this subpopulation 2000. A realistic level for skin S100B was used, which was taken from previous studies and the data in FIG. 22. In order to output accurate serum S100B levels for dark-skinned subjects, the model required that skin concentration of S100B be increased to above 2.0 ng/mL, which resulted in a serum concentration of 0.115 ng/mL; this supports the hypothesis that differences in S100B between subgroups of different ethnicity can be explained as a consequence of increased S100B concentration in the skin, and thus, an augmented contribution from the skin to blood. This implies that any change in a subject's skin pigmentation (e.g., tanning) will increase levels of S100B. With no discernment for ethnicity, the differences in serum S100B levels are perfectly explained as directly dependent on skin pigmentation and sun exposure, which in turn leads to darkened pigmentation.

Figure 26:
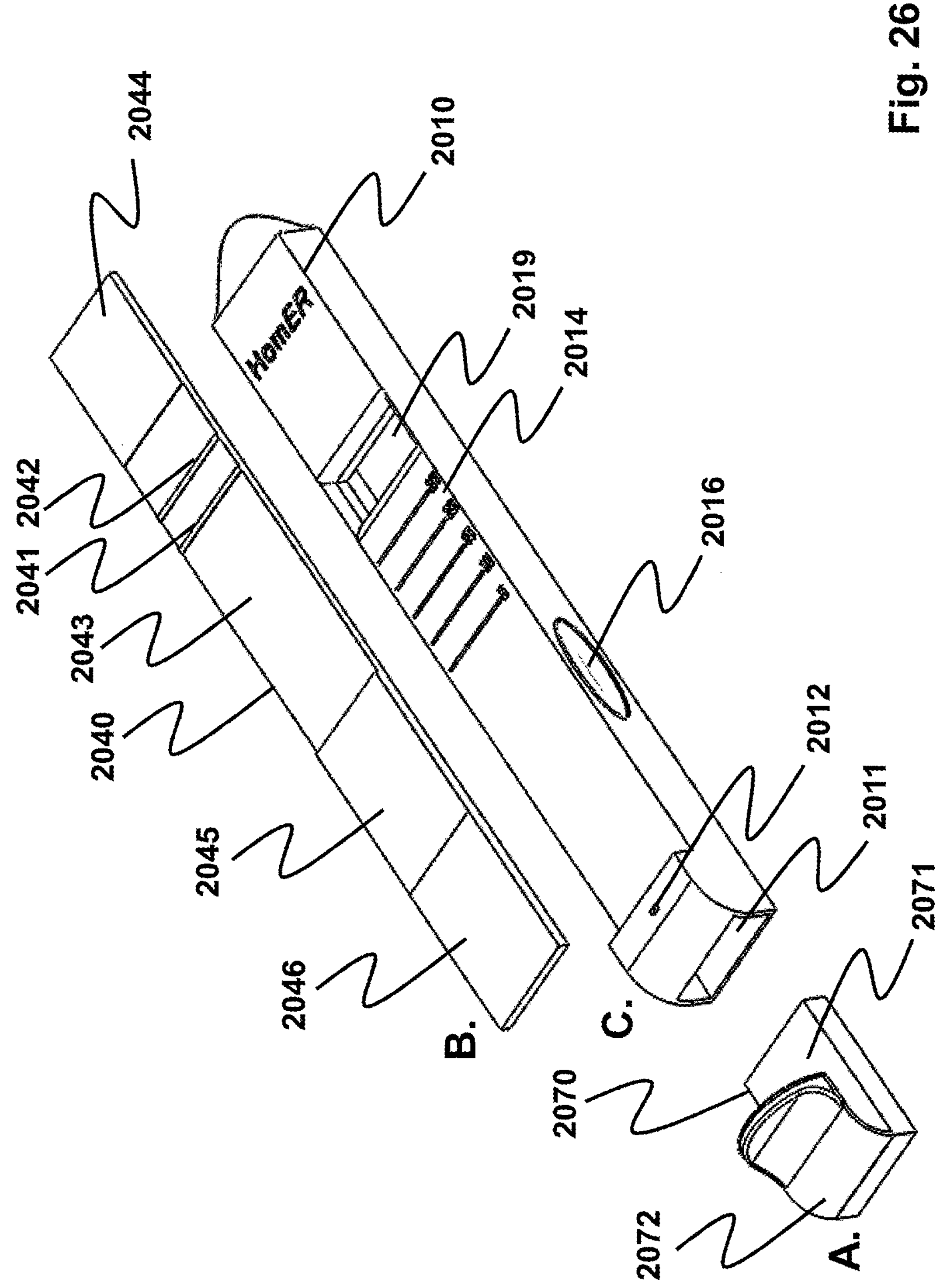
FIG. 26. Perspective view of a first embodiment of a test cartridge showing the cartridge's A) collection cap; B) internal test strip; and C) the body of the cartridge with the test strip inserted.

FIG. 26 is a perspective view of a first embodiment of a test cartridge. FIG. 26A. shows a removable cap 2070 which is part of the test cartridge system and contains a cotton collection pad 2071. In this embodiment the cotton collection pad 2071 is attached to a grooved handle 2072, which is used to remove from and insert the collection pad 2071 into the test strip housing 2010. The grooved handle 2072 can further function to hold the collection pad 2071 in place in a subject's mouth until enough saliva sample is available for the removable cap 2070 to be reinserted into the cartridge or test strip housing 2010. FIG. 26B. shows the test strip 2040, which is housed in the cartridge or test strip housing 2010. The test strip 2040 is comprised of a detection band 2041 with immobilized analyte-targeting reagents, a test band 2042 to ensure the test has been run properly by the user, a nitrocellulose membrane 2043 for transport of the saliva fluid sample toward the detection band, a wicking pad 2044 for controlling transport of the saliva through the nitrocellulose 2043, a conjugate suspension matrix 2045 to retain the analyte primary binding reagent (not shown), and a sampling pad 2046 to either be inserted directly into the subject's mouth or to receive saliva from the collection pad 2071 as it is squeezed as it is inserted into the body of the test strip housing 2010. FIG. 26C. shows the body or cartridge/test strip housing 2010. The body 2010 further features a docking or saliva extraction inlet 2011 for the removable saliva collection pad 2071. The body 2010 further features a cap snap lock 2012 female opening to lock the removable cap 2070 after collecting the saliva sample into the test strip housing 2010 the collection pad is compressed laterally upon reconnection to squeeze saliva onto the test strip 2040. One preferred method is that the inlet 2011 is tapered vertically, horizontally or bi-directionally, which applies enough pressure on the collection pad 2071 to move saliva from the collection pad to the test strip 2018. The grooved handle 2072 contains the male portion (not shown) of this connector to lock the cap 2070 and the body 2010 together. The test strip housing 2010 further includes finger placement indents 2016 to allow the user to better hold the body 2010 and position it while inserting the cap 2070 containing the collection pad 2071 back into the test strip body 2010. The test strip housing 2010 further contains a window 2019 for viewing the reaction on the test strip 2040 as well as calibration lines 2014 to assist in reading and quantifying the results from the test strip 2040.

Figure 27:
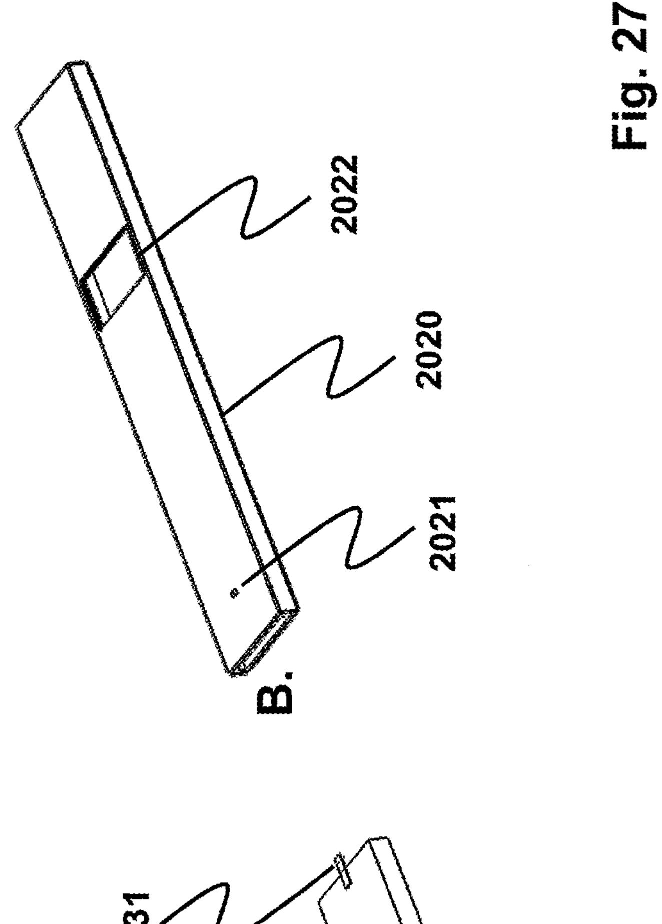
FIG. 27. Perspective view of a second embodiment of a test cartridge showing the cartridge's A) collection cap: B) internal test strip; and C) the body of the cartridge with the test strip inserted.

FIG. 27 is a perspective view of a second embodiment of a saliva test cartridge. FIG. 27A. shows another version of a removable cap 2030 which is part of the test cartridge system. In this embodiment the cotton collection pad 2046 is part of the test strip 2040. Further the removable cap 2030 is strictly used to protect the test strip 2040 from being twisted, compressed or torn. The removable cap 2030 has a male snap connector 2031, which is used to attach the cap 2030 to the female opening 2021 on the test strip housing 2020 after use. FIG. 26B. shows the body or cartridge/test strip housing 2020. The test strip housing 2010 optionally includes finger placement indents (not shown) to allow the user to better hold the body 2020 and position it while inserting the cap 2030 containing the collection pad back into the test strip body 2020. The test strip housing 2020 further contains a window 2022 for viewing the reaction on the test strip 2040 as well as optionally calibration lines (not shown) to assist in reading and quantifying the results from the test strip 2040.

Figure 28:
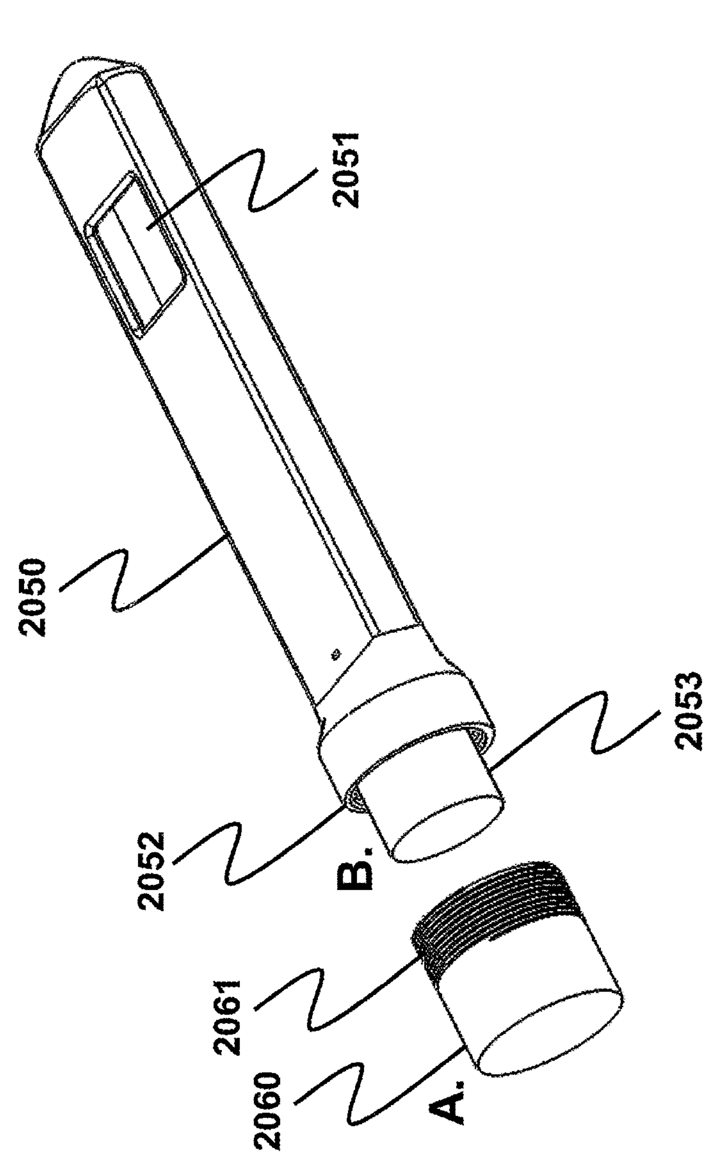
FIG. 28. Perspective view of a third embodiment of a test cartridge showing the cartridge's A) collection cap; and B) the body of the cartridge with the test strip inserted.

FIG. 28 is a perspective view of a third embodiment of a saliva test cartridge. FIG. 28A. shows another version of a removable cap 2060 which is part of the test cartridge system. This cap 2060 is threaded 2061 for attachment via the threads 2052 in the test strip housing 2050. The cap 2060 further can optionally include fill lines (not shown) for indicating to the subject or their care provider the amount of saliva that must be collected or spit into the cap 2060. In this embodiment the cotton collection pad 2053 is part of the test strip 2040. Further the removable cap 2060 is used to collect the saliva and then place the saliva in contact with the test strip 2040. The threaded male opening 2061 of the removable cap 2060 is screwed into the threaded female opening 2052 of test strip housing 2050. FIG. 28B. shows the body or cartridge/test strip housing 2050. The body 2050 further contains a window 2051 for viewing the reaction on the test strip as well as optionally calibration lines (not shown) to assist in reading and quantifying the results from the test strip 2040. Optionally the cylindrical collection pad 2053 can be inserted directly into the subject's mouth using the cap 2060 strictly to protect the collection pad 2053 after collection.

The contents of U.S. Pat. Nos. 6,884,591 and 7,144,708, as well as the contents of all documents and publications cited therein, are expressly incorporated by reference.

While a preferred embodiment is disclosed herein, it will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. An assay system for determining a likelihood that a subject has a neurological condition or to assess brain health comprising:

a test sheet adapted to receive a saliva fluid sample given by a subject;

the test sheet comprising a base layer and at least one binding agent coated onto the base layer, and adapted to elicit a chemical reaction and bind to at least one target marker in the saliva; and the at least one binding agent adapted to bind with the at least one target marker with lower molecular weights no greater than about 60,000 Daltons (Da) and to provide a color change, a fluorescent signal, an infrared signal or chemical luminescence upon binding with a certain quantity of the at least one target marker with the lower molecular weights in the saliva.

2. The assay system in claim 1, further comprising at least one detector comprising an output signal adapted to measure the color change, a fluorescent signal, an infrared signal, or chemical luminescence from the chemical reaction, and being deployed or used in close proximity to the test sheet;

a processor adapted to:

a) receive the output signal from the at least one detector;

b) compare the output signal to a control sample comprising levels of the at least one target marker in a normal population; and c) output a determination based at least in part on the comparison, the determination being a likelihood that the subject has a neurological condition or an assessment of brain health of the subject; and an output device adapted to display or indicate at least the determination.

3. The assay system in claim 2, wherein the assay system is a portable point-of-care system where the test sheet is used once at a point of care or point of injury, and the processor and the output device are part of one or more of a smart phone, a portable computing device or tablet computing device.

4. The assay system in claim 3, wherein the one or more of a smart phone, a portable computing device or tablet computing device further comprises an input adapted to allow a user to input data and/or background information related to the subject, the data and/or background information comprising at least the subject's age.

5. The assay system in claim 1, wherein the at least one binding agent is a capture molecule which captures a mammalian proteome molecular target belonging to a preferred protein with a molecular weight no greater than about 60,000 Da, including whole protein or fragments thereof including all forms and polymorphic variants.

6. The assay system in claim 3, wherein the output device is adapted to display:

a) measured values of the at least one target marker corresponding to the output signal of the detector;

b) one or more calculated indexes based on the measured values of the at least one target marker;

c) the determination of the likelihood that the subject has a neurological condition or an assessment of brain health of the subject.

7. The assay system in claim 4, further comprising a database comprising data corresponding to a plurality of normal subjects with respect to the at least one target marker and wherein the data and/or background information related to the subject comprises demographic information corresponding to the subject further comprising at least one of the following: race, gender, height and/or weight, and the determination is further based on at least one the above demographic information types in addition to age.

8. An assay system for determining a likelihood that a subject has a neurological condition or to assess brain health comprising:

a test sheet adapted to receive a saliva fluid sample given by a subject;

a test sheet adapted to receive a sample of salivary glands-derived fluid or crevicular fluid the test sheet comprising a base layer and at least one binding agent coated onto the base layer, and adapted to elicit a chemical reaction and bind to at least one target marker in the saliva; and the at least one binding agent adapted to bind with the at least one target marker with lower molecular weights no greater than about 60,000 Daltons (Da) and to provide a color change fluorescence or chemical luminescence upon binding with a certain quantity of the target marker in the saliva with the lower molecular weights wherein the at least one binding agent is a capture molecule which captures a molecular target selected from the group consisting of whole protein or fragments of a preferred protein including all forms and polymorphic variants thereof, and the at least one target marker is an autoreactive antibody directed against one of the selected molecular targets of diagnostic significance.

9. The assay system in claim 8, wherein the assay system is a portable point-of-care device adapted to be used or employed at a point of care or a point of injury.

10. The assay system in claim 9, wherein the at least one binding agent on the test sheet is a single band or strip and the color change, fluorescence or chemical luminescence is adapted to be of variable intensity based on an amount of the target marker in the saliva.

11. The assay system in claim 9, wherein the at least one binding agent on the test sheet is at least two bands or strips, each of the bands represents a level of the target marker in the saliva, and the color change fluorescence or chemical luminescence in the at least two bands or strips allows for semi-quantitative detection of an amount of the target marker in the saliva.

12. The assay system in claim 10, further comprising at least one detector having an output signal adapted to measure the color change fluorescence or chemical luminescence from the chemical reaction, and being deployed or used in close proximity to the test sheet;

a processor adapted to:

a) receive the output signal from the at least one detector;

b) compare the output signal to a control sample comprising levels of the at least one target marker in a normal population; and c) output a determination based at least in part on the comparison, the determination being a likelihood that the subject has a neurological condition or an assessment of brain health of the subject; and an output device adapted to display or indicate at least the determination.

13. The assay system in claim 12, wherein the output device is a display adapted to display:

a) measured values of the at least one target marker corresponding to the output signal of the at least one detector;

b) one or more calculated indexes based on the measured values of the at least one target marker;

c) the determination of the likelihood that the subject has a neurological condition or an assessment of brain health of the subject.

14. The assay system in claim 12, further comprising a database comprising data corresponding to a plurality of normal subjects with respect to the at least one target marker and wherein the data and/or background information related to the subject comprises demographic information corresponding to the subject further comprising at least one of the following: race, gender, height and/or weight, and the determination is further based on at least one of the above demographic information types in addition to age.

15. An assay device for determining a likelihood that a subject has a neurological condition or to assess brain health comprising:

an inlet adapted to receive a salivary or crevicular fluid or other body fluid sample taken from a subject;

at least one assay chamber in fluid connection with the inlet adapted to perform a chemical assay on the salivary or crevicular fluid or other body fluid sample;

a known volume of solution or suspension comprising at least one binding agent adapted to elicit a chemical reaction and bind to a target marker in the salivary or crevicular fluid or other body fluid sample;

at least one sensor having an output signal and adapted to measure an electrical current output from the chemical reaction, and being deployed or used in or in close proximity to the at least one assay chamber;

a processor adapted to:

a) receive the output signal from the at least one sensor;

b) compare the output signal to a control sample comprising levels of the at least one target marker in a normal population; and c) output a determination based at least in part on the comparison, the determination being a likelihood that the subject has a neurological condition or an assessment of brain health of the subject; and an output device adapted to display or indicate at least the determination.

16. The assay device in claim 15, wherein the assay device is a portable point-of-care device adapted to be used or deployed at a point of care or a point of injury.

17. The assay device in claim 16, further comprising an input adapted to allow a user to input data and/or background information related to the subject, the data and/or background information comprising at least the subject's age.

18. The assay device in claim 17, wherein the at least one binding agent is a capture molecule which captures a mammalian proteome molecular target belonging to a preferred protein with a molecular weight no greater than about 60,000 Da, including whole protein or fragments thereof including all forms and polymorphic variants.

19. The assay device in claim 17, wherein the output device is adapted to display:

a) one or more measured values of the at least one target marker corresponding to the signal of the sensor;

b) one or more calculated indexes based on the one or more measured values of the at least one target marker;

c) the determination of the likelihood that the subject has a neurological condition or an assessment of brain health of the subject; and/or d) a recommended treatment based on the determination.

20. The assay device in claim 17, further comprising a database comprising data corresponding to a plurality of normal subjects with respect to the target marker and wherein the data and/or background information related to the subject comprises demographic information corresponding to the subject further comprising at least one of the following: race, gender, height and/or weight, and the determination is further based on at least one of the above demographic information types in addition to age.

* * * * *